US011713313B2

(12) United States Patent
Lewis et al.

(10) Patent No.: US 11,713,313 B2
(45) Date of Patent: *Aug. 1, 2023

(54) GLS1 INHIBITORS FOR TREATING DISEASE

(71) Applicant: Board of Regents, The University of Texas System, Austin, TX (US)

(72) Inventors: Richard Thomas Lewis, Missouri City, TX (US); Philip Jones, Houston, TX (US); Alessia Petrocchi, Houston, TX (US); Naphtali Reyna, Arlington, TX (US); Matthew Hamilton, Missouri City, TX (US); Michael J. Soth, Sugar Land, TX (US); Timothy Heffernan, Sugar Land, TX (US); Michelle Han, Houston, TX (US); Jason P. Burke, Houston, TX (US)

(73) Assignee: Board of Regents, The University of Texas System, Austin, TX (US)

(*) Notice: Subject to any disclaimer, the term of this patent is extended or adjusted under 35 U.S.C. 154(b) by 295 days.

This patent is subject to a terminal disclaimer.

(21) Appl. No.: 16/918,897

(22) Filed: Jul. 1, 2020

(65) Prior Publication Data

US 2021/0122744 A1    Apr. 29, 2021

Related U.S. Application Data

(60) Continuation of application No. 16/152,901, filed on Oct. 5, 2018, now Pat. No. 10,738,043, which is a division of application No. 15/199,100, filed on Jun. 30, 2016, now Pat. No. 10,125,128.

(60) Provisional application No. 62/270,355, filed on Dec. 21, 2015, provisional application No. 62/187,160, filed on Jun. 30, 2015.

(51) Int. Cl.
*C07D 417/14* (2006.01)
*A61K 31/501* (2006.01)
*A61K 45/06* (2006.01)
*C07D 403/14* (2006.01)
*C07D 401/14* (2006.01)
*A61K 31/454* (2006.01)
*A61K 31/4545* (2006.01)
*A61K 31/4439* (2006.01)

(52) U.S. Cl.
CPC ........ *C07D 417/14* (2013.01); *A61K 31/4439* (2013.01); *A61K 31/454* (2013.01); *A61K 31/4545* (2013.01); *A61K 31/501* (2013.01); *A61K 45/06* (2013.01); *C07D 401/14* (2013.01); *C07D 403/14* (2013.01)

(58) Field of Classification Search
None
See application file for complete search history.

(56) References Cited

U.S. PATENT DOCUMENTS

| | | |
|---|---|---|
| 4,399,140 A | 8/1983 | Gacek |
| 4,720,447 A | 1/1988 | De Keyzer |
| 6,153,628 A | 11/2000 | Jin |
| 6,239,137 B1 | 5/2001 | Karmali |
| 7,956,070 B2 | 6/2011 | Alcaraz |
| 7,985,548 B2 | 7/2011 | Lorenzi |
| 9,809,588 B2 | 11/2017 | Di Francesco |
| 10,125,128 B2 | 11/2018 | Lewis |
| 10,150,753 B2 | 12/2018 | Jones |
| 10,344,025 B2 | 7/2019 | Di Francesco |
| 10,722,487 B2 | 7/2020 | Heffernan |
| 10,738,043 B2 | 8/2020 | Lewis |
| 10,766,892 B2 | 9/2020 | Di Francesco |
| 10,899,740 B2 | 1/2021 | Jones |
| 11,045,443 B2 | 6/2021 | Heffernan |
| 11,370,786 B2 | 6/2022 | Di Francesco |
| 2002/0115698 A1 | 8/2002 | Newcomb |
| 2009/0215750 A1 | 8/2009 | Bamberg |
| 2010/0255117 A1 | 10/2010 | Biswal |
| 2011/0229984 A1 | 9/2011 | Lorenzi |
| 2012/0202776 A1 | 8/2012 | Wang |

(Continued)

FOREIGN PATENT DOCUMENTS

| | | |
|---|---|---|
| WO | 1991009848 | 7/1991 |
| WO | 1996037492 | 11/1996 |

(Continued)

OTHER PUBLICATIONS

Aurora Fine Chemicals, 1-[3-(3-aminopyrazol-1-yl)propyl]pyrazole-4-carboxamide, Cat. No. A04.256.259 http://online.aurorafinechemicals.com/StrSearch.asp, Jul. 1, 2015.

(Continued)

*Primary Examiner* — Jeffrey S Lundgren
*Assistant Examiner* — Michael J Schmitt
(74) *Attorney, Agent, or Firm* — Cynthia Hathaway; Lauren L. Stevens; Erik M. Larsen

(57) ABSTRACT

Disclosed herein are compounds and compositions useful in the treatment of GLS1 mediated diseases, such as cancer, having the structure of Formula I:

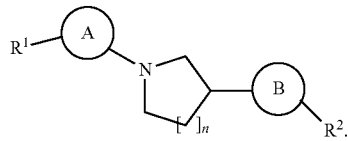

Methods of inhibition GLS1 activity in a human or animal subject are also provided.

12 Claims, No Drawings

(56) References Cited

U.S. PATENT DOCUMENTS

| | | |
|---|---|---|
| 2013/0157998 A1 | 6/2013 | Li |
| 2014/0050699 A1 | 2/2014 | Li |
| 2014/0142081 A1 | 5/2014 | Lemieux |
| 2015/0344466 A1 | 12/2015 | Mitsudera |
| 2015/0368240 A1 | 12/2015 | Bleisch |
| 2016/0002204 A1 | 1/2016 | Di Francesco |
| 2016/0002248 A1 | 1/2016 | Di Francesco |
| 2016/0009704 A1 | 1/2016 | Di Francesco |
| 2016/0058759 A1 | 3/2016 | Heffernan |
| 2017/0001996 A1 | 1/2017 | Lewis |
| 2017/0174661 A1 | 6/2017 | Jones |
| 2017/0291895 A1 | 10/2017 | Di Francesco |
| 2019/0031651 A1 | 1/2019 | Lewis |
| 2019/0134032 A1 | 5/2019 | Heffernan |
| 2019/0274993 A1 | 9/2019 | Heffernan |
| 2020/0368196 A1 | 11/2020 | Heffernan |
| 2020/0407353 A1 | 12/2020 | Di Francesco |
| 2021/0206745 A1 | 7/2021 | Jones |
| 2022/0016069 A1 | 1/2022 | Heffernan |

FOREIGN PATENT DOCUMENTS

| | | |
|---|---|---|
| WO | 1998043962 | 10/1998 |
| WO | 1999026945 | 6/1999 |
| WO | 2008083238 | 7/2008 |
| WO | 2010023946 | 3/2010 |
| WO | 2010099527 | 9/2010 |
| WO | 2010111504 | 9/2010 |
| WO | 2011089995 | 7/2011 |
| WO | 2011143160 | 11/2011 |
| WO | 2013078123 | 5/2013 |
| WO | 2014078645 | 5/2014 |
| WO | 2014079150 | 5/2014 |
| WO | 2014081925 | 5/2014 |
| WO | 2014089048 | 6/2014 |
| WO | 2014119696 | 8/2014 |
| WO | 2015101957 | 7/2015 |
| WO | 2015101958 | 7/2015 |
| WO | WO-2015101957 A2 * | 7/2015 |
| WO | 2016004404 | 1/2016 |
| WO | 2016004413 | 1/2016 |
| WO | 2016004417 | 1/2016 |
| WO | 2016004418 | 1/2016 |
| WO | 2017004359 | 1/2017 |
| WO | 2017112831 | 6/2017 |
| WO | 2019079632 | 4/2019 |

OTHER PUBLICATIONS

Balasubramanian, M. et al., "Asparagine Synthetase: Regulation by Cell Stress and Involvement in Tumor Biology", Am J Physiol Endocrinol Metab., 304(8):E789-99, (2013).
Blair, S. et al., "Glutathione Metabolism in Patients with Non-Small Cell Lung Cancers", Cancer Res., 57(1):152-5, (1997).
Brunton, L. et al., "Chemotherapy of Neoplastic Disease", Goodman and Gilman's, The Pharmacological Basis for Therapeutics, eds., 11:853-903, (2008).
CAPLUS Accession No. 2011:590393; 2 pages, (2011).
CAS Indexed Compounds, 2(1H)-Pyridinone, 1-[3-(1-phenyl-1H-tetrazol-5-yl)propyl]-5(trifluoromethyl), Registry No. 1311902-55-2, Jul. 7, 2011.
CAS Indexed Compounds, 2(1H)-Pyridinone, 1-[3-(3-amino-1H-pyrazol-1-yl)propyl]-4-methyl, Registry No. 1284137-43-4, Apr. 22, 2011.
CAS Indexed Compounds, 2(1H)-Pyridinone, 1-[3-(3-amino-1H-pyrazol-1-yl)propyl]-5-bromo, Registry No. 1272932-30-5, Mar. 31, 2011.
CAS Indexed Compounds, 2(1H)-Pyridinone, 1-[3-(3-amino-1H-pyrazol-1-yl)propyl]-5(trifluoromethyl), Registry No. 1406035-29-7, Nov. 25, 2012.
CAS Indexed Compounds, 2(1H)-Pyridinone, 1-[3-(3-amino-1H-pyrazol-1-yl)propyl], Registry No. 1341730-05-9, Nov. 6, 2011.
CAS Indexed Compounds, 2(1H)-Pyridinone, 1-[3-[3-(3-fluoro-4-methylphenyl)-1,2,4-oxadiazol-5yl]propyl]-5-(trifluoromethyl), Registry No. 1387392-92-8, Aug. 7, 2012.
CAS Indexed Compounds, 2(1H)-Pyridinone, 1-[3-[4-(chloromethyl)-2-thiazolyl]propyl]-4-methyl, Registry No. 1408458-49-0, Nov. 30, 2012.
CAS Indexed Compounds, 2(1H)-Pyridinone, 1-[3-[4-(chloromethyl)-2-thiazolyl]propyl]-5(trifluoromethyl), Registry No. 1484369-40-5, Dec. 1, 2013.
CAS Indexed Compounds, 2(1H)-Pyridinone, 1-[3-[4-(chloromethyl)-2-thiazolyl]propyl], Registry No. 1094436-44-8, Jan. 20, 2009.
CAS Indexed Compounds, 2(1H)-Pyridinone, 1-[4-[4-(chloromethyl)-2-thiazolyl]butyl]-4-methyl, Registry No. 1284050-00-5, Apr. 22, 2011.
CAS Indexed Compounds, 2(1H)-Pyridinone, 1-[4-[4-(chloromethyl)-2-thiazolyl]butyl], Registry No. 1272826-97-7, Mar. 31, 2011.
CAS Indexed Compounds, 2(1H)-Pyridinone, 1-[4-oxo-4-(2-thienyl)butyl]-5-(trifluoromethyl), Registry No. 1456227-69-2, Oct. 6, 2013.
CAS Indexed Compounds, 2(1H)-Pyridinone, 1-[4-oxo-4-(2-thienyl)butyl], Registry No. 1456935-71-9, Oct. 11, 2013.
CAS Indexed Compounds, 2(1H)-Pyridinone, 5-(trifluoromethyl)-1-[3-[3-[3-(trifluoromethyl)phenyl], Registry No. 1100005-80-8, Feb. 3, 2009.
CAS Indexed Compounds, 2(1H)-Pyridinone, 5-bromo-1-[3-(1H-imidazol-1-yl)propyl], Registry No. 1482686-39-4, Nov. 28, 2013.
CAS Indexed Compounds, 2(1H)-Pyridinone, 5-bromo-1-[4-oxo-4-(2-thienyl)butyl], Registry No. 1458260-86-0, Oct. 15, 2013.
CAS Indexed Compounds, 4-Pyridinecarboxylic acid, 1,2-dihydro-1-[3-(1H-imidazol-1-yl)propyl]-2-Oxo, Registry No. 1548114-27-7, Feb. 18, 2014.
CAS Indexed Compounds, Registry No. 1480499-78-2, Nov. 25, 2013.
CAS Registry No. 1355653-66-5 [Database Registry Chemical Abstracts Service, Columbus, Ohio, entry date Nov. 25, 2013]; p. 1.
Dang, C., "Links Between Metabolism and Cancer", Genes Dev., 26(9):877-90, (2012).
Daye, D. et al., "Metabolic Reprogramming in Cancer: Unraveling the Role of Glutamine in Tumorigenesis", Semin Cell Dev Biol., 23(4):362-9, (2012).
Fung, M. et al., "Drug-Induced Amino Acid Deprivation as Strategy for Cancer Therapy", J Hematol Oncol., 10(1):144 pp. 1-18, (2017).
Golub, T. et al., "Molecular Classification of Cancer: Class Discovery and Class Prediction by Gene Expression Monitoring", Science, 286(5439):531-7, (1999).
Gorrini, C. et al., "Modulation of Oxidative Stress as an Anticancer Strategy", Nat Rev Drug Discov., 12(12):931-47, (2013).
Gross, M. et al., "Antitumor Activity of the Glutaminase Inhibitor CB-839 in Triple-Negative Breast Cancer", Mol Cancer Ther., 13(4):890-901, (2014).
Hays, J. et al., "A phase II Clinical Trial of Polyethylene Glycol-Conjugated L-Asparaginase in Patients with Advanced Ovarian Cancer: Early Closure for Safety", Mol Clin Oncol., 1 (3):565-9, (2013).
Hensley, C. et al., "Glutamine and Cancer: Cell Biology, Physiology, and Clinical Opportunities", J Clin Invest., 123(9):3678-84, (2013).
Huang, Q. et al., "Characterization of the Interactions of Potent Allosteric Inhibitors with Glutaminase C, a Key Enzyme in Cancer Cell Glutamine Metabolism", J Biol Chem., 293(10):3535-45, (2018).
Inami, Y. et al., "Persistent Activation of Nrf2 Through p62 in Hepatocellular Carcinoma Cells", J Cell Biol., 193(2):275-84, (2011).
International Application No. PCT/US2015/039134; International Preliminary Report on Patentability, dated Jan. 3, 2017; 06 pages.
International Application No. PCT/US2015/039134; International Search Report and Written Opinion of the International Searching Authority, dated Feb. 9, 2016; 10 pages.
International Application No. PCT/US2015/039143; International Preliminary Report on Patentability, dated Jan. 3, 2017; 06 pages.
International Application No. PCT/US2015/039143; International Search Report and Written Opinion of the International Searching Authority, dated Jan. 11, 2016; 10 pages.

(56) References Cited

OTHER PUBLICATIONS

International Application No. PCT/US2015/039150; International Preliminary Report on Patentability dated Jan. 3, 2017; 6 pages.
International Application No. PCT/US2015/039150; International Search Report and Written Opinion of the International Searching Authority, dated Dec. 4, 2015; 9 pages.
International Application No. PCT/US2015/039153; International Preliminary Report on Patentability, dated Jan. 3, 2017; 10 pages.
International Application No. PCT/US2015/039153; International Search Report and Written Opinion of the International Searching Authority, dated Jan. 7, 2016; 12 pages.
International Application No. PCT/US2016/040364; International Preliminary Report on Patentability, dated Jan. 2, 2018; 7 pages.
International Application No. PCT/US2016/040364; International Search Report and Written Opinion of the International Searching Authority, dated Jan. 5, 2017; 8 pages.
International Application No. PCT/US2016/068149; International Preliminary Report on Patentability, dated Jul. 6, 2018; 4 pages.
International Application No. PCT/US2016/068149; International Search Report and Written Opinion of the International Searching Authority, dated Mar. 27, 2017; 5 pages.
International Application No. PCT/US2018/056567; International Search Report and Written Opinion of the International Searching Authority, dated Apr. 30, 2020; 17 pages.
International Application No. PCT/US2018/056567; International Search Report and Written Opinion of the International Searching Authority, dated Dec. 31, 2018; 20 pages.
Katt, W. et al., "Glutaminase Regulation in Cancer Cells: A Druggable Chain of Events," Drug Discov Today, 19(4)450-7, (2014).
Kroemer, G. et al., "Tumor Cell Metabolism: Cancer's Achilles' Heel", Cancer Cell., 13(6):472-82, (2008).
Lala, P. et al., "Role of Nitric Oxide in Tumor Progression: Lessons From Experimental Tumors", Cancer Metastasis Rev., 17(1):91-106, (1998).
Li, Y. et al., "Sulforaphane Potentiates the Efficacy of 17-Allylamino 17-Demethoxygeldanamycin Against Pancreatic Cancer Through Enhanced Abrogation of Hsp90 Chaperone Function", Nutrition and Cancer, 63(7):1151-9, (2011).
Lin, C. et al., "Deficiency in Asparagine Synthetase Expression in Rectal Cancers Receiving Concurrent Chemoradiotherapy: Negative Prognostic Impact and Therapeutic Relevance", Tumour Biol., 35(7):6823-30, (2014).
Lorenzi, P. et al., "Asparagine Synthetase as a Causal, Predictive Biomarker for L-Asparaginase Activity in Ovarian Cancer Cells", Mol Cancer Ther., 5(11):2613-23, (2006).
Lorenzi, P. et al., "Asparagine Synthetase is a Predictive Biomarker of L-Asparaginase Activity in Ovarian Cancer Cell Lines", Mol Cancer Ther., 7(10):3123-8, (2008).
McMahon, G., "VEGF Receptor Signaling in Tumor Angiogenesis", The Oncologist, 5(Suppl 1):3-10, (2000).
Neidle, S. et al., "Failure Modes in Clinical Development", Cancer Drug Design & Discovery, pp. 427-431, (2008).
Ni, M et al., "Novel RGD Peptidomimetics Embedding 1,2,3-Triazole as Central Scaffold; Synthesis and $\alpha v \beta 3$ Integrin Affinity", Lett Drug Design and Discov., 8(5):401-5, (2011).
Nikonorova, I. et al., "Obesity Challenges the Hepatoprotective Function of the Integrated Stress Response to Asparaginase Exposure in Mice", J Biol Chem., 292(16):6786-98, (2017).
Pinedo, H. et al., "Translational Research: The Role of VEGF in Tumor Angiogenesis", The Oncologist, 5(Suppl 1):1-2, (2000).
Robinson, M. et al., "Novel Mechanism of Inhibition of Rat Kidney-Type Glutaminase by Bis-2-(5-Phenylacetamido-1,2,4-Thiadiazol-2-yl)Ethyl Sulfide (BPTES)", Biochem J., 406(3):407-14, (2007).
Rotblat, B. et al., "NRF2 and p53: Januses in Cancer?", Oncotarget, 3(11):1272-83, (2012).
Shanware, N. et al., "Glutamine: Pleiotropic Roles in Tumor Growth and Stress Resistance", J Mol Med (Berl)., 89(3):229-36, (2011).
Shukla, K. et al., "Design, Synthesis, and Pharmacological Evaluation of Bis-2-(5-Phenylacetamido-1,2,4-Thiadiazol-2-yl)Ethyl Sulfide 3 (BPTES) Analogs as Glutaminase Inhibitors", J Med Chem., 55(23):10551-63, (2012).
Singh, A. et al., "Dysfunctional KEAP1-NRF2 Interaction in Non-Small-Cell Lung Cancer", PLoS Med., 3(10):e420, pp. 1-10, (2006).
Stanovnik, B. et al., "The Tautomerism of Heterocycles: Substituent Tautomerism of Six-Membered Ring Heterocycles", Advances in Heterocyclic Chemistry, 91:1-134, (2006).
Thangavelu, K. et al., "Structural Basis for the Allosteric Inhibitory Mechanism of Human Kidney-Type Glutaminase (KGA) and its Regulation by Raf-Mek-Erk Signaling in Cancer Cell Metabolism", Proc Natl Acad Sci USA, 109(20):7705-10, (2012).
U.S. Appl. No. 14/791,186; Examiner-Initiated Interview Summary, dated Dec. 6, 2016; 1 page.
U.S. Appl. No. 14/791,186; Final Office Action, dated Dec. 6, 2016; 31 pages.
U.S. Appl. No. 14/791,186; Non-Final Office Action, dated May 31, 2016; 13 pages.
U.S. Appl. No. 14/791,186; Notice of Allowability, dated May 11, 2017; 5 pages.
U.S. Appl. No. 14/791,186; Notice of Allowance, dated Mar. 15, 2017; 8 pages.
U.S. Appl. No. 14/791,284; Non-Final Office Action, dated Apr. 11, 2016; 9 pages.
U.S. Appl. No. 14/791,284; Notice of Allowability, dated Nov. 18, 2016; 4 pages.
U.S. Appl. No. 14/791,284; Notice of Allowance, dated Oct. 14, 2016; 9 pages.
U.S. Appl. No. 14/791,307; Non-Final Office Action, dated Jun. 21, 2017; 12 pages.
U.S. Appl. No. 15/199,100; Corrected Notice of Allowability, dated Jul. 30, 2018; 8 pages.
U.S. Appl. No. 15/199,100; Examiner-Initiated Interview Summary, dated Jul. 6, 2018; 1 page.
U.S. Appl. No. 15/199,100; Non-Final Office Action, for dated Sep. 13, 2017; 11 pages.
U.S. Appl. No. 15/199,100; Notice of Allowance, dated Jul. 6, 2018; 11 pages.
U.S. Appl. No. 15/387,560; Non-Final Office Action, dated Jan. 5, 2018; 10 pages.
U.S. Appl. No. 15/387,560; Notice of Allowance, dated Jul. 27, 2018; 5 pages.
U.S. Appl. No. 15/624,168; Non-Final Office Action, dated Jul. 13, 2018; 9 pages.
U.S. Appl. No. 15/624,168; Notice of Allowance, dated Feb. 14, 2019; 20 pages.
U.S. Appl. No. 15/851,407; Non-Final Office Action, dated Jan. 27, 2020; 39 pages.
U.S. Appl. No. 16/152,901; Corrected Notice of Allowability, dated Jun. 19, 2020; 6 pages.
U.S. Appl. No. 16/152,901; Non-Final Office Action, dated Sep. 16, 2019; 15 pages.
U.S. Appl. No. 16/152,901; Notice of Allowance, dated Apr. 1, 2020; 10 pages.
U.S. Appl. No. 16/164,581; Non-Final Office Action, dated Aug. 26, 2019; 13 pages.
U.S. Appl. No. 16/164,581; Notice of Allowance, dated Jan. 30, 2020; 5 pages.
U.S. Appl. No. 16/164,581; Notice of Allowance, dated Mar. 4, 2020; 9 pages.
U.S. Appl. No. 16/241,596; Final Office Action, dated Mar. 5, 2020; 102 pages.
U.S. Appl. No. 16/241,596; Non-Final Office Action, dated Jul. 23, 2019; 21 pages.
U.S. Appl. No. 16/241,596; Notice of Allowance, dated Sep. 21, 2020; 14 pages.
U.S. Appl. No. 16/412,050; Non-Final Office Action, dated Dec. 9, 2019; 30 pages.
U.S. Appl. No. 16/412,050; Notice of Allowance, dated Apr. 10, 2020; 16 pages.
U.S. Appl. No. 16/891,791; Non-Final Office Action, dated Nov. 17, 2020; 6 pages.

(56) References Cited

OTHER PUBLICATIONS

U.S. Appl. No. 17/124,051; Application as filed, dated Dec. 16, 2020; 103 pages.

Van Den Heuvel, A. et al., "Analysis of Glutamine Dependency in Non-Small Cell Lung Cancer", Cancer Biol Ther., 13(12):1185-94, (2012).

Vander Heiden, M. et al., "Targeting Cancer Metabolism: A Therapeutic Window Opens", Nat Rev Drug Discov., 10(9):671-84, (2011).

Vander Heiden, M. et al., "Understanding the Warburg Effect: The Metabolic Requirements of Cell Proliferation", Science, 324(5930):1029-33, (2009).

Vippagunta, S. et al., "Crystalline Solids", Adv Drug Deliv Rev., 48(1):3-26, (2001).

Wang, J. et al., "Targeting Mitochondrial Glutaminase Activity Inhibits Oncogenic Transformation", Cancer Cell, 18(3):207-19, (2010).

Wise, D. et al., "Glutamine Addiction: A New Therapeutic Target in Cancer", Trends Biochem Sci., 35(8):427-33, (2010).

Zhang, D. et al., "Distinct Cysteine Residues in Keap1 Are Required for Keap1-Dependent Ubiquitination of Nrf2 and for Stabilization of Nrf2 by Chemopreventive Agents and Oxidative Stress", Mol Cell Biol., 23(22):8137-51, (2003).

Zhang, P. et al., "Loss of Kelch-Like ECH-Associated Protein 1 Function in Prostate Cancer Cells Causes Chemoresistance and Radioresistance and Promotes Tumor Growth", Mol Cancer Ther., 9(2):336-47, (2010).

Bernstein, J. "Nauka", Polymorphism in Molecular Crystals, pp. 324-330, (2007).

Ivanisevic, I. et al., "Uses of X-Ray Powder Diffraction In the Pharmaceutical Industry", Pharm Sci Encyclopedia, 42 pages, (2010).

U.S. Appl. No. 16/925,974; Corrected Notice of Allowance, dated Feb. 4, 2022; 11 pages.

U.S. Appl. No. 16/925,974; Examiner-Initiated Interview Summary, dated Jan. 31, 2022; 1 page.

U.S. Appl. No. 16/925,974; Notice of Allowance, dated Jan. 26, 2022; 11 pages.

U.S. Appl. No. 17/124,051; Non-Final Office Action, dated Jul. 28, 2022; 16 pages.

U.S. Appl. No. 17/124,051; Notice of Allowance, dated Nov. 3, 2022; 11 pages.

U.S. Appl. No. 17/660,541; Application as filed, dated Apr. 25, 2022; 342 pages.

U.S. Appl. No. 18/163,151; Application as filed, dated Feb. 1, 2023; 103 pages.

\* cited by examiner

GLS1 INHIBITORS FOR TREATING DISEASE

This application is a continuation of U.S. patent application Ser. No. 16/152,901, filed Oct. 5, 2018, which is a division of U.S. patent application Ser. No. 15/199,100, filed Jun. 30, 2016, now U.S. Pat. No. 10,125,128, which claims the benefit of priority of United States Provisional Application Nos. 62/187,160, filed Jun. 30, 2015, and 62/270,355, filed Dec. 21, 2015, the disclosures of which are hereby incorporated by reference as if written herein in their entireties.

BACKGROUND

The present disclosure relates to new heterocyclic compounds and compositions, and their application as pharmaceuticals for the treatment of disease. Methods of inhibition of GLS1 activity in a human or animal subject are also provided for the treatment of diseases such as cancer.

Metabolic deregulation is a hallmark of cancer as tumors exhibit an increased demand for nutrients and macromolecules to fuel their rapid proliferation. Glutamine (Gln), the most abundant amino acid in circulation, plays an essential role in providing cancer cells with biosynthetic intermediates required to support proliferation and survival. Specifically, glutaminolysis, or the enzymatic conversion of glutamine to glutamate, provides proliferating cancer cells with a source of nitrogen for amino acid and nucleotide synthesis, and a carbon skeleton to fuel ATP and NADPH synthesis through the TCA cycle. In addition to supporting cell growth, glutamine metabolism plays a critical role in maintaining cellular redox homeostasis as glutamate can be converted into glutathione, the major intracellular antioxidant.

Glutaminolysis is regulated by mitochondrial glutaminase (GLS), the rate limiting enzyme that catalyzes the conversion of Gln to glutamate and ammonia. Mammalian cells contain 2 genes that encode glutaminase: the kidney-type (GLS1) and liver-type (GLS2) enzymes. Each has been detected in multiple tissue types, with GLS1 being widely distributed throughout the body. GLS1 is a phosphate-activated enzyme that exists in humans as two major splice variants, a long form (referred to as KGA) and a short form (GAC), which differ only in their C-terminal sequences. Both forms of GLS1 are thought to bind to the inner membrane of the mitochondrion in mammalian cells, although at least one report suggests that glutaminase may exist in the intramembrane space, dissociated from the membrane. GLS is frequently overexpressed in human tumors and has been shown to be positively regulated by oncogenes such as Myc. Consistent with the observed dependence of cancer cell lines on glutamine metabolism, pharmacological inhibition of GLS offers the potential to target Gln addicted tumors.

Thus, there is a need for glutaminase inhibitors that are specific and capable of being formulated for in vivo use.

Accordingly, disclosed herein are new compositions and methods for inhibiting glutaminase activity.

Provided is compound of structural Formula I

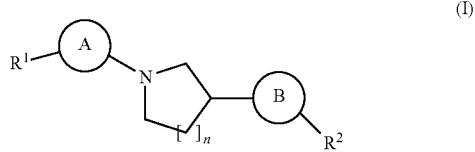

(I)

or a salt thereof, wherein:

n is chosen from 1 and 2;

$R^1$ is chosen from $NR^3C(O)R^3$, $NR^3C(O)OR^3$, $NR^3C(O)N(R^3)_2$, $C(O)N(R^3)_2$, and $N(R^3)_2$;

each $R^3$ is independently chosen from alkyl, aryl, arylalkyl, cycloalkyl, cycloalkylalkyl, H, haloalkyl, heteroaryl, heteroarylalkyl, heterocycloalkyl, heterocycloalkylalkyl, wherein each $R^3$ may be optionally substituted with one to three $R^x$ groups, wherein two $R^3$ groups together with the atoms to which they are attached optionally form an heteroaryl or heterocycloalkyl ring, which may be optionally substituted with one to three $R^x$ groups;

$R^2$ is chosen from $NR^4C(O)R^4$, $NR^4C(O)OR^4$, $NR^4C(O)N(R^4)_2$, $C(O)N(R^4)_2$ and $N(R^4)_2$;

each $R^4$ is independently chosen from alkyl, aryl, arylalkyl, cycloalkyl, cycloalkylalkyl, H, haloalkyl, heteroaryl, heteroarylalkyl, heterocycloalkyl, and heterocycloalkylalkyl, wherein each $R^4$ may be optionally substituted with one to three $R^x$ groups, wherein two $R^4$ groups together with the atoms to which they are attached optionally form an heteroaryl or heterocycloalkyl ring, which may be optionally substituted with one to three $R^x$ groups;

each $R^x$ group is independently chosen from alkoxy, alkoxyalkyl, alkoxyaryl, alkoxyarylalkyl, alkoxycycloalkyl, alkoxycycloalkylalkyl, alkoxyhaloalkyl, alkoxyheteroaryl, alkoxyheteroarylalkyl, alkoxyheterocycloalkyl, alkoxyheterocycloalkylalkyl, alkyl, alkylaryl, alkylarylalkyl, alkylcycloalkyl, alkylcycloalkylalkyl, alkylheteroaryl, alkylheteroarylalkyl, alkylheterocycloalkyl, alkylheterocycloalkylalkyl, aryl, arylalkyl, arylalkyloxy, arylhaloalkyl, aryloxy, cyano, cycloalkyl, cycloalkylalkyl, cycloalkylalkyloxy, cycloalkylhaloalkyl, cycloalkyloxy, halo, haloalkoxy, haloalkoxyalkyl, haloalkoxyaryl, haloalkoxyarylalkyl, haloalkoxycycloalkyl, haloalkoxycycloalkylalkyl, haloalkoxyheteroaryl, haloalkoxyheteroarylalkyl, haloalkoxyheterocycloalkyl, haloalkoxyheterocycloalkylalkyl, haloalkyl, haloalkylaryl, haloalkylarylalkyl, haloalkylcycloalkyl, haloalkylcycloalkylalkyl, haloalkylheteroaryl, haloalkylheteroarylalkyl, haloalkylheterocycloalkyl, haloalkylheterocycloalkylalkyl, haloaryl, haloarylalkyl, haloarylalkyloxy, haloaryloxy, halocycloalkyl, halocycloalkylalkyl, halocycloalkylalkyloxy, halocycloalkyloxy, haloheteroaryl, haloheteroarylalkyl, haloheteroarylalkyloxy, haloheteroaryloxy, haloheterocycloalkyl, haloheterocycloalkylalkyl, haloheterocycloalkylalkyloxy, haloheterocycloalkyloxy, heteroaryl, heteroarylalkyl, heteroarylalkyloxy, heteroarylhaloalkyl, heteroaryloxy, heterocycloalkyl, heterocycloalkylalkyl, heterocycloalkylalkyloxy, heterocycloalkylhaloalkyl, heterocycloalkyloxy, hydroxyl, oxo, $N(R^5)_2$, $NR^5C(O)R^5$, $NR^5C(O)OR^5$, $NR^5C(O)N(R^5)_2$, $C(O)N(R^5)_2$, and $C(O)R^5$;

each $R^5$ is independently chosen from alkyl, aryl, arylalkyl, cycloalkyl, cycloalkylalkyl, H, haloalkyl, heteroaryl, heteroarylalkyl, heterocycloalkyl, and heterocycloalkylalkyl, which may be optionally substituted with one to three $R^z$ groups;

$R^z$ is chosen from alkyl, aryl, arylalkyl, cyano, cycloalkyl, cycloalkylalkyl, H, halo, haloalkyl, heteroaryl, heteroarylalkyl, heterocycloalkyl, and heterocycloalkylalkyl;

A is a monocyclic heteroaryl, which may be optionally substituted with one to three $R^z$ groups;

and Z is a monocyclic heteroaryl, which may be optionally substituted with one to three $R^z$ groups.

Provided is a composition comprising a compound of Formula I and a pharmaceutically acceptable carrier, adjuvant, or vehicle.

Provided is a method of inhibiting GLS1 activity in a biological sample comprising contacting the biological sample with a compound of Formula I.

Provided is a method of treating a GLS1-mediated disorder in a subject in need thereof, comprising the step of administering to the subject a compound of Formula I.

Provided is a method of treating a GLS1-mediated disorder in a subject in need thereof, comprising the sequential or co-administration of a compound of Formula I or a pharmaceutically acceptable salt thereof, and another therapeutic agent.

Provided is a compound of any of Formula I for use in human therapy.

Provided is a compound of any of Formula I for use in treating a GLS1-mediated disease.

Provided is a use of a compound of Formula I for the manufacture of a medicament to treat a GLS1-mediated disease.

DETAILED DESCRIPTION

Abbreviations and Definitions

To facilitate understanding of the disclosure, a number of terms and abbreviations as used herein are defined below as follows:

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e., A alone, B alone or A and B in combination. The expression "A, B and/or C" is intended to mean A alone, B alone, C alone, A and B in combination, A and C in combination, B and C in combination or A, B, and C in combination.

When ranges of values are disclosed, and the notation "from $n_1$ ... to $n_2$" or "between $n_1$ ... and $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

The term "about," as used herein, is intended to qualify the numerical values that it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —C(O)CH$_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds and containing from 2 to 20 carbon atoms. In certain embodiments, the alkenyl will comprise from 2 to 6 carbon atoms. The term "alkenylene" refers to a carbon-carbon double bond system attached at two or more positions such as ethenylene [(—CH=CH—), (—C::C—)]. Examples of suitable alkenyl radicals include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to 20 carbon atoms. In certain embodiments, the alkyl will comprise from 1 to 10 carbon atoms. In further embodiments, the alkyl will comprise from 1 to 6 carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—CH$_2$—). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) radical wherein the term alkyl is as defined above and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon radical having one or more triple bonds and containing from 2 to 20 carbon atoms. In certain embodiments, the alkynyl comprises from 2 to 6 carbon atoms. In further embodiments, the alkynyl comprises from 2 to 4 carbon atoms. The term "alkynylene" refers to a carbon-carbon triple bond attached at two positions such as ethynylene (—C:::C—, —C=C—). Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl" as used herein, alone or in combination, refer to an amino group as described below attached to the parent molecular moiety through a carbonyl group, or vice versa. The term "C-amido" as used herein, alone or in combination, refers to a-C(O)N(RR') group with R and R' as defined herein or as defined by the specifically enumerated "R" groups designated. The term "N-amido" as used herein, alone or in combination, refers to a RC(O)N(R')-group, with R and R' as defined herein or as defined by the specifically enumerated "R" groups designated. The term "acylamino" as used herein, alone or in combination, embraces an acyl group attached to the parent moiety through an amino group. An example of an "acylamino" group is acetylamino ($CH_3C(O)NH—$).

The term "amino," as used herein, alone or in combination, refers to —NRR', wherein R and R' are independently selected from the group consisting of hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl radical derived from an aryl-substituted alkanecarboxylic acid such as benzoyl, napthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent radical $C_6H_4^=$ derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O-carbamyl" as used herein, alone or in combination, refers to a-OC(O)NRR', group with R and R' as defined herein.

The term "N-carbamyl" as used herein, alone or in combination, refers to a ROC(O)NR'-group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein.

In certain embodiments, the cycloalkyl will comprise from 5 to 7 carbon atoms. Examples of such cycloalkyl groups include cyclopropyl, cyclobutyl, cyclopentyl, cyclohexyl, cycloheptyl, tetrahydronapthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—$CF_2$—), chloromethylene (—CHCl—) and the like.

The term "heteroalkyl," as used herein, alone or in combination, refers to a stable straight or branched chain, or cyclic hydrocarbon radical, or combinations thereof, fully saturated or containing from 1 to 3 degrees of unsaturation, consisting of the stated number of carbon atoms and from one to three heteroatoms selected from the group consisting of O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Up to two heteroatoms may be consecutive, such as, for example, —$CH_2$—NH—$OCH_3$.

The term "heteroaryl," as used herein, alone or in combination, refers to a 3 to 15 membered unsaturated heteromonocyclic ring, or a fused monocyclic, bicyclic, or tricyclic ring system in which at least one of the fused rings is aromatic, which contains at least one atom selected from the group consisting of O, S, and N. In certain embodiments, the heteroaryl will comprise from 5 to 7 carbon atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated monocyclic, bicyclic, or tricyclic heterocyclic group containing at least one heteroatom as a ring member, wherein each the heteroatom may be independently selected from the group consisting of nitrogen, oxygen, and sulfur In certain embodiments, the hetercycloalkyl will comprise from 1 to 4 heteroatoms as ring members. In further embodiments, the hetercycloalkyl will comprise from 1 to 2 heteroatoms as ring members. In certain embodiments, the hetercycloalkyl will comprise from 3 to 8 ring members in each ring. In further embodiments, the hetercycloalkyl will comprise from 3 to 7 ring members in each ring. In yet further embodiments, the hetercycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of any one of the formulas disclosed herein.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower," as used herein, alone or in a combination, where not otherwise specifically defined, means containing from 1 to and including 6 carbon atoms.

The term "lower aryl," as used herein, alone or in combination, means phenyl or naphthyl, either of which may be optionally substituted as provided.

The term "lower heteroaryl," as used herein, alone or in combination, means either 1) monocyclic heteroaryl comprising five or six ring members, of which between one and four the members may be heteroatoms selected from the group consisting of O, S, and N, or 2) bicyclic heteroaryl, wherein each of the fused rings comprises five or six ring members, comprising between them one to four heteroatoms selected from the group consisting of O, S, and N.

The term "lower cycloalkyl," as used herein, alone or in combination, means a monocyclic cycloalkyl having between three and six ring members. Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms selected from the group consisting of O, S, and N. Examples of lower heterocycloalkyls include pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to —NRR', wherein R and R' are independently selected from the group consisting of hydrogen, lower alkyl, and lower heteroalkyl, any of which may be optionally substituted. Additionally, the R and R' of a lower amino group may combine to form a five- or six-membered heterocycloalkyl, either of which may be optionally substituted.

The term "mercaptyl" as used herein, alone or in combination, refers to an RS— group, where R is as defined herein.

The term "nitro," as used herein, alone or in combination, refers to —NO$_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The terms "sulfonate," "sulfonic acid," and "sulfonic," as used herein, alone or in combination, refer the —SO$_3$H group and its anion as the sulfonic acid is used in salt formation.

The term "sulfanyl" as used herein, alone or in combination, refers to —S—.

The term "sulfinyl," as used herein, alone or in combination, refers to —S(O)—.

The term "sulfonyl," as used herein, alone or in combination, refers to —S(O)$_2$—.

The term "N-sulfonamido" refers to a RS(=O)$_2$NR'- group with R and R' as defined herein.

The term "S-sulfonamido" refers to a-S(=O)$_2$NRR', group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "O-thiocarbamyl" refers to a —OC(S)NRR', group with R and R' as defined herein.

The term "thiocyanato" refers to a —CNS group.

The term "trihalomethanesulfonamido" refers to a X$_3$CS(O)$_2$NR— group with X is a halogen and R as defined herein.

The term "trihalomethanesulfonyl" refers to a X$_3$CS(O)$_2$— group where X is a halogen.

The term "trihalomethoxy" refers to a X$_3$CO— group where X is a halogen.

The term "trisubstituted silyl," as used herein, alone or in combination, refers to a silicone group substituted at its three free valences with groups as listed herein under the definition of substituted amino. Examples include trimethysilyl, tert-butyldimethylsilyl, triphenylsilyl and the like.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that the group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, N$_3$, SH, SCH$_3$, C(O)CH$_3$, CO$_2$CH$_3$, CO$_2$H, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —CH$_2$CH$_3$), fully substituted (e.g., —CF$_2$CF$_3$), monosubstituted (e.g., —CH$_2$CH$_2$F) or substituted at a level anywhere in-between fully substituted and monosubstituted (e.g., —CH$_2$CF$_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety selected from the group consisting of hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and R" where n=(1, 2, 3, . . . n), every substituent, and every term should be understood to be independent of every other in terms of selection from a group. Should any variable, substituent, or term (e.g., aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. Thus, by way of example only, an unsymmetrical group such as —C(O)N(R)— may be attached to the parent moiety at either the carbon or the nitrogen.

Asymmetric centers exist in the compounds disclosed herein. These centers are designated by the symbols "R" or "S," depending on the configuration of substituents around the chiral carbon atom. It should be understood that the disclosure encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present disclosure includes all cis, trans, syn, anti, entgegen (E), and zusammen (Z) isomers as well as the appropriate mixtures thereof. Additionally, compounds may exist as tautomers; all tautomeric isomers are provided by this disclosure. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered part of larger substructure. A bond may be single, double, or triple unless otherwise specified. A dashed line between two atoms in a drawing of a molecule indicates that an additional bond may be present or absent at that position.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

GLS1 inhibitor is used herein to refer to a compound that exhibits an $IC_{50}$ with respect to GLS1 activity of no more than about 100 µM and more typically not more than about 50 µM, as measured in the GLS1 enzyme assay described generally herein below. $IC_{50}$ is that concentration of inhibitor that reduces the activity of an enzyme (e.g., GLS1) to half-maximal level. Certain compounds disclosed herein have been discovered to exhibit inhibition against GLS1. In certain embodiments, compounds will exhibit an $IC_{50}$ with respect to GLS1 of no more than about 10 µM; in further embodiments, compounds will exhibit an $IC_{50}$ with respect to GLS1 of no more than about 5 µM; in yet further embodiments, compounds will exhibit an $IC_{50}$ with respect to GLS1 of not more than about 1 µM; in yet further embodiments, compounds will exhibit an $IC_{50}$ with respect to GLS1 of not more than about 200 nM, as measured in the GLS1 binding assay described herein.

The phrase "therapeutically effective" is intended to qualify the amount of active ingredients used in the treatment of a disease or disorder or on the effecting of a clinical endpoint.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. Treatment may also be preemptive in nature, i.e., it may include prevention of disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses. Preferably, the patient is a human.

The term "prodrug" refers to a compound that is made more active in vivo. Certain compounds disclosed herein may also exist as prodrugs, as described in Hydrolysis in Drug and Prodrug Metabolism: Chemistry, Biochemistry, and Enzymology (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

The compounds disclosed herein can exist as therapeutically acceptable salts. The present disclosure includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to Pharmaceutical Salts: Properties, Selection, and Use (Stahl, P. Heinrich and Wermuth, Camile G., Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present disclosure contemplates sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

A salt of a compound can be made by reacting the appropriate compound in the form of the free base with the appropriate acid.

Compounds

The present disclosure provides a compound of structural Formula I:

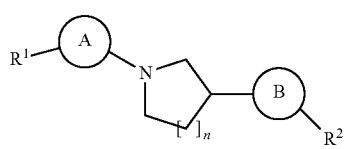

or a salt thereof, wherein:

n is chosen from 1 and 2;

$R^1$ is chosen from $NR^3C(O)R^3$, $NR^3C(O)OR^3$, $NR^3C(O)N(R^3)_2$, $C(O)N(R^3)_2$, and $N(R^3)_2$;

each $R^3$ is independently chosen from alkyl, aryl, arylalkyl, cycloalkyl, cycloalkylalkyl, H, haloalkyl, heteroaryl, heteroarylalkyl, heterocycloalkyl, heterocycloalkylalkyl, wherein each $R^3$ may be optionally substituted with one to three $R^x$ groups, wherein two $R^3$ groups together with the atoms to which they are attached optionally form an heteroaryl or heterocycloalkyl ring, which may be optionally substituted with one to three $R^x$ groups;

$R^2$ is chosen from $NR^4C(O)R^4$, $NR^4C(O)OR^4$, $NR^4C(O)N(R^4)_2$, $C(O)N(R^4)_2$ and $N(R^4)_2$;

each $R^4$ is independently chosen from alkyl, aryl, arylalkyl, cycloalkyl, cycloalkylalkyl, H, haloalkyl, heteroaryl, heteroarylalkyl, heterocycloalkyl, and heterocycloalkylalkyl, wherein each $R^4$ may be optionally substituted with one to three $R^x$ groups, wherein two $R^4$ groups together with the atoms to which they are attached optionally form an heteroaryl or heterocycloalkyl ring, which may be optionally substituted with one to three $R^x$ groups;

each $R^x$ group is independently chosen from alkoxy, alkoxyalkyl, alkoxyaryl, alkoxyarylalkyl, alkoxycycloalkyl, alkoxycycloalkylalkyl, alkoxyhaloalkyl, alkoxyheteroaryl, alkoxyheteroarylalkyl, alkoxyheterocycloalkyl, alkoxyheterocycloalkylalkyl, alkyl, alkylaryl, alkylarylalkyl, alkylcycloalkyl, alkylcycloalkylalkyl, alkylheteroaryl, alkylheteroarylalkyl, alkylheterocycloalkyl, alkylheterocycloalkylalkyl, aryl, arylalkyl, arylalkyloxy, arylhaloalkyl, aryloxy, cyano, cycloalkyl, cycloalkylalkyl, cycloalkylalkyloxy, cycloalkylhaloalkyl, cycloalkyloxy, halo, haloalkoxy, haloalkoxyalkyl, haloalkoxyaryl, haloalkoxyarylalkyl, haloalkoxycycloalkyl, haloalkoxycycloalkylalkyl, haloalkoxyheteroaryl, haloalkoxyheteroarylalkyl, haloalkoxyheterocycloalkyl, haloalkoxyheterocycloalkylalkyl, haloalkyl, haloalkylaryl, haloalkylarylalkyl, haloalkylcycloalkyl, haloalkylcycloalkylalkyl, haloalkylheteroaryl, haloalkylheteroarylalkyl, haloalkylheterocycloalkyl, haloalkylheterocycloalkylalkyl, haloaryl, haloarylalkyl, haloarylalkyloxy, haloaryloxy, halocycloalkyl, halocycloalkylalkyl, halocycloalkylalkyloxy, halocycloalkyloxy, haloheteroaryl, haloheteroarylalkyl, haloheteroarylalkyloxy, haloheteroaryloxy, haloheterocycloalkyl, haloheterocycloalkylalkyl, haloheterocycloalkylalkyloxy, haloheterocycloalkyloxy, heteroaryl, heteroarylalkyl, heteroarylalkyloxy, heteroarylhaloalkyl, heteroaryloxy, heterocycloalkyl, heterocycloalkylalkyl, heterocycloalkylalkyloxy, heterocycloalkylhaloalkyl, heterocycloalkyloxy, hydroxyl, oxo, $N(R^5)_2$, $NR^5C(O)R^5$, $NR^5C(O)OR^5$, $NR^5C(O)N(R^5)_2$, $C(O)N(R^5)_2$, and $C(O)R^5$;

each $R^5$ is independently chosen from alkyl, aryl, arylalkyl, cycloalkyl, cycloalkylalkyl, H, haloalkyl, heteroaryl, heteroarylalkyl, heterocycloalkyl, and heterocycloalkylalkyl, which may be optionally substituted with one to three $R^z$ groups;

$R^z$ is chosen from alkyl, aryl, arylalkyl, cyano, cycloalkyl, cycloalkylalkyl, H, halo, haloalkyl, heteroaryl, heteroarylalkyl, heterocycloalkyl, and heterocycloalkylalkyl;

A is a monocyclic heteroaryl, which may be optionally substituted with one to three $R^z$ groups; and Z is a monocyclic heteroaryl, which may be optionally substituted with one to three $R^z$ groups.

In some embodiments the compound has structural Formula II:

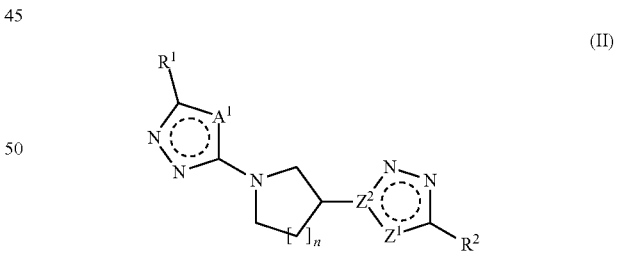

or a salt thereof, wherein:

n is chosen from 1 and 2;

$A^1$ is chosen from S and HC=CH;

$Z^1$ is chosen from S, CH, and HC=CH;

$Z^2$ is N when $Z^1$ is CH, and $Z^2$ is C when $Z^1$ is S or HC=CH;

$R^1$ is chosen from $NR^3C(O)R^3$, $NR^3C(O)OR^3$, $NR^3C(O)N(R^3)_2$, $C(O)N(R^3)_2$, and $N(R^3)_2$;

each $R^3$ is independently chosen from alkyl, aryl, arylalkyl, cycloalkyl, cycloalkylalkyl, H, haloalkyl, heteroaryl, heteroarylalkyl, heterocycloalkyl, heterocycloalkylalkyl, wherein each $R^3$ may be optionally substituted with one to three R$^x$ groups, wherein two R$^3$ groups together with the atoms to which they are attached optionally form an heteroaryl or heterocycloalkyl ring, which may be optionally substituted with one to three R$^x$ groups;

R$^2$ is chosen from NR$^4$C(O)R$^4$, NR$^4$C(O)OR$^4$, NR$^4$C(O)N(R$^4$)$_2$, C(O)N(R$^4$)$_2$ and N(R$^4$)$_2$;

each R$^4$ is independently chosen from alkyl, aryl, arylalkyl, cycloalkyl, cycloalkylalkyl, H, haloalkyl, heteroaryl, heteroarylalkyl, heterocycloalkyl, and heterocycloalkylalkyl, wherein each R$^4$ may be optionally substituted with one to three R$^x$ groups, wherein two R$^4$ groups together with the atoms to which they are attached optionally form an heteroaryl or heterocycloalkyl ring, which may be optionally substituted with one to three R$^x$ groups;

each R$^x$ group is independently chosen from alkoxy, alkoxyalkyl, alkoxyaryl, alkoxyarylalkyl, alkoxycycloalkyl, alkoxycycloalkylalkyl, alkoxyhaloalkyl, alkoxyheteroaryl, alkoxyheteroarylalkyl, alkoxyheterocycloalkyl, alkoxyheterocycloalkylalkyl, alkyl, alkylaryl, alkylarylalkyl, alkylcycloalkyl, alkylcycloalkylalkyl, alkylheteroaryl, alkylheteroarylalkyl, alkylheterocycloalkyl, alkylheterocycloalkylalkyl, aryl, arylalkyl, arylalkyloxy, arylhaloalkyl, aryloxy, cyano, cycloalkyl, cycloalkylalkyl, cycloalkylalkyloxy, cycloalkylhaloalkyl, cycloalkyloxy, halo, haloalkoxy, haloalkoxyalkyl, haloalkoxyaryl, haloalkoxyarylalkyl, haloalkoxycycloalkyl, haloalkoxycycloalkylalkyl, haloalkoxyheteroaryl, haloalkoxyheteroarylalkyl, haloalkoxyheterocycloalkyl, haloalkoxyheterocycloalkylalkyl, haloalkyl, haloalkylaryl, haloalkylarylalkyl, haloalkylcycloalkyl, haloalkylcycloalkylalkyl, haloalkylheteroaryl, haloalkylheteroarylalkyl, haloalkylheterocycloalkyl, haloalkylheterocycloalkylalkyl, haloaryl, haloarylalkyl, haloarylalkyloxy, haloaryloxy, halocycloalkyl, halocycloalkylalkyl, halocycloalkylalkyloxy, halocycloalkyloxy, haloheteroaryl, haloheteroarylalkyl, haloheteroarylalkyloxy, haloheteroaryloxy, haloheterocycloalkyl, haloheterocycloalkylalkyl, haloheterocycloalkylalkyloxy, haloheterocycloalkyloxy, heteroaryl, heteroarylalkyl, heteroarylalkyloxy, heteroarylhaloalkyl, heteroaryloxy, heterocycloalkyl, heterocycloalkylalkyl, heterocycloalkylalkyloxy, heterocycloalkylhaloalkyl, heterocycloalkyloxy, hydroxyl, oxo, N(R$^5$)$_2$, NR$^5$C(O)R$^5$, NR$^5$C(O)OR$^5$, NR$^5$C(O)N(R$^5$)$_2$, C(O)N(R$^5$)$_2$, and C(O)R$^5$;

each R$^5$ is independently chosen from alkyl, aryl, arylalkyl, cycloalkyl, cycloalkylalkyl, H, haloalkyl, heteroaryl, heteroarylalkyl, heterocycloalkyl, and heterocycloalkylalkyl, which may be optionally substituted with one to three R$^z$ groups; and R$^z$ is chosen from alkyl, aryl, arylalkyl, cyano, cycloalkyl, cycloalkylalkyl, H, halo, haloalkyl, heteroaryl, heteroarylalkyl, heterocycloalkyl, and heterocycloalkylalkyl.

In certain embodiments A$^1$ is S.

In certain embodiments A$^1$ is HC=CH.

In certain embodiments Z$^1$ is S; and Z$^2$ is C.

In certain embodiments Z$^1$ is CH; and Z$^2$ is N.

In certain embodiments Z$^1$ is HC=CH; and Z$^2$ is C.

In certain embodiments R$^1$ is chosen from NR$^3$C(O)R$^3$ and C(O)N(R$^3$)$_2$.

In certain embodiments R$^2$ is chosen from NR$^4$C(O)R$^4$ and C(O)N(R$^4$)$_2$.

In some embodiments the compound has structural Formula III:

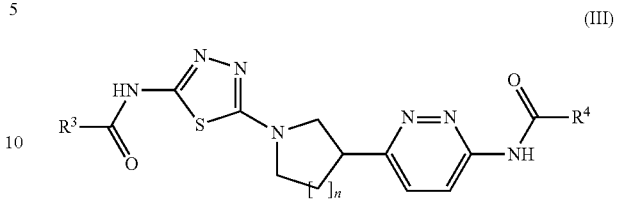

(III)

or a salt thereof, wherein:

n is chosen from 1 and 2;

R$^3$ is independently chosen from alkyl, aryl, arylalkyl, cycloalkyl, cycloalkylalkyl, H, haloalkyl, heteroaryl, heteroarylalkyl, heterocycloalkyl, and heterocycloalkylalkyl, wherein each R$^3$ may be optionally substituted with one to three R$^x$ groups;

R$^4$ is independently chosen from alkyl, aryl, arylalkyl, cycloalkyl, cycloalkylalkyl, H, haloalkyl, heteroaryl, heteroarylalkyl, heterocycloalkyl, and heterocycloalkylalkyl, wherein each R$^4$ may be optionally substituted with one to three R$^x$ groups;

each R$^x$ group is independently chosen from alkoxy, alkoxyalkyl, alkoxyaryl, alkoxyarylalkyl, alkoxycycloalkyl, alkoxycycloalkylalkyl, alkoxyhaloalkyl, alkoxyheteroaryl, alkoxyheteroarylalkyl, alkoxyheterocycloalkyl, alkoxyheterocycloalkylalkyl, alkyl, alkylaryl, alkylarylalkyl, alkylcycloalkyl, alkylcycloalkylalkyl, alkylheteroaryl, alkylheteroarylalkyl, alkylheterocycloalkyl, alkylheterocycloalkylalkyl, aryl, arylalkyl, arylalkyloxy, arylhaloalkyl, aryloxy, cyano, cycloalkyl, cycloalkylalkyl, cycloalkylalkyloxy, cycloalkylhaloalkyl, cycloalkyloxy, halo, haloalkoxy, haloalkoxyalkyl, haloalkoxyaryl, haloalkoxyarylalkyl, haloalkoxycycloalkyl, haloalkoxycycloalkylalkyl, haloalkoxyheteroaryl, haloalkoxyheteroarylalkyl, haloalkoxyheterocycloalkyl, haloalkoxyheterocycloalkylalkyl, haloalkyl, haloalkylaryl, haloalkylarylalkyl, haloalkylcycloalkyl, haloalkylcycloalkylalkyl, haloalkylheteroaryl, haloalkylheteroarylalkyl, haloalkylheterocycloalkyl, haloalkylheterocycloalkylalkyl, haloaryl, haloarylalkyl, haloarylalkyloxy, haloaryloxy, halocycloalkyl, halocycloalkylalkyl, halocycloalkylalkyloxy, halocycloalkyloxy, haloheteroaryl, haloheteroarylalkyl, haloheteroarylalkyloxy, haloheteroaryloxy, haloheterocycloalkyl, haloheterocycloalkylalkyl, haloheterocycloalkylalkyloxy, haloheterocycloalkyloxy, heteroaryl, heteroarylalkyl, heteroarylalkyloxy, heteroarylhaloalkyl, heteroaryloxy, heterocycloalkyl, heterocycloalkylalkyl, heterocycloalkylalkyloxy, heterocycloalkylhaloalkyl, heterocycloalkyloxy, hydroxyl, oxo, N(R$^5$)$_2$, NR$^5$C(O)R$^5$, NR$^5$C(O)OR$^5$, NR$^5$C(O)N(R$^5$)$_2$, C(O)N(R$^5$)$_2$, and C(O)R$^5$;

each R$^5$ is independently chosen from alkyl, aryl, arylalkyl, cycloalkyl, cycloalkylalkyl, H, haloalkyl, heteroaryl, heteroarylalkyl, heterocycloalkyl, and heterocycloalkylalkyl, which may be optionally substituted with one to three R$^z$ groups; and R$^z$ is chosen from alkyl, aryl, arylalkyl, cyano, cycloalkyl, cycloalkylalkyl, H, halo, haloalkyl, heteroaryl, heteroarylalkyl, heterocycloalkyl, and heterocycloalkylalkyl.

In some embodiments the compound has structural Formula IV:

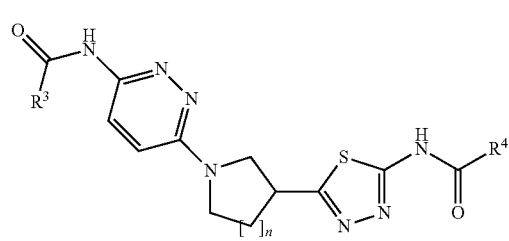

(IV)

or a salt thereof, wherein:

n is chosen from 1 and 2;

$R^3$ is independently chosen from alkyl, aryl, arylalkyl, cycloalkyl, cycloalkylalkyl, H, haloalkyl, heteroaryl, heteroarylalkyl, heterocycloalkyl, and heterocycloalkylalkyl, wherein each $R^3$ may be optionally substituted with one to three $R^x$ groups;

$R^4$ is independently chosen from alkyl, aryl, arylalkyl, cycloalkyl, cycloalkylalkyl, H, haloalkyl, heteroaryl, heteroarylalkyl, heterocycloalkyl, and heterocycloalkylalkyl, wherein each $R^4$ may be optionally substituted with one to three $R^x$ groups;

each $R^x$ group is independently chosen from alkoxy, alkoxyalkyl, alkoxyaryl, alkoxyarylalkyl, alkoxycycloalkyl, alkoxycycloalkylalkyl, alkoxyhaloalkyl, alkoxyheteroaryl, alkoxyheteroarylalkyl, alkoxyheterocycloalkyl, alkoxyheterocycloalkylalkyl, alkyl, alkylaryl, alkylarylalkyl, alkylcycloalkyl, alkylcycloalkylalkyl, alkylheteroaryl, alkylheteroarylalkyl, alkylheterocycloalkyl, alkylheterocycloalkylalkyl, aryl, arylalkyl, arylalkyloxy, arylhaloalkyl, aryloxy, cyano, cycloalkyl, cycloalkylalkyl, cycloalkylalkyloxy, cycloalkylhaloalkyl, cycloalkyloxy, halo, haloalkoxy, haloalkoxyalkyl, haloalkoxyaryl, haloalkoxyarylalkyl, haloalkoxycycloalkyl, haloalkoxycycloalkylalkyl, haloalkoxyheteroaryl, haloalkoxyheteroarylalkyl, haloalkoxyheterocycloalkyl, haloalkoxyheterocycloalkylalkyl, haloalkyl, haloalkylaryl, haloalkylarylalkyl, haloalkylcycloalkyl, haloalkylcycloalkylalkyl, haloalkylheteroaryl, haloalkylheteroarylalkyl, haloalkylheterocycloalkyl, haloalkylheterocycloalkylalkyl, haloaryl, haloarylalkyl, haloarylalkyloxy, haloaryloxy, halocycloalkyl, halocycloalkylalkyl, halocycloalkylalkyloxy, halocycloalkyloxy, haloheteroaryl, haloheteroarylalkyl, haloheteroarylalkyloxy, haloheteroaryloxy, haloheterocycloalkyl, haloheterocycloalkylalkyl, haloheterocycloalkylalkyloxy, haloheterocycloalkyloxy, heteroaryl, heteroarylalkyl, heteroarylalkyloxy, heteroarylhaloalkyl, heteroaryloxy, heterocycloalkyl, heterocycloalkylalkyl, heterocycloalkylalkyloxy, heterocycloalkylhaloalkyl, heterocycloalkyloxy, hydroxyl, oxo, $N(R^5)_2$, $NR^5C(O)R^5$, $NR^5C(O)OR^5$, $NR^5C(O)N(R^5)_2$, $C(O)N(R^5)_2$, and $C(O)R^5$;

each $R^5$ is independently chosen from alkyl, aryl, arylalkyl, cycloalkyl, cycloalkylalkyl, H, haloalkyl, heteroaryl, heteroarylalkyl, heterocycloalkyl, and heterocycloalkylalkyl, which may be optionally substituted with one to three $R^z$ groups;

and $R^z$ is chosen from alkyl, aryl, arylalkyl, cyano, cycloalkyl, cycloalkylalkyl, H, halo, haloalkyl, heteroaryl, heteroarylalkyl, heterocycloalkyl, and heterocycloalkylalkyl.

The compound as recited in claim 2, wherein the compound has structural Formula V:

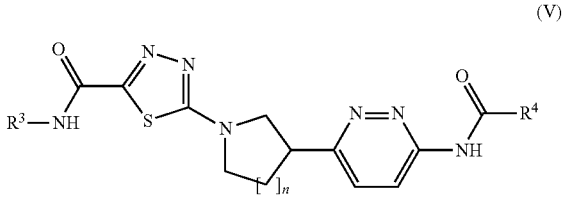

(V)

or a salt thereof, wherein:

n is chosen from 1 and 2;

$R^3$ is independently chosen from alkyl, aryl, arylalkyl, cycloalkyl, cycloalkylalkyl, H, haloalkyl, heteroaryl, heteroarylalkyl, heterocycloalkyl, and heterocycloalkylalkyl, wherein each $R^3$ may be optionally substituted with one to three $R^x$ groups;

$R^4$ is independently chosen from alkyl, aryl, arylalkyl, cycloalkyl, cycloalkylalkyl, H, haloalkyl, heteroaryl, heteroarylalkyl, heterocycloalkyl, and heterocycloalkylalkyl, wherein each $R^4$ may be optionally substituted with one to three $R^x$ groups;

each $R^x$ group is independently chosen from alkoxy, alkoxyalkyl, alkoxyaryl, alkoxyarylalkyl, alkoxycycloalkyl, alkoxycycloalkylalkyl, alkoxyhaloalkyl, alkoxyheteroaryl, alkoxyheteroarylalkyl, alkoxyheterocycloalkyl, alkoxyheterocycloalkylalkyl, alkyl, alkylaryl, alkylarylalkyl, alkylcycloalkyl, alkylcycloalkylalkyl, alkylheteroaryl, alkylheteroarylalkyl, alkylheterocycloalkyl, alkylheterocycloalkylalkyl, aryl, arylalkyl, arylalkyloxy, arylhaloalkyl, aryloxy, cyano, cycloalkyl, cycloalkylalkyl, cycloalkylalkyloxy, cycloalkylhaloalkyl, cycloalkyloxy, halo, haloalkoxy, haloalkoxyalkyl, haloalkoxyaryl, haloalkoxyarylalkyl, haloalkoxycycloalkyl, haloalkoxycycloalkylalkyl, haloalkoxyheteroaryl, haloalkoxyheteroarylalkyl, haloalkoxyheterocycloalkyl, haloalkoxyheterocycloalkylalkyl, haloalkyl, haloalkylaryl, haloalkylarylalkyl, haloalkylcycloalkyl, haloalkylcycloalkylalkyl, haloalkylheteroaryl, haloalkylheteroarylalkyl, haloalkylheterocycloalkyl, haloalkylheterocycloalkylalkyl, haloaryl, haloarylalkyl, haloarylalkyloxy, haloaryloxy, halocycloalkyl, halocycloalkylalkyl, halocycloalkylalkyloxy, halocycloalkyloxy, haloheteroaryl, haloheteroarylalkyl, haloheteroarylalkyloxy, haloheteroaryloxy, haloheterocycloalkyl, haloheterocycloalkylalkyl, haloheterocycloalkylalkyloxy, haloheterocycloalkyloxy, heteroaryl, heteroarylalkyl, heteroarylalkyloxy, heteroarylhaloalkyl, heteroaryloxy, heterocycloalkyl, heterocycloalkylalkyl, heterocycloalkylalkyloxy, heterocycloalkylhaloalkyl, heterocycloalkyloxy, hydroxyl, oxo, $N(R^5)_2$, $NR^5C(O)R^5$, $NR^5C(O)OR^5$, $NR^5C(O)N(R^5)_2$, $C(O)N(R^5)_2$, and $C(O)R^5$;

each $R^5$ is independently chosen from alkyl, aryl, arylalkyl, cycloalkyl, cycloalkylalkyl, H, haloalkyl, heteroaryl, heteroarylalkyl, heterocycloalkyl, and heterocycloalkylalkyl, which may be optionally substituted with one to three $R^z$ groups; and $R^z$ is chosen from alkyl, aryl, arylalkyl, cyano, cycloalkyl, cycloalkylalkyl, H, halo, haloalkyl, heteroaryl, heteroarylalkyl, heterocycloalkyl, and heterocycloalkylalkyl.

The compound as recited in claim 2, wherein the compound has structural Formula VI:

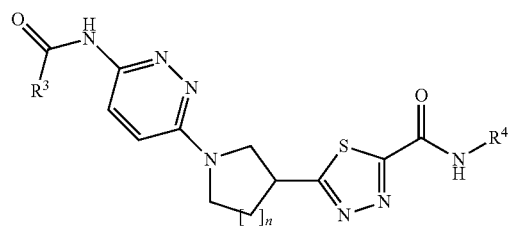

or a salt thereof, wherein:

n is chosen from 1 and 2;

$R^3$ is independently chosen from alkyl, aryl, arylalkyl, cycloalkyl, cycloalkylalkyl, H, haloalkyl, heteroaryl, heteroarylalkyl, heterocycloalkyl, and heterocycloalkylalkyl, wherein each $R^3$ may be optionally substituted with one to three $R^x$ groups;

$R^4$ is independently chosen from alkyl, aryl, arylalkyl, cycloalkyl, cycloalkylalkyl, H, haloalkyl, heteroaryl, heteroarylalkyl, heterocycloalkyl, and heterocycloalkylalkyl, wherein each $R^4$ may be optionally substituted with one to three $R^x$ groups;

each $R^x$ group is independently chosen from alkoxy, alkoxyalkyl, alkoxyaryl, alkoxyarylalkyl, alkoxycycloalkyl, alkoxycycloalkylalkyl, alkoxyhaloalkyl, alkoxyheteroaryl, alkoxyheteroarylalkyl, alkoxyheterocycloalkyl, alkoxyheterocycloalkylalkyl, alkyl, alkylaryl, alkylarylalkyl, alkylcycloalkyl, alkylcycloalkylalkyl, alkylheteroaryl, alkylheteroarylalkyl, alkylheterocycloalkyl, alkylheterocycloalkylalkyl, aryl, arylalkyl, arylalkyloxy, arylhaloalkyl, aryloxy, cyano, cycloalkyl, cycloalkylalkyl, cycloalkylalkyloxy, cycloalkylhaloalkyl, cycloalkyloxy, halo, haloalkoxy, haloalkoxyalkyl, haloalkoxyaryl, haloalkoxyarylalkyl, haloalkoxycycloalkyl, haloalkoxycycloalkylalkyl, haloalkoxyheteroaryl, haloalkoxyheteroarylalkyl, haloalkoxyheterocycloalkyl, haloalkoxyheterocycloalkylalkyl, haloalkyl, haloalkylaryl, haloalkylarylalkyl, haloalkylcycloalkyl, haloalkylcycloalkylalkyl, haloalkylheteroaryl, haloalkylheteroarylalkyl, haloalkylheterocycloalkyl, haloalkylheterocycloalkylalkyl, haloaryl, haloarylalkyl, haloarylalkyloxy, haloaryloxy, halocycloalkyl, halocycloalkylalkyl, halocycloalkylalkyloxy, halocycloalkyloxy, haloheteroaryl, haloheteroarylalkyl, haloheteroarylalkyloxy, haloheteroaryloxy, haloheterocycloalkyl, haloheterocycloalkylalkyl, haloheterocycloalkylalkyloxy, haloheterocycloalkyloxy, heteroaryl, heteroarylalkyl, heteroarylalkyloxy, heteroarylhaloalkyl, heteroaryloxy, heterocycloalkyl, heterocycloalkylalkyl, heterocycloalkylalkyloxy, heterocycloalkylhaloalkyl, heterocycloalkyloxy, hydroxyl, oxo, $N(R^5)_2$, $NR^5C(O)R^5$, $NR^5C(O)OR^5$, $NR^5C(O)N(R^5)_2$, $C(O)N(R^5)_2$, and $C(O)R^5$;

each $R^5$ is independently chosen from alkyl, aryl, arylalkyl, cycloalkyl, cycloalkylalkyl, H, haloalkyl, heteroaryl, heteroarylalkyl, heterocycloalkyl, and heterocycloalkylalkyl, which may be optionally substituted with one to three $R^z$ groups; and $R^z$ is chosen from alkyl, aryl, arylalkyl, cyano, cycloalkyl, cycloalkylalkyl, H, halo, haloalkyl, heteroaryl, heteroarylalkyl, heterocycloalkyl, and heterocycloalkylalkyl.

In particular embodiments the compound, or a salt thereof, is chosen from Examples 1-53 as disclosed herein.

Also provided are embodiments wherein any of embodiment above may be combined with any one or more of these embodiments, provided the combination is not mutually exclusive.

Pharmaceutical Compositions

While it may be possible for the compounds of the subject disclosure to be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the subject disclosure or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Compounds described herein can be administered as follows:

Oral Administration

The compounds of the present invention may be administered orally, including swallowing, so the compound enters the gastrointestinal tract, or is absorbed into the blood stream directly from the mouth, including sublingual or buccal administration.

Suitable compositions for oral administration include solid formulations such as tablets, pills, cachets, lozenges and hard or soft capsules, which can contain liquids, gels, powders, or granules.

In a tablet or capsule dosage form the amount of drug present may be from about 0.05% to about 95% by weight, more typically from about 2% to about 50% by weight of the dosage form.

In addition, tablets or capsules may contain a disintegrant, comprising from about 0.5% to about 35% by weight, more typically from about 2% to about 25% of the dosage form. Examples of disintegrants include methyl cellulose, sodium or calcium carboxymethyl cellulose, croscarmellose sodium, polyvinylpyrrolidone, hydroxypropyl cellulose, starch and the like.

Suitable binders, for use in a tablet, include gelatin, polyethylene glycol, sugars, gums, starch, hydroxypropyl cellulose and the like. Suitable diluents, for use in a tablet, include mannitol, xylitol, lactose, dextrose, sucrose, sorbitol and starch.

Suitable surface active agents and glidants, for use in a tablet or capsule, may be present in amounts from about 0.1% to about 3% by weight, and include polysorbate 80, sodium dodecyl sulfate, talc and silicon dioxide.

Suitable lubricants, for use in a tablet or capsule, may be present in amounts from about 0.1% to about 5% by weight, and include calcium, zinc or magnesium stearate, sodium stearyl fumarate and the like.

Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with a liquid diluent. Dyes or pigments may be added to tablets for identification or to characterize different combinations of active compound doses.

Liquid formulations can include emulsions, solutions, syrups, elixirs and suspensions, which can be used in soft or hard capsules. Such formulations may include a pharmaceutically acceptable carrier, for example, water, ethanol, polyethylene glycol, cellulose, or an oil. The formulation may also include one or more emulsifying agents and/or suspending agents.

Compositions for oral administration may be formulated as immediate or modified release, including delayed or sustained release, optionally with enteric coating.

In another embodiment, a pharmaceutical composition comprises a therapeutically effective amount of a compound of Formula (I) or a pharmaceutically acceptable salt thereof, and a pharmaceutically acceptable carrier.

Parenteral Administration

Compounds of the present invention may be administered directly into the blood stream, muscle, or internal organs by injection, e.g., by bolus injection or continuous infusion. Suitable means for parenteral administration include intravenous, intra-muscular, subcutaneous intraarterial, intraperitoneal, intrathecal, intracranial, and the like. Suitable devices for parenteral administration include injectors (including needle and needle-free injectors) and infusion methods. The formulations may be presented in unit-dose or multi-dose containers, for example sealed ampoules and vials.

Most parenteral formulations are aqueous solutions containing excipients, including salts, buffering, suspending, stabilizing and/or dispersing agents, antioxidants, bacteriostats, preservatives, and solutes which render the formulation isotonic with the blood of the intended recipient, and carbohydrates.

Parenteral formulations may also be prepared in a dehydrated form (e.g., by lyophilization) or as sterile non-aqueous solutions. These formulations can be used with a suitable vehicle, such as sterile water. Solubility-enhancing agents may also be used in preparation of parenteral solutions.

Compositions for parenteral administration may be formulated as immediate or modified release, including delayed or sustained release. Compounds may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Topical Administration

Compounds of the present invention may be administered topically (for example to the skin, mucous membranes, ear, nose, or eye) or transdermally. Formulations for topical administration can include, but are not limited to, lotions, solutions, creams, gels, hydrogels, ointments, foams, implants, patches and the like. Carriers that are pharmaceutically acceptable for topical administration formulations can include water, alcohol, mineral oil, glycerin, polyethylene glycol and the like. Topical administration can also be performed by, for example, electroporation, iontophoresis, phonophoresis and the like.

Typically, the active ingredient for topical administration may comprise from 0.001% to 10% w/w (by weight) of the formulation. In certain embodiments, the active ingredient may comprise as much as 10% w/w; less than 5% w/w; from 2% w/w to 5% w/w; or from 0.1% to 1% w/w of the formulation.

Compositions for topical administration may be formulated as immediate or modified release, including delayed or sustained release.

Rectal, Buccal, and Sublingual Administration

Suppositories for rectal administration of the compounds of the present invention can be prepared by mixing the active agent with a suitable non-irritating excipient such as cocoa butter, synthetic mono-, di-, or triglycerides, fatty acids, or polyethylene glycols which are solid at ordinary temperatures but liquid at the rectal temperature, and which will therefore melt in the rectum and release the drug.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

Administration by Inhalation

For administration by inhalation, compounds may be conveniently delivered from an insufflator, nebulizer pressurized packs or other convenient means of delivering an aerosol spray or powder. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the disclosure may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Other carrier materials and modes of administration known in the pharmaceutical art may also be used. Pharmaceutical compositions of the invention may be prepared by any of the well-known techniques of pharmacy, such as effective formulation and administration procedures. Preferred unit dosage formulations are those containing an effective dose, as herein recited, or an appropriate fraction thereof, of the active ingredient. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. In addition, the route of administration may vary depending on the condition and its severity. The above considerations concerning effective formulations and administration procedures are well known in the art and are described in standard textbooks. Formulation of drugs is discussed in, for example, Hoover, John E., Remington's Pharmaceutical Sciences, Mack Publishing Co., Easton, Pa., 1975; Liberman, et al., Eds., Pharmaceutical Dosage Forms, Marcel Decker, New York, N.Y., 1980; and Kibbe, et al., Eds., Handbook of Pharmaceutical Excipients ($3^{rd}$ Ed.), American Pharmaceutical Association, Washington, 1999.

Methods of Treatment

The present disclosure provides compounds and pharmaceutical compositions that inhibit glutaminase activity, particularly GLS1 activity and are thus useful in the treatment or prevention of disorders associated with GLS1. Compounds and pharmaceutical compositions of the present disclosure selectively modulate GLS1 and are thus useful in the treatment or prevention of a range of disorders associated with GLS1 and include, but are not limited to, cancer, immunological or neurological diseases associated with GLS1.

Neurological Disorders

In some embodiments, the compounds and pharmaceutical compositions of the present disclosure may be useful in the treatment or prevention of neurological diseases.

The most common neurotransmitter is glutamate, derived from the enzymatic conversion of glutamine via glutaminase. High levels of glutamate have been shown to be neurotoxic. Following traumatic insult to neuronal cells, there occurs a rise in neurotransmitter release, particularly glutamate. Accordingly, inhibition of glutaminase has been hypothesized as a means of treatment following an ischemic insult, such as stroke.

Huntington's disease is a progressive, fatal neurological condition. In genetic mouse models of Huntington's disease, it was observed that the early manifestation of the disease correlated with dysregulated glutamate release (Raymond et al., Neuroscience, 2011). In HIV-associated dementia, HIV infected macrophages exhibit upregulated glutaminase activity and increased glutamate release, leading to neuronal damage (Huang et al., J. Neurosci., 2011). Similarly, in another neurological disease, the activated microglia in Rett Syndrome release glutamate causing neuronal damage. The release of excess glutamate has been associated with the up-regulation of glutaminase (Maezawa et al., J. Neurosci, 2010). In mice bred to have reduced glutaminase levels, sensitivity to psychotic-stimulating drugs, such as amphetamines, was dramatically reduced, thus suggesting that glutaminase inhibition may be beneficial in the treatment of schizophrenia (Gaisler-Salomon et al., Neuropsychopharmacology, 2009). Bipolar disorder is a devastating illness that is marked by recurrent episodes of mania and depression. This disease is treated with mood stabilizers such as lithium and valproate; however, chronic use of these drugs appear to increase the abundance of glutamate receptors (Nanavati et al., J. Neurochem., 2011), which may lead to a decrease in the drug's effectiveness over time. Thus, an alternative treatment may be to reduce the amount of glutamate by inhibiting glutaminase. This may or may not be in conjunction with the mood stabilizers. Memantine, a partial antagonist of N-methyl-D-aspartate receptor (NMDAR), is an approved therapeutic in the treatment of Alzheimer's disease. Currently, research is being conducted looking at memantine as a means of treating vascular dementia and Parkinson's disease (Oliverares et al., Curr. Alzheimer Res., 2011). Since memantine has been shown to partially block the NMDA glutamate receptor also, it is not unreasonable to speculate that decreasing glutamate levels by inhibiting glutaminase could also treat Alzheimer's disease, vascular dementia and Parkinson's disease. Alzheimer's disease, bipolar disorder, HIV-associated dementia, Huntington's disease, ischemic insult, Parkinson's disease, schizophrenia, stroke, traumatic insult and vascular dementia are but a few of the neurological diseases that have been correlated to increased levels of glutamate. Thus, inhibiting glutaminase with a compound described herein can reduce or prevent neurological diseases. Therefore, in certain embodiments, the compounds may be used for the treatment or prevention of neurological diseases.

Immunological Disorders

In some embodiments, the compounds and pharmaceutical compositions of the present disclosure may be useful in the treatment or prevention of immunological diseases.

Activation of T lymphocytes induces cell growth, proliferation, and cytokine production, thereby placing energetic and biosynthetic demands on the cell. Glutamine serves as an amine group donor for nucleotide synthesis, and glutamate, the first component in glutamine metabolism, plays a direct role in amino acid and glutathione synthesis, as well as being able to enter the Krebs cycle for energy production (Carr et al., J. Immunol., 2010). Mitogen-induced T cell proliferation and cytokine production require high levels of glutamine metabolism, thus inhibiting glutaminase may serve as a means of immune modulation. In multiple sclerosis, an inflammatory autoimmune disease, the activated microglia exhibit up-regulated glutaminase and release increased levels of extracellular glutamate. Glutamine levels are lowered by sepsis, injury, burns, surgery and endurance exercise (Calder et al., Amino Acids, 1999). These situations put the individual at risk of immunosuppression. In fact, in general, glutaminase gene expression and enzyme activity are both increased during T cell activity. Patients given glutamine following bone marrow transplantation resulted in a lower level of infection and reduced graft v. host disease (Crowther, Proc. Nutr. Soc., 2009). T cell proliferation and activation is involved in many immunological diseases, such as inflammatory bowel disease, Crohn's disease, sepsis, psoriasis, arthritis (including rheumatoid arthritis), multiple sclerosis, graft v. host disease, infections, lupus and diabetes. In an embodiment of the invention, the compounds described herein can be used to treat or prevent immunological diseases.

Cancer

In some embodiments, the compounds and pharmaceutical compositions of the present disclosure may be useful in the treatment or prevention of cancer.

In addition to serving as the basic building blocks of protein synthesis, amino acids have been shown to contribute to many processes critical for growing and dividing cells, and this is particularly true for cancer cells. Nearly all definitions of cancer include reference to dysregulated proliferation. Numerous studies on glutamine metabolism in cancer indicate that many tumors are avid glutamine consumers (Souba, Ann. Surg., 1993; Collins et al., J. Cell. Physiol., 1998; Medina, J. Nutr., 2001; Shanware et al., J. Mol. Med., 2011). An embodiment of the invention is the use of the compounds described herein for the treatment of cancer.

In some embodiments, the compounds of the present disclosure may be used to prevent or treat cancer, wherein the cancer is one or a variant of Acute Lymphoblastic Leukemia (ALL), Acute Myeloid Leukemia (AML), Adrenocortical Carcinoma, AIDS-Related Cancers (Kaposi Sarcoma and Lymphoma), Anal Cancer, Appendix Cancer, Atypical Teratoid/Rhabdoid Tumor, Basal Cell Carcinoma, Bile Duct Cancer (including Extrahepatic), Bladder Cancer, Bone Cancer (including Osteosarcoma and Malignant Fibrous Histiocytoma), Brain Tumor (such as Astrocytomas, Brain and Spinal Cord Tumors, Brain Stem Glioma, Central Nervous System Atypical Teratoid/Rhabdoid Tumor, Central Nervous System Embryonal Tumors, Craniopharyngioma, Ependymoblastoma, Ependymoma, Medulloblastoma, Medulloepithelioma, Pineal Parenchymal Tumors of Intermediate Differentiation, Supratentorial Primitive Neuroectodermal Tumors and Pineoblastoma), Breast Cancer, Bronchial Tumors, Burkitt Lymphoma, Basal Cell Carcinoma, Bile Duct Cancer (including Extrahepatic), Bladder Cancer, Bone Cancer (including Osteosarcoma and Malignant Fibrous Histiocytoma), Carcinoid Tumor, Carcinoma of Unknown Primary, Central Nervous System (such as Atypical Teratoid/Rhabdoid Tumor, Embryonal Tumors and Lymphoma), Cervical Cancer, Childhood Cancers, Chordoma, Chronic Lymphocytic Leukemia (CLL), Chronic Myelogenous Leukemia (CML), Chronic Myeloproliferative Disorders, Colon Cancer, Colorectal Cancer, Craniopharyngioma, Cutaneous T-Cell Lymphoma (Mycosis Fungoides and Sézary Syndrome), Duct, Bile (Extrahepatic), Ductal Carcinoma In Situ (DCIS), Embryonal Tumors (Central Nervous System), Endometrial Cancer, Ependymoblastoma, Ependymoma, Esophageal Cancer, Esthesioneuroblastoma, Ewing Sarcoma Family of Tumors, Extracranial Germ Cell Tumor, Extragonadal Germ Cell Tumor, Extrahepatic Bile Duct Cancer, Eye Cancer (like Intraocular Melanoma, Retinoblastoma), Fibrous Histiocytoma of Bone (including Malignant and Osteosarcoma) Gallbladder Cancer, Gastric (Stomach) Cancer, Gastrointestinal Carcinoid Tumor, Gastrointestinal Stromal Tumors (GIST), Germ Cell Tumor (Extracranial, Extragonadal, Ovarian), Gestational Trophoblastic Tumor, Glioma, Hairy Cell Leukemia, Head and Neck Cancer, Heart Cancer, Hepatocellular (Liver) Cancer, Histiocytosis, Langerhans Cell, Hodgkin Lymphoma, Hypopharyngeal Cancer, Intraocular Melanoma, Islet Cell Tumors (Endocrine, Pancreas), Kaposi Sarcoma, Kidney (including Renal Cell), Langerhans Cell Histiocytosis, Laryngeal Cancer, Leukemia (including Acute Lymphoblastic (ALL), Acute Myeloid (AML), Chronic Lymphocytic (CLL), Chronic Myelogenous (CML), Hairy Cell), Lip and Oral Cavity Cancer, Liver Cancer (Primary), Lobular Carcinoma In Situ (LCIS), Lung Cancer (Non-Small Cell and Small Cell), Lymphoma (AIDS-Related, Burkitt, Cutaneous T-Cell (Mycosis Fungoides and Sézary Syndrome), Hodgkin, Non-Hodgkin, Primary Central Nervous System (CNS), Macroglobulinemia, Waldenstrom, Male Breast Cancer, Malignant Fibrous Histiocytoma of Bone and Osteosarcoma, Medulloblastoma, Medulloepithelioma, Melanoma (including Intraocular (Eye)), Merkel Cell Carcinoma, Mesothelioma (Malignant), Metastatic Squamous Neck Cancer with Occult Primary, Midline Tract Carcinoma Involving NUT Gene, Mouth Cancer, Multiple Endocrine Neoplasia Syndromes, Multiple Myeloma/Plasma Cell Neoplasm, Mycosis Fungoides, Myelodysplastic Syndromes, Myelodysplastic/Myeloproliferative Neoplasms, Myelogenous Leukemia, Chronic (CML), Myeloid Leukemia, Acute (AML), Myeloma and Multiple Myeloma, Myeloproliferative Disorders (Chronic), Nasal Cavity and Paranasal Sinus Cancer, Nasopharyngeal Cancer, Neuroblastoma, Non-Hodgkin Lymphoma, Non-Small Cell Lung Cancer, Oral Cancer, Oral Cavity Cancer, Lip and, Oropharyngeal Cancer, Osteosarcoma and Malignant Fibrous Histiocytoma of Bone, Ovarian Cancer (such as Epithelial, Germ Cell Tumor, and Low Malignant Potential Tumor), Pancreatic Cancer (including Islet Cell Tumors), Papillomatosis, Paraganglioma, Paranasal Sinus and Nasal Cavity Cancer, Parathyroid Cancer, Penile Cancer, Pharyngeal Cancer, Pheochromocytoma, Pineal Parenchymal Tumors of Intermediate Differentiation, Pineoblastoma and Supraten 5 torial Primitive Neuroectodermal Tumors, Pituitary Tumor, Plasma Cell Neoplasm/Multiple Myeloma, Pleuropulmonary Blastoma, Pregnancy and Breast Cancer, Primary Central Nervous System (CNS) Lymphoma, Prostate Cancer, Rectal Cancer, Renal Cell (Kidney) Cancer, Renal Pelvis and Ureter, Transitional Cell Cancer, Retinoblastoma, Rhabdomyosarcoma, Salivary Gland Cancer, Sarcoma (like Ewing Sarcoma Family of Tumors, Kaposi, Soft Tissue, Uterine), Sézary Syndrome, Skin Cancer (such as Melanoma, Merkel Cell Carcinoma, Nonmelanoma), Small Cell Lung Cancer, Small Intestine Cancer, Soft Tissue Sarcoma, Squamous Cell Carcinoma, Squamous Neck Cancer with Occult Primary, Metastatic, Stomach (Gastric) Cancer, Supratentorial Primitive Neuroectodermal Tumors, T-Cell Lymphoma (Cutaneous, Mycosis Fungoides and Sézary Syndrome), Testicular Cancer, Throat Cancer, Thymoma and Thymic Carcinoma, Thyroid Cancer, Transitional Cell Cancer of the Renal Pelvis and Ureter, Trophoblastic Tumor (Gestational), Unknown Primary, Unusual Cancers of Childhood, Ureter and Renal Pelvis, Transitional Cell Cancer, Urethral Cancer, Uterine Cancer, Endometrial, Uterine Sarcoma, Waldenstrom Macroglobulinemia or Wilms Tumor.

In certain embodiments, the cancer to be treated is one specific to T-cells such as T-cell lymphoma and lymphoblastic T-cell leukemia.

In some embodiments, methods described herein are used to treat a disease condition comprising administering to a subject in need thereof a therapeutically effective amount of a compound of Formula I or pharmaceutically acceptable salt thereof, wherein the condition is cancer which has developed resistance to chemotherapeutic drugs and/or ionizing radiation.

Combinations and Combination Therapy

The compounds of the present invention can be used, alone or in combination with other pharmaceutically active compounds, to treat conditions such as those previously described hereinabove. The compound(s) of the present invention and other pharmaceutically active compound(s) can be administered simultaneously (either in the same dosage form or in separate dosage forms) or sequentially. Accordingly, in one embodiment, the present invention comprises methods for treating a condition by administering to the subject a therapeutically-effective amount of one or more compounds of the present invention and one or more additional pharmaceutically active compounds.

In another embodiment, there is provided a pharmaceutical composition comprising one or more compounds of the present invention, one or more additional pharmaceutically active compounds, and a pharmaceutically acceptable carrier.

In another embodiment, the one or more additional pharmaceutically active compounds is selected from the group consisting of anti-cancer drugs, anti-proliferative drugs, and anti-inflammatory drugs.

GLS1 inhibitor compositions described herein are also optionally used in combination with other therapeutic reagents that are selected for their therapeutic value for the condition to be treated. In general, the compounds described herein and, in embodiments where combination therapy is employed, other agents do not have to be administered in the same pharmaceutical composition and, because of different physical and chemical characteristics, are optionally administered by different routes. The initial administration is generally made according to established protocols and then, based upon the observed effects, the dosage, modes of administration and times of administration subsequently modified. In certain instances, it is appropriate to administer a GLS1 inhibitor compound, as described herein, in combination with another therapeutic agent. By way of example only, the therapeutic effectiveness of a GLS1 inhibitor is enhanced by administration of another therapeutic agent (which also includes a therapeutic regimen) that also has therapeutic benefit. Regardless of the disease, disorder or condition being treated, the overall benefit experienced by the patient is either simply additive of the two therapeutic agents or the patient experiences an enhanced (i.e., synergistic) benefit. Alternatively, if a compound disclosed herein has a side effect, it may be appropriate to administer an agent to reduce the side effect; or the therapeutic effectiveness of a compound described herein may be enhanced by administration of an adjuvant.

Therapeutically effective dosages vary when the drugs are used in treatment combinations. Methods for experimentally determining therapeutically effective dosages of drugs and other agents for use in combination treatment regimens are documented methodologies. Combination treatment further includes periodic treatments that start and stop at various times to assist with the clinical management of the patient. In any case, the multiple therapeutic agents (one of which is a GLS1 inhibitor as described herein) may be administered in any order, or simultaneously. If simultaneously, the multiple therapeutic agents are optionally provided in a single, unified form, or in multiple forms (by way of example only, either as a single pill or as two separate pills).

In some embodiments, one of the therapeutic agents is given in multiple doses, or both are given as multiple doses. If not simultaneous, the timing between the multiple doses optionally varies from more than zero weeks to less than twelve weeks.

In addition, the combination methods, compositions and formulations are not to be limited to the use of only two agents, the use of multiple therapeutic combinations are also envisioned. It is understood that the dosage regimen to treat, prevent, or ameliorate the condition(s) for which relief is sought, is optionally modified in accordance with a variety of factors. These factors include the disorder from which the subject suffers, as well as the age, weight, sex, diet, and medical condition of the subject. Thus, the dosage regimen actually employed varies widely, in some embodiments, and therefore deviates from the dosage regimens set forth herein.

The pharmaceutical agents which make up the combination therapy disclosed herein are optionally a combined dosage form or in separate dosage forms intended for substantially simultaneous administration. The pharmaceutical agents that make up the combination therapy are optionally also administered sequentially, with either agent being administered by a regimen calling for two-step administration. The two-step administration regimen optionally calls for sequential administration of the active agents or spaced-apart administration of the separate active agents. The time between the multiple administration steps ranges from a few minutes to several hours, depending upon the properties of each pharmaceutical agent, such as potency, solubility, bioavailability, plasma half-life and kinetic profile of the pharmaceutical agent.

In another embodiment, a GLS1 inhibitor is optionally used in combination with procedures that provide additional benefit to the patient. A GLS1 inhibitor and any additional therapies are optionally administered before, during or after the occurrence of a disease or condition, and the timing of administering the composition containing a GLS1 inhibitor varies in some embodiments. Thus, for example, a GLS1 inhibitor is used as a prophylactic and is administered continuously to subjects with a propensity to develop conditions or diseases in order to prevent the occurrence of the disease or condition. A GLS1 inhibitor and compositions are optionally administered to a subject during or as soon as possible after the onset of the symptoms. While embodiments of the present invention have been shown and described herein, it will be obvious to those skilled in the art that such embodiments are provided by way of example only. Numerous variations, changes, and substitutions will now occur to those skilled in the art without departing from the invention. It should be understood that in some embodiments of the invention various alternatives to the embodiments described herein are employed in practicing the invention.

A GLS1 inhibitor can be used in combination with anti-cancer drugs, including but not limited to the following classes: alkylating agents, anti-metabolites, plant alkaloids and terpenoids, topoisomerase inhibitors, cytotoxic antibiotics, angiogenesis inhibitors and tyrosine kinase inhibitors.

For use in cancer and neoplastic diseases a GLS1 inhibitor may be optimally used together with one or more of the following non-limiting examples of anti-cancer agents: (1) alkylating agents, including but not limited to cisplatin (PLATIN), carboplatin (PARAPLATIN), oxaliplatin (ELOXATIN), streptozocin (ZANOSAR), busulfan (MYLERAN) and cyclophosphamide (ENDOXAN); (2) antimetabolites, including but not limited to mercaptopurine (PURINETHOL), thioguanine, pentostatin (NIPENT), cytosine arabinoside (ARA-C), gemcitabine (GEMZAR), fluorouracil (CARAC), leucovorin (FUSILEV) and methotrexate (RHEUMATREX); (3) plant alkaloids and terpenoids, including but not limited to vincristine (ONCOVIN), vinblastine and paclitaxel (TAXOL); (4) topoisomerase inhibitors, including but not limited to irinotecan (CAMPTOSAR), topotecan (HYCAMTIN) and etoposide (EPOSIN); (5) cytotoxic antibiotics, including but not limited to actinomycin D (COSMEGEN), doxorubicin (ADRIAMYCIN), bleomycin (BLENOXANE) and mitomycin (MITOSOL); (6) angiogenesis inhibitors, including but not limited to sunitinib (SUTENT) and bevacizumab (AVASTIN); and (7) tyrosine kinase inhibitors, including but not limited to imatinib (GLEEVEC), erlotinib (TARCEVA), lapatininb (TYKERB) and axitinib (INLYTA).

Where a subject is suffering from or at risk of suffering from an inflammatory condition, a GLS1 inhibitor compound described herein is optionally used together with one or more agents or methods for treating an inflammatory condition in any combination. Therapeutic agents/treatments for treating an autoimmune and/or inflammatory condition include, but are not limited to any of the following examples: (1) corticosteroids, including but not limited to cortisone, dexamethasone, and methylprednisolone; (2) nonsteroidal anti-inflammatory drugs (NSAIDs), including but not limited to ibuprofen, naproxen, acetaminophen, aspirin, fenoprofen (NALFON), flurbiprofen (ANSAID), ketoprofen, oxaprozin (DAYPRO), diclofenac sodium (VOLTAREN), diclofenac potassium (CATAFLAM), etodolac (LODINE), indomethacin (INDOCIN), ketorolac (TORADOL), sulindac (CLINORIL), tolmetin (TOLECTIN), meclofenamate (MECLOMEN), mefenamic acid (PONSTEL), nabumetone (RELAFEN) and piroxicam (FELDENE); (3) immunosuppressants, including but not limited to methotrexate (RHEUMATREX), leflunomide (ARAVA), azathioprine (IMURAN), cyclosporine (NEORAL, SANDIMMUNE), tacrolimus and cyclophosphamide (CYTOXAN); (4) CD20 blockers, including but not limited to rituximab (RITUXAN); (5) Tumor Necrosis Factor (TNF) blockers, including but not limited to etanercept (ENBREL), infliximab (REMICADE) and adalimumab (HUMIRA); (6) interleukin-1 receptor antagonists, including but not limited to anakinra (KINERET); (7) interleukin-6 inhibitors, including but not limited to tocilizumab (ACTEMRA); (8) interleukin-17 inhibitors, including but not limited to AIN457; (9) Janus kinase inhibitors, including but not limited to tasocitinib; and (10) syk inhibitors, including but not limited to fostamatinib.

Compound Synthesis

Compounds of the present invention can be prepared using methods illustrated in general synthetic schemes and experimental procedures detailed below. General synthetic schemes and experimental procedures are presented for purposes of illustration and are not intended to be limiting. Starting materials used to prepare compounds of the present invention are commercially available or can be prepared using routine methods known in the art.

List of Abbreviations

Ac$_2$O=acetic anhydride; AcCl=acetyl chloride; AcOH=acetic acid; AIBN=azobisisobutyronitrile; aq.=aqueous; Bu$_3$SnH=tributyltin hydride; CD$_3$OD=deuterated methanol; CDCl$_3$=deuterated chloroform; CDI=1,1'-Carbonyldiimidazole; DBU=1,8-diazabicyclo[5.4.0]undec-7-ene; DCM=dichloromethane; DEAD=diethyl azodicarboxylate; DIBAL-H=di-iso-butyl aluminium hydride; DIEA=DIPEA=N,N-diisopropylethylamine; DMAP=4-dimethylaminopyridine; DMF=N,N-dimethylformamide; DMSO-d$_6$=deuterated dimethyl sulfoxide; DMSO=dimethyl sulfoxide; DPPA=diphenylphosphoryl azide; EDC.HCl=EDCI.HCl=1-ethyl-3-(3-dimethylaminopropyl)carbodiimide hydrochloride; Et$_2$O=diethyl ether; EtOAc=ethyl acetate; EtOH=ethanol; h=hour; HATU=2-(1H-7-azabenzotriazol-1-yl)-1,1,3,3-tetramethyl uranium hexafluorophosphate methanaminium; HMDS=hexamethyldisilazane; HOBT=1-hydroxybenzotriazole; i-PrOH=isopropanol; LAH=lithium aluminiumhydride; LiHMDS=Lithium bis(trimethylsilyl)amide; MeCN=acetonitrile; MeOH=methanol; MP-carbonate resin=macroporous triethylammonium methylpolystyrene carbonate resin; MsCl=mesyl chloride; MTBE=methyl tertiary butyl ether; n-BuLi=n-butyllithium; NaHMDS=Sodium bis(trimethylsilyl)amide; NaOMe=sodium methoxide; NaOtBu=sodium t-butoxide; NBS=N-bromosuccinimide; NCS=N-chlorosuccinimide; NMP=N-Methyl-2-pyrrolidone; Pd(Ph$_3$)$_4$=tetrakis(triphenylphosphine)palladium(0); Pd$_2$(dba)$_3$=tris(dibenzylideneacetone)dipalladium(0); PdCl$_2$(PPh$_3$)$_2$=bis(triphenylphosphine)palladium(II) dichloride; PG=protecting group; prep-HPLC=preparative high-performance liquid chromatography; PyBop=(benzotriazol-1-yloxy)tripyrrolidinophosphonium hexafluorophosphate; Pyr=pyridine; RT=room temperature; RuPhos=2-dicyclohexylphosphino-2',6'-diisopropoxybiphenyl; sat.=saturated; ss=saturated solution; t-BuOH=tert-butanol; T3P=Propylphosphonic Anhydride; TEA=Et$_3$N=triethylamine; TFA=trifluoroacetic acid; TFAA=trifluoroacetic anhydride; THF=tetrahydrofuran; Tol=toluene; TsCl=tosyl chloride; XPhos=2-dicyclohexylphosphino-2',4',6'-triisopropylbiphenyl.

General Methods for Preparing Compounds

The following schemes can be used to practice the present invention.

Example 1: N-(6-(3-(5-Amino-1,3,4-thiadiazol-2-yl)piperidin-1-yl)pyridazin-3-yl)-2-phenylacetamide

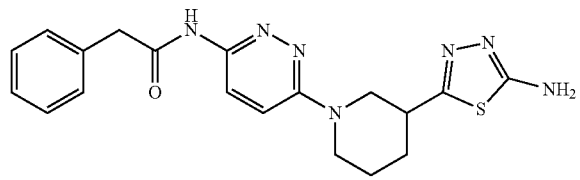 [SMILES: Nc1nnc(C2CCCN(c3ccc(NC(=O)Cc4ccccc4)nn3)C2)s1]

The title compound was synthesized by a similar procedure to Example 13. MS (ES$^+$) C$_{19}$H$_{21}$N$_7$OS requires: 395, found: 396 [M+H]$^+$.

Example 2: 2-Phenyl-N-(6-(3-(5-(2-phenylacetamido)-1,3,4-thiadiazol-2-yl)piperidin-1-yl)pyridazin-3-yl)acetamide

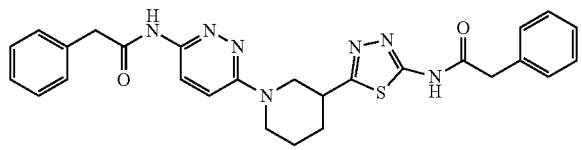 [SMILES: O=C(Cc1ccccc1)Nc1ccc(N2CCCC(c3nnc(NC(=O)Cc4ccccc4)s3)C2)nn1]

The title compound was synthesized by a similar procedure to Example 14. MS (ES$^+$) C$_{27}$H$_{27}$N$_7$O$_2$S requires: 513, found: 514 [M+H]$^+$. $^1$H NMR (600 MHz, MeOD-d$_4$) δ: 8.28 (d, J=10.2 Hz, 1H), 7.92 (d, J=10.2 Hz, 1H), 7.30-7.37 (m, 8H), 7.22-7.29 (m, 2H), 4.30-4.37 (m, 1H), 4.01 (m, 1H), 3.75-3.83 (m, 5H), 3.47-3.57 (m, 2H), 2.26-2.35 (m, 1H), 1.98-2.08 (m, 1H), 1.88-1.97 (m, 1H), 1.75-1.86 (m, 1H).

Example 3: 2-Phenyl-N-(6-(3-(5-(2-(pyridin-2-yl)acetamido)-1,3,4-thiadiazol-2-yl)piperidin-1-yl)pyridazin-3-yl)acetamide

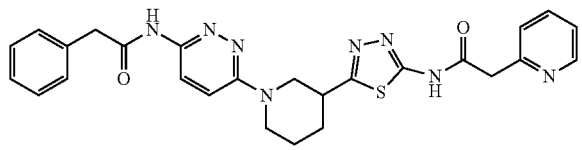 [SMILES: O=C(Cc1ccccc1)Nc1ccc(N2CCCC(c3nnc(NC(=O)Cc4ccccn4)s3)C2)nn1]

The title compound was synthesized by a similar procedure to Example 14. MS (ES⁺) $C_{26}H_{26}N_8O_2S$ requires: 514, found: 515 [M+H]⁺. ¹H NMR (600 MHz, DMSO-$d_6$) δ: 12.80 (brs, 1H), 11.03 (brs, 1H), 8.58 (d, J=4.5 Hz, 1H), 8.09 (d, J=9.8 Hz, 1H), 7.93 (m, 1H), 7.61 (d, J=7.2 Hz, 1H), 7.53 (d, J=7.6 Hz, 1H), 7.43 (m, 1H), 7.30-7.36 (m, 4H), 7.20-7.28 (m, 1H), 4.41 (br d, 1H), 3.99-4.13 (m, 3H), 3.72 (s, 2H), 3.35-3.50 (m, 2H), 3.25 (br t, 1H), 2.17 (m, 1H), 1.76-1.93 (m, 2H), 1.58-1.72 (m, 1H).

Example 4: N-(6-(3-(5-Acetamido-1,3,4-thiadiazol-2-yl)piperidin-1-yl)pyridazin-3-yl)-2-phenylacetamide

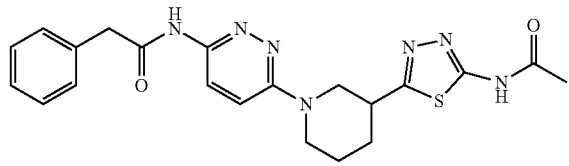 [SMILES: CC(=O)Nc1nnc(C2CCCN(c3ccc(NC(=O)Cc4ccccc4)nn3)C2)s1]

The title compound was synthesized by a similar procedure to Example 14. MS (ES⁺) $C_{21}H_{23}N_7O_2S$ requires: 437, found: 438 [M+H]⁺.

Example 6: N-Methyl-1-(1-(6-(2-(3-(trifluoromethoxy)phenyl)acetamido)pyridazin-3-yl)pyrrolidin-3-yl)-1H-1,2,3-triazole-4-carboxamide

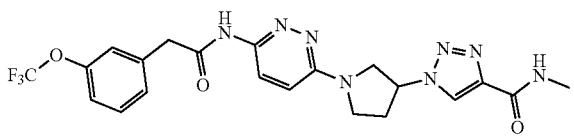 [SMILES: CNC(=O)c1cn(C2CCN(c3ccc(NC(=O)Cc4cccc(OC(F)(F)F)c4)nn3)C2)nn1]

The title compound was synthesized by a similar procedure to Example 8 step 9. MS (ES⁺) $C_{21}H_{21}F_3N_8O_3$ requires: 490, found: 491[M+H]⁺.

Example 7: N-(Pyridin-2-ylmethyl)-1-(1-(6-(2-(3-(trifluoromethoxy)phenyl)acetamido)pyridazin-3-yl)piperidin-3-yl)-1H-1,2,3-triazole-4-carboxamide

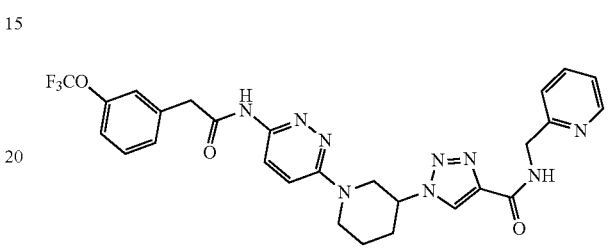

The title compound was synthesized by a similar procedure to Example 8, step 9. MS (ES⁺) $C_{27}H_{26}F_3N_9O_3$ requires: 581, found: 582 [M+H]⁺.

Example 8: N-(pyridin-2-ylmethyl)-1-(1-(6-(2-(3-(trifluoromethoxy)phenyl)acetamido)pyridazin-3-yl)pyrrolidin-3-yl)-1H-1,2,3-triazole-4-carboxamide

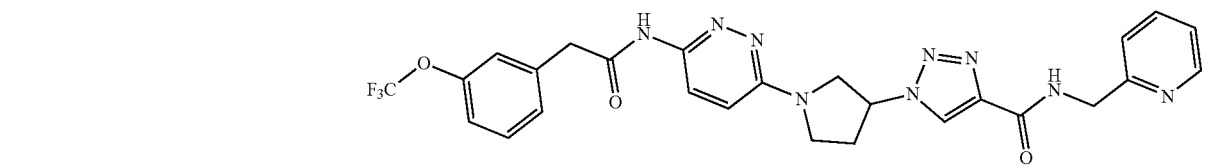 [SMILES: O=C(Cc1cccc(OC(F)(F)F)c1)Nc1ccc(N2CCC(n3cc(C(=O)NCc4ccccn4)nn3)C2)nn1]

Steps 1-9

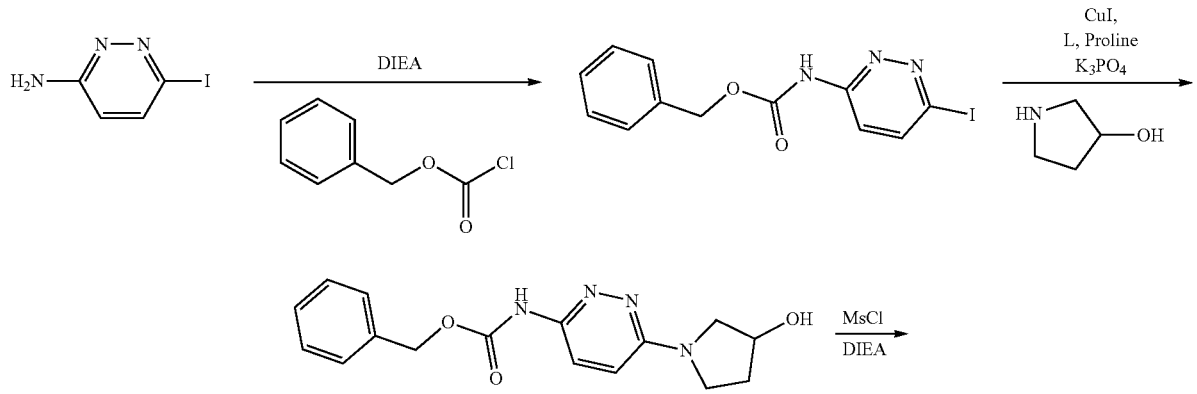

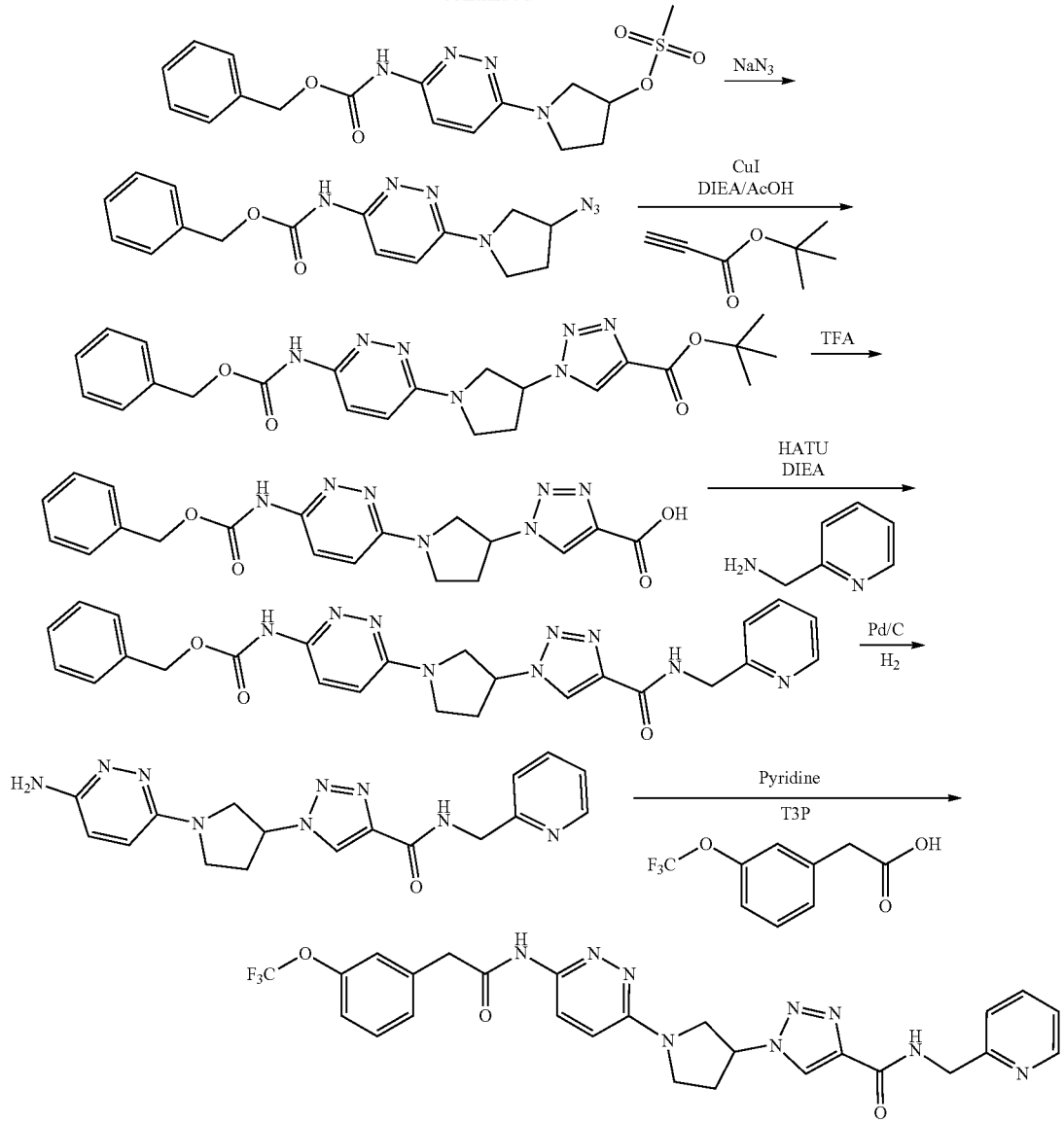

Step 1: Benzyl (6-iodopyridazin-3-yl)carbamate

To a mixture of 6-iodopyridazin-3-amine (3 g, 13.57 mmol) and DIEA (2.85 ml, 16.29 mmol) in chloroform (8 ml) under nitrogen in an ice bath was added a benzyl chloroformate (2.78 g, 16.29 mmol) dropwise and the reaction was stirred in the ice bath for 10 min then the mixture was allowed to warm to room temperature overnight. The reaction mixture was filtered and the resulting solid was washed with minimal DCM. More solid formed in filtrate and was recovered by filtration. The off white solid was washed with minimal DCM to give the product (2.46 g). Additional product was isolated from the filtrate after purification via silica gel chromatography (0-60% hexanes in EtOAc; 0.5 g as a white solid) to give the title compound (total combined, 3 g, 62%) as an off-white solid. MS (ES+) $C_{12}H_{10}IN_3O_2$ requires: 355, found: 356 [M+H]+.

Step 2: Benzyl (6-(3-hydroxypyrrolidin-1-yl) pyridazin-3-yl)carbamate

To a vial containing benzyl (6-iodopyridazin-3-yl)carbamate (1 g, 2.82 mmol), pyrrolidin-3-ol (0.294 g, 3.38 mmol), L-proline, (65 mg, 0.563 mmol), $K_3PO_4$ (1.793 g, 8.45 mmol), and copper (I) iodide (0.054 g, 0.282 mmol) was added DMSO (5 ml) (previously degassed with nitrogen) and the resulting mixture was stirred at 50° C. for 20 hrs. To the mixture was added copper (I) iodide (0.108 g, 0.564 mmol) and $K_3PO_4$ (0.161 g, 1.69 mmol), and 2-(dimethylamino)acetic acid (0.058 g, 0.563 mmol), and the reaction heated at 50° C. for 2 days. The reaction was poured into water (200 ml) and diluted with DCM (100 ml) and the resulting mixture was filtered and the resulting black solid was washed with DCM. The filtrate mixture was separated and the aqueous layer was extracted with DCM (3×100 ml). The organic layers were combined, washed with brine, dried over $MgSO_4$, filtered through sintered glass funnel, concentrated, and the residue was purified via silica gel chromatography (0-30% of 80/20/1 DCM/MeOH/NH$_4$OH solution in DCM) to give the title compound (225 mg, 25%) as a white solid. MS (ES$^+$) C$_{16}$H$_{18}$N$_4$O$_3$ requires: 314, found: 315 [M+H]$^+$.

Step 3: 1-(6-(((benzyloxy)carbonyl)amino) pyridazin-3-yl)pyrrolidin-3-yl methanesulfonate To a suspension of benzyl (6-(3-hydroxypyrrolidin-1-yl)pyridazin-3-yl)carbamate (61 mg, 0.194 mmol) and DIEA (0.051 ml, 0.291 mmol) in DCM (2 ml) was cooled under nitrogen in an ice bath and methanesulfonyl chloride (0.023 ml, 0.291 mmol) was added and the resulting mixture was stirred in the ice bath for 3 min then removed and warmed to room temperature. To the reaction was added DIEA (47 µl, 0.269 mmol), cooled in the ice bath, methanesulfonyl chloride (14 µL, 0.180 mmol) was added, and the reaction was stirred and allowed to warm to room temperature over 4 hrs. The reaction was cooled in an ice bath and DIEA (47 µl, 0.269 mmol) and methanesulfonyl chloride (14 µL, 0.180 mmol) were added, and the reaction was stirred and allowed to warm to over 1 hr. The completed reaction was diluted with DCM, washed with water and saturated NaCl, dried over MgSO$_4$, filtered, and concentrated to give the title compound (79 mg, 88%). MS (ES$^+$) C$_{17}$H$_{20}$N$_4$O$_4$S requires: 392, found: 393 [M+H]$^+$.

Step 4: Benzyl (6-(3-azidopyrrolidin-1-yl)pyridazin-3-yl)carbamate

To a solution of 1-(6-(((benzyloxy)carbonyl)amino)pyridazin-3-yl)pyrrolidin-3-yl methanesulfonate (76 mg, 0.194 mmol) in DMF (1 ml) was added sodium azide (25.2 mg, 0.387 mmol) and the resulting mixture was stirred at 50° C. for 60 hrs. The reaction was concentrated, diluted with DCM, washed with water and saturated NaCl, dried over MgSO$_4$, filtered, and concentrated to give the title compound (43.9 mg, 66%) as an off-white solid. MS (ES$^+$) C$_{16}$H$_{17}$N$_7$O$_2$ requires: 339, found: 340 [M+H]$^+$.

Step 5: Tert-butyl 1-(1-(6-(((benzyloxy)carbonyl)amino)pyridazin-3-yl)pyrrolidin-3-yl)-1H-1,2,3-triazole-4-carboxylate To a solution of benzyl (6-(3-azidopyrrolidin-1-yl)pyridazin-3-yl)carbamate (41 mg, 0.121 mmol), DIEA (2.110 µl, 0.012 mmol), AcOH (0.692 µl, 0.012 mmol) in DCM (1 ml) were added tert-butyl propiolate (18.29 mg, 0.145 mmol) and CuI (1.150 mg, 6.04 µmol) and the resulting mixture was stirred at room temperature for 2 hrs. The reaction was diluted with DCM and washed with dilute aqueous NH$_4$OH and saturated NaCl, dried over MgSO$_4$, filtered, and concentrated to give the title compound (45.6 mg, 81%) as a light brown solid. MS (ES$^+$) C$_{23}$H$_{27}$N$_7$O$_4$ requires: 465, found: 466 [M+H]$^+$.

Step 6: 1-(1-(6-(((benzyloxy)carbonyl)amino)pyridazin-3-yl)pyrrolidin-3-yl)-1H-1,2,3-triazole-4-carboxylic acid To a suspension of tert-butyl 1-(1-(6-(((benzyloxy)carbonyl)amino)pyridazin-3-yl)pyrrolidin-3-yl)-1H-1,2,3-triazole-4-carboxylate (41 mg, 0.088 mmol) in DCM (0.5 ml) was added TFA (0.339 ml, 4.40 mmol) and the resulting mixture was stirred at room temperature for 2 hrs. The reaction was concentrated and dried multiple times from DCM/toluene and DCM/hexanes to give the title compound as a TFA salt (1:1) (46 mg, 100%) as an off white solid. MS (ES$^+$) C$_{19}$H$_{19}$N$_7$O$_4$ requires: 409, found: 410 [M+H]$^+$.

Step 7: Example 5: Benzyl (6-(3-(4-((pyridin-2-ylmethyl)carbamoyl)-1H-1,2,3-triazol-1-yl)pyrrolidin-1-yl)pyridazin-3-yl)carbamate

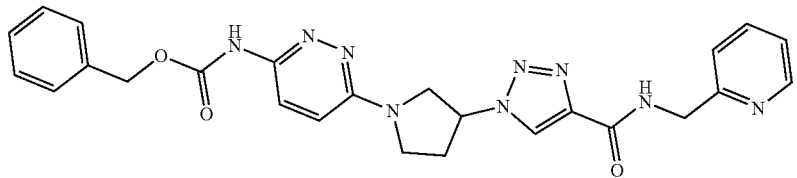 [SMILES: O=C(Nc1ccc(N2CCC(n3cc(C(=O)NCc4ccccn4)nn3)C2)nn1)OCc1ccccc1]

To a solution of 1-(1-(6-(((benzyloxy)carbonyl)amino)pyridazin-3-yl)pyrrolidin-3-yl)-1H-1,2,3-triazole-4-carboxylic acid compound with 2,2,2-trifluoroacetic acid (1:1) (23 mg, 0.044 mmol) in DMF (1 ml) was added pyridin-2-ylmethanamine (14.26 mg, 0.132 mmol), DIEA (46 µl, 0.264 mmol), and HATU (50 mg, 0.132 mmol) and the reaction was stirred at room temperature until completion. The reaction was concentrated, supported on Celite and purified by silica gel chromatography (0-50% of 80/20/1 DCM/MeOH/NH$_4$OH solution in DCM) to give the title compound (11.7 mg, 53%) as an off-white solid. MS (ES$^+$) C$_{25}$H$_{25}$N$_9$O$_3$ requires: 499, found: 500 [M+H]$^+$.

Step 8: 1-(1-(6-aminopyridazin-3-yl)pyrrolidin-3-yl)-N-(pyridin-2-ylmethyl)-1H-1,2,3-triazole-4-carboxamide Ta a solution of benzyl (6-(3-(4-((pyridin-2-ylmethyl)carbamoyl)-1H-1,2,3-triazol-1-yl)pyrrolidin-1-yl)pyridazin-3-yl)carbamate (9 mg, 0.018 mmol) in MeOH (1 ml) was purged with nitrogen and then palladium on carbon 10% (2 mg, 1.8 µm) was added. The resulting mixture was exposed to hydrogen (1 atm) for 4 hrs. The reaction was filtered through celite, rinsed with DCM/MeOH, and the filtrate concentrated. The residue was applied to the same hydrogenation procedure for 2 hr with palladium on carbon 10% (3 mg, 2.8 µm) but with the addition of concentrated HCl (10 µl). The reaction was filtered through celite, filter cake rinsed with DCM/MeOH, and the filtrate concentrated and dried from DCM/hexanes to give the title compound which was used as is for the next step. MS (ES$^+$) C$_{21}$H$_{21}$F$_3$N$_8$O$_3$ requires: 365, found: 366 [M+H]$^+$.

Step 9: N-(pyridin-2-ylmethyl)-1-(1-(6-(2-(3-(trifluoromethoxy)phenyl)acetamido)pyridazin-3-yl)pyrrolidin-3-yl)-1H-1,2,3-triazole-4-carboxamide To a solution of 1-(1-(6-aminopyridazin-3-yl)pyrrolidin-3-yl)-N-(pyridin-2-ylmethyl)-1H-1,2,3-triazole-4-carboxamide (9 mg, 0.025 mmol) in DMF (100 μl) were added 2-(3-(trifluoromethoxy)phenyl)acetic acid (10.84 mg, 0.049 mmol) and pyridine (11.95 μl, 0.148 mmol), followed by T3P (50% solution in EtOAc, 62 μl, 0.099 mmol) and the resulting mixture was stirred at 80° C. for 3 hrs. To the reaction was added 2-(3-(trifluoromethoxy)phenyl)acetic acid (33 mg, 0.15 mmol), pyridine (36 μl, 0.45 mmol), followed by T3P (50% solution in EtOAc, 186 μl, 0.30 mmol) and the reaction was stirred at 80° C. overnight. The reaction was concentrated, supported on celite and purified by flash chromatography (0-60% of 80/20/1 DCM/MeOH/NH₄OH solution in DCM) to give the product. The product was further purified by reverse phase preparative HPLC (Mobile phase: A=0.1% TFA/H₂O, B=0.1% TFA/MeCN; Gradient: B=10-60%; 12 min; Column: Y) to give the title compound (2.3 mg, 16%) as an off-white solid. MS (ES⁺) $C_{26}H_{24}F_3N_9O_3$ requires: 567, found: 568 [M+H]⁺. ¹H NMR (600 MHz, DMSO-$d_6$) δ: 11.02 (brs, 1H), 9.10 (t, J=5.9 Hz, 1H), 8.75 (s, 1H), 8.54 (d, J=4.5 Hz, 1H), 8.10 (d, J=9.4 Hz, 1H), 7.83 (t, J=7.6 Hz, 1H), 7.44-7.50 (m, 1H), 7.31-7.40 (m, 4H), 7.20-7.28 (m, 2H), 5.55-5.57 (m, 1H), 4.58 (d, J=6.0 Hz, 2H), 3.99-4.10 (m, 2H), 3.81 (s, 2H), 3.68-3.74 (m, 2H), 2.64-2.69 (m, 1H), 2.54-2.61 (m, 1H).

Example 9: 2-(pyridin-2-yl)-N-(6-(3-(5-(2-(pyridin-2-yl)acetamido)-1,3,4-thiadiazol-2-yl)pyrrolidin-1-yl)pyridazin-3-yl)acetamide

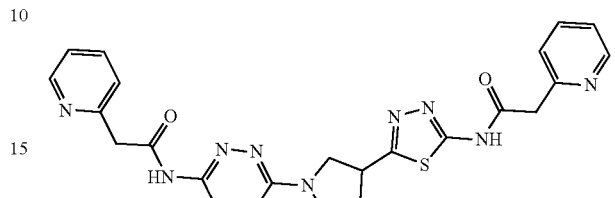

Steps 1-4

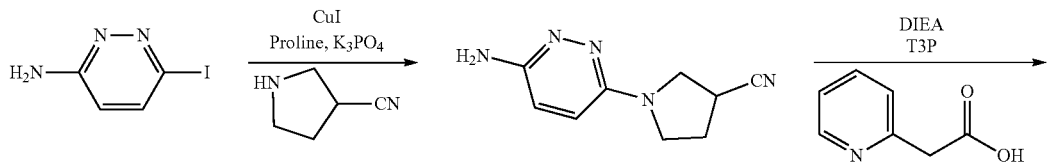

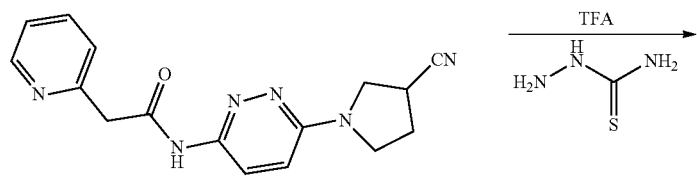

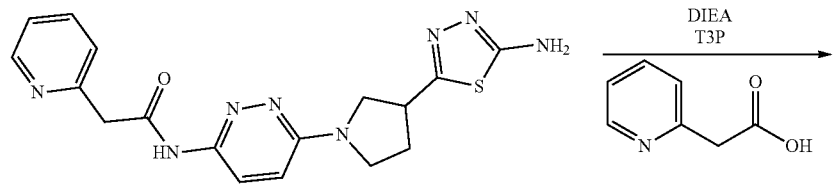

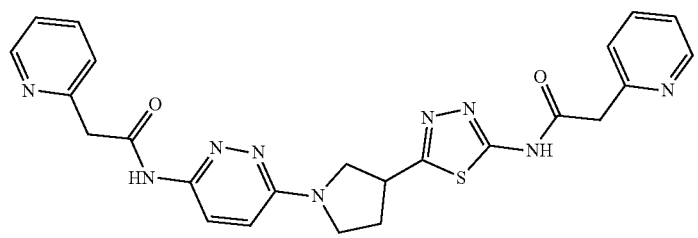

Step 1: 1-(6-aminopyridazin-3-yl)pyrrolidine-3-carbonitrile

To a vial containing 6-iodopyridazin-3-amine, pyrrolidine-3-carbonitrile hydrochloride, L-proline ((S)-pyrrolidine-2-carboxylic acid) (20.84 mg, 0.181 mmol), $K_3PO_4$ (768 mg, 3.62 mmol), and copper (I) iodide (17.24 mg, 0.090 mmol) was added DMSO (2 ml) (previously degassed with nitrogen) and the resulting mixture was stirred at 50° C. for 20 hrs. The reaction was diluted with MeOH and acidified with AcOH. The mixture was loaded on SCX resin and the product isolated by a similar procedure to that described in Tetrahedron Letters, 55 (2014), 5186-5190 to give crude product (80 mg). The crude was supported on celite and purified via silica gel chromatography (0-100% of 80/20/1 DCM/MeOH/$NH_4OH$ solution in DCM) to give the title compound (55 mg, 19%) as a pale yellow solid. MS ($ES^+$) $C_9H_{11}N_5$ requires: 189, found: 190 $[M+H]^+$.

Step 2: N-(6-(3-cyanopyrrolidin-1-yl)pyridazin-3-yl)-2-(pyridin-2-yl)acetamide To a round bottom flask containing 1-(6-aminopyridazin-3-yl)pyrrolidine-3-carbonitrile (55 mg, 0.180 mmol) was added DMF (1 ml), 2-(pyridin-2-yl)acetic acid hydrochloride (101 mg, 0.582 mmol), and DIEA (0.203 ml, 1.161 mmol), the solution was cooled in an ice bath under $N_2$ and to this was added T3P (50% solution in EtOAc, 0.370 ml, 0.581 mmol) dropwise. The reaction was allowed to warm to room temperature overnight. To the reaction was added saturated $NaHCO_3$ (50 ml) and the resulting mixture stirred for 30 min and the precipitate was filtered off and washed with water and hexanes. The yellow solid was dissolved in DCM/MeOH, adsorbed onto Celite and purified via flash chromatography (0-100% of an 80/20/1 DCM/MeOH/$NH_4OH$ solution in DCM) to give the title compound (26 mg, 46.8%) as a yellow solid. MS ($ES^+$) $C_{16}H_{16}N_6O$ requires: 308, found: 309 $[M+H]^+$.

Step 3: N-(6-(3-(5-amino-1,3,4-thiadiazol-2-yl)pyrrolidin-1-yl)pyridazin-3-yl)-2-(pyridin-2-yl)acetamide To a solution of N-(6-(3-cyanopyrrolidin-1-yl)pyridazin-3-yl)-2-(pyridin-2-yl)acetamide (23 mg, 0.075 mmol) in TFA (200 μl, 2.60 mmol) was added hydrazinecarbothioamide (7.48 mg, 0.082 mmol) and the resulting mixture was stirred at 60° C. for 17 hrs and 80° C. for 2 hrs. The reaction was concentrated and azeotroped from DCM/EtOH, DCM/MeOH/$NH_4OH$, and DCM/hexanes. The residue was adsorbed onto Celite and purified via flash chromatography (0-50% of an 80/20/1 DCM/MeOH/$NH_4OH$ solution in DCM) to give the title compound (25 mg, 88%) as an off white solid. MS ($ES^+$) $C_{17}H_{18}N_8OS$ requires: 382, found: 383 $[M+H]^+$.

Step 4: 2-(pyridin-2-yl)-N-(6-(3-(5-(2-(pyridin-2-yl)acetamido)-1,3,4-thiadiazol-2-yl)pyrrolidin-1-yl)pyridazin-3-yl)acetamide To a suspension of N-(6-(3-(5-amino-1,3,4-thiadiazol-2-yl)pyrrolidin-1-yl)pyridazin-3-yl)-2-(pyridin-2-yl)acetamide (20 mg, 0.052 mmol) in DMF (0.2 ml) were added 2-(pyridin-2-yl)acetic acid hydrochloride (18.16 mg, 0.105 mmol) and DIEA (0.037 ml, 0.209 mmol) and the resulting mixture was stirred at room temperature for 5 min until a clear yellow solution formed. The reaction was placed under $N_2$ and cooled in an ice bath. To this was added T3P (50% solution in EtOAc, 0.067 ml, 0.105 mmol) dropwise and the reaction was allowed to warm to room temperature overnight. The reaction was concentrated, mixed with saturated aq $NaHCO_3$, filtered, and the filter rinsed with water and DCM. The filtrate mixture containing the product was separated and the aqueous layer extracted twice with DCM. The DCM layers were combined and washed with saturated NaCl, dried over $MgSO_4$, filtered, concentrated, and the residue was adsorbed onto celite and purified via flash chromatography (0-20% of an 80/20/1 DCM/MeOH/$NH_4OH$ solution in DCM to give the title compound (2.5 mg, 9%) as a white solid. MS ($ES^+$) $C_{24}H_{23}N_9O_2S$ requires: 501, found: 502 $[M+H]^+$. $^1$H NMR (600 MHz, MeOD-$d_4$) δ: 8.50-8.56 (m, 2H), 8.18 (d, J=9.8 Hz, 1H), 7.78-7.82 (m, 2H), 7.42-7.46 (m, 2H), 7.28-7.36 (m, 2H), 6.94 (d, J=9.4 Hz, 1H), 4.00-4.09 (m, 4H), 3.97 (s, 2H), 3.81-3.86 (m, 1H), 3.73-3.80 (m, 1H), 3.62-3.69 (m, 1H), 2.56-2.66 (m, 1H), 2.36-2.40 (m, 1H).

Example 10: N-(pyridin-2-ylmethyl)-5-(1-(6-(2-(3-(trifluoromethoxy)phenyl)acetamido)pyridazin-3-yl)pyrrolidin-3-yl)-1,3,4-thiadiazole-2-carboxamide-2,2,2-trifluoroacetate

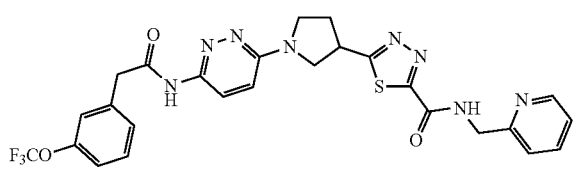 [SMILES: O=C(Cc1cccc(OC(F)(F)F)c1)Nc1ccc(N2CCC(c3nnc(C(=O)NCc4ccccn4)s3)C2)nn1]

Steps 1-4

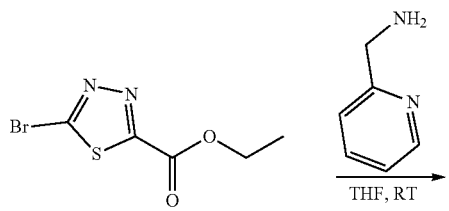

THF, RT

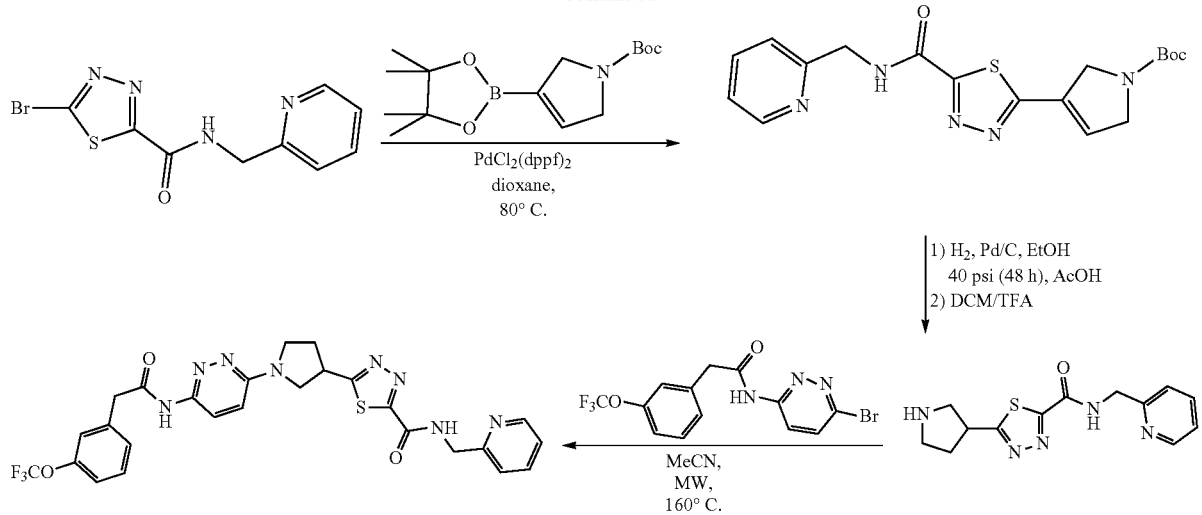

Step 1: 5-bromo-N-(pyridin-2-ylmethyl)-1,3,4-thiadiazole-2-carboxamide

To a suspension of ethyl 5-bromo-1,3,4-thiadiazole-2-carboxylate (483 mg, 2.037 mmol) was added pyridin-2-ylmethanamine (0.210 ml, 2.037 mmol) and the resulting mixture was stirred at room temperature overnight. The reaction was evaporated and the residue was purified via silica gel chromatography (25-100% EtOAc in hexanes, Rf=0.7 100% EtOAc) to give the title compound (300 mg, 49%) as a white solid. MS (ES$^+$) C$_9$H$_7$BrN$_4$OS requires: 299, found: 299, 301 [M+H]$^+$.

Step 2: Tert-butyl 3-(5-((pyridin-2-ylmethyl)carbamoyl)-1,3,4-thiadiazol-2-yl)-2,5-dihydro-1H-pyrrole-1-carboxylate A suspension of tert-butyl 3-(4,4,5,5-tetramethyl-1,3,2-dioxaborolan-2-yl)-2,5-dihydro-1H-pyrrole-1-carboxylate (296 mg, 1.003 mmol), 5-bromo-N-(pyridin-2-ylmethyl)-1,3,4-thiadiazole-2-carboxamide (300 mg, 1.003 mmol) and sodium carbonate 2M in water (1.5 ml, 3.01 mmol) under N$_2$ was treated with PdCl$_2$(dppf)-DCM (82 mg, 0.100 mmol) and heated to 90° C. and stirred for 2.5 hrs. The mixture was evaporated and the residue was purified via silica gel chromatography (0-100% EtOAc in hexanes to give the title compound (262 mg, 67%) as a yellow amorphous material. MS (ES$^+$) C$_{18}$H$_{22}$N$_5$O$_3$S requires: 387 found: 388 [M+H]$^+$.

Step 3: N-(pyridin-2-ylmethyl)-5-(pyrrolidin-3-yl)-1,3,4-thiadiazole-2-carboxamide To a solution of tert-butyl 3-(5-((pyridin-2-ylmethyl)carbamoyl)-1,3,4-thiadiazol-2-yl)-2,5-dihydro-1H-pyrrole-1-carboxylate (55 mg, 0.142 mmol) in Ethanol (1.5 ml) was added palladium on carbon (10%, 7.5 mg, 0.071 mmol) (after subjection to 3 iterations of vacuum and nitrogen) and the resulting mixture was subjected under 3 iterations of vacuum and nitrogen stirred followed by hydrogen (45 psi) in a Parr shaker for 6 hrs. The catalyst was filtered off and to the solution was added palladium on carbon (10%, 50 mg) and acetic acid (0.033 ml, 0.568 mmol). The reaction mixture was subjected to hydrogen (40 psi) in the Parr shaker for 48 hrs. The reaction was filtered through Celite and the filtrate was evaporated. The residue was directly dissolved in 1.6 ml of DCM and 0.4 ml of TFA and the mixture was stirred for 20 min. The reaction was evaporated and the residue dissolved in methanol and neutralized by elution with MeOH rinses through a MP-HCO$_3$ cartridge (Agilent PL3540-C603, PL-HCO3 MP SPE 500 mg/6 ml). The eluent was evaporated under vacuum to give the title compound as a yellow solid. MS (ES$^+$) C$_{13}$H$_{15}$N$_5$OS requires: 289 found: 290 [M+H]$^+$.

Step 4: N-(pyridin-2-ylmethyl)-5-(1-(6-(2-(3-(trifluoromethoxy)phenyl)acetamido)pyridazin-3-yl)pyrrolidin-3-yl)-1,3,4-thiadiazole-2-carboxamide 2,2,2-trifluoroacetate To a solution of N-(pyridin-2-ylmethyl)-5-(pyrrolidin-3-yl)-1,3,4-thiadiazole-2-carboxamide (7.05 mg, 0.024 mmol) in acetonitrile (0.5 ml) were added N-(6-bromopyridazin-3-yl)-2-(3-(trifluoromethoxy)phenyl)acetamide (11 mg, 0.029 mmol) and TEA (3.40 µl, 0.024 mmol) and the resulting mixture was heated in a microwave at 160° C. for 2 hrs. The mixture was filtered and purified by mass-triggered preparative HPLC (Mobile phase: A=0.1% TFA/H$_2$O, B=0.1% TFA/MeCN; Gradient: B=30-70%; 12 min; Column: C18) to give the title compound (0.94 mg, 1.346 µmol, 5%) as a brown solid. MS (ES$^+$) C$_{26}$H$_{23}$F$_3$N$_8$O$_3$S requires: 584 found: 585 [M+H]$^+$. $^1$H NMR (600 MHz, DMSO-d$_6$) δ: 11.10 (s, 1H), 9.75 (t, J=5.5 Hz, 1H), 8.57-8.52 (m, 1H), 8.21-8.15 (m, 1H), 7.86-7.81 (m, 1H), 7.58-7.18 (m, 6H), 7.26 (d, J=8.4 Hz, 1H), 4.63-4.59 (m, 2H), 4.30-4.23 (m, 1H), 4.11-4.05 (m, 1H), 3.90-3.84 (m, 1H), 3.82 (s, 2H), 3.75-3.61 (m, 2H), 2.66-2.59 (m, 1H), 2.38-2.30 (m, 1H).

Example 11: N-(6-(3-(4-acetamido-1H-1,2,3-triazol-1-yl)pyrrolidin-1-yl)pyridazin-3-yl)-2-(3-(trifluoromethoxy)phenyl)acetamide

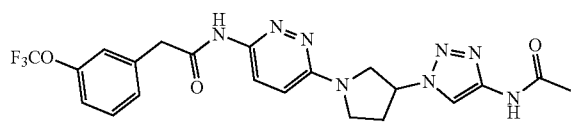 [SMILES: CC(=O)Nc1cn(C2CCN(c3ccc(NC(=O)Cc4cccc(OC(F)(F)F)c4)nn3)C2)nn1]

Steps 1-7

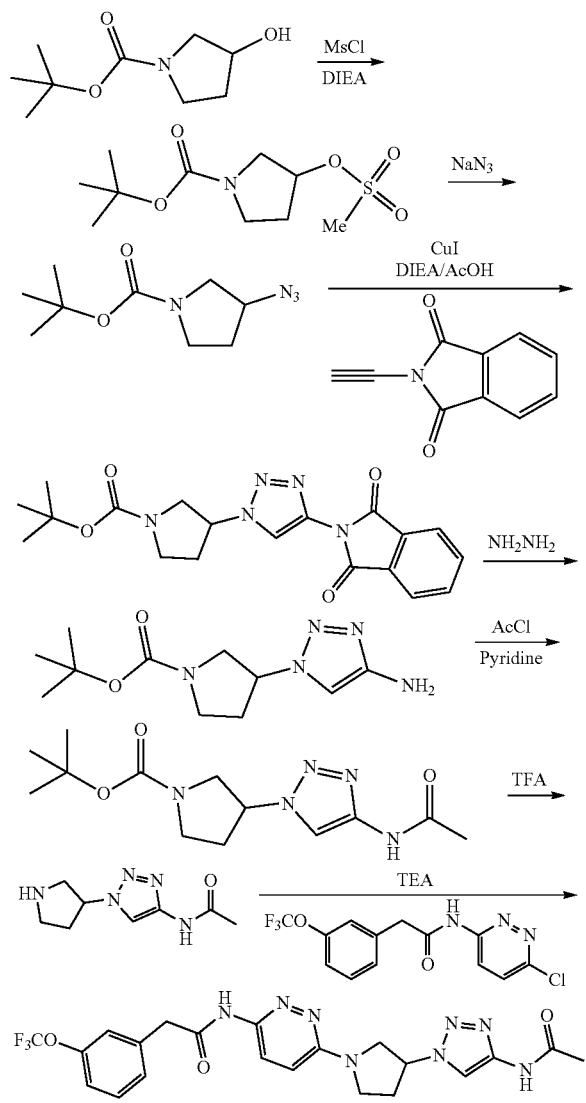

Step 1: Tert-butyl 3-((methylsulfonyl)oxy)pyrrolidine-1-carboxylate

A stirred solution of tert-butyl 3-hydroxypyrrolidine-1-carboxylate (2 g, 10.68 mmol) in DCM (93 ml) was cooled to 0° C. DIEA (3.73 ml, 21.36 mmol) was added followed by methanesulfonyl chloride (1.835 g, 16.02 mmol) under nitrogen. After 45 min, the reaction mixture was diluted with saturated sodium bicarbonate, extracted with DCM (3 times), washed with brine, dried over sodium sulfate, and concentrated to give the title compound (2.8 g, 99%) as a thick amber oil. MS (ES$^+$) $C_{10}H_{19}NO_5S$ requires: 265, found: 288 [M+Na]$^+$.

Step 2: Tert-butyl 3-azidopyrrolidine-1-carboxylate

To a stirring solution of tert-butyl 3-((methylsulfonyl)oxy)pyrrolidine-1-carboxylate (1.417 g, 5.34 mmol) in DMF (25 ml), sodium azide (0.694 g, 10.68 mmol) was added and the reaction was stirred at 40° C. for 19 hrs. The reaction mixture was concentrated under reduced pressure, saturated sodium bicarbonate and DCM (100 ml) were added, and the layers were separated. The aqueous phase was extracted with DCM (3×100 ml) and the organic layers were combined, washed with brine, dried over sodium sulfate, filtered, and concentrated under reduced pressure to give the title compound crude (1.8 g, 98% yield). MS (ES$^+$) $C_9H_{16}N_4O_2$ requires: 212, found: 235 [M+Na]$^+$.

Step 3: Tert-butyl 3-(4-(1,3-dioxoisoindolin-2-yl)-1H-1,2,3-triazol-1-yl)pyrrolidine-1-carboxylate To a solution of tert-butyl 3-azidopyrrolidine-1-carboxylate (500 mg, 2.356 mmol) in DCM (4.7 ml) were added 2-ethynylisoindoline-1,3-dione (484 mg, 2.83 mmol), DIEA (0.041 ml, 0.236 mmol), acetic acid (0.013 ml, 0.236 mmol), and copper (I) iodide (31.4 mg, 0.165 mmol) and the reaction was allowed to stir at room temperature for 16 hrs. The reaction mixture was filtered and the filtrate was concentrated and purified via silica gel chromatography (0-10% MeOH in DCM) to give the title compound (823 mg, 91%) as a white solid. MS (ES$^+$) $C_{19}H_{21}N_5O_4$ requires: 383, found: 384 [M+H]$^+$.

Step 4: Tert-butyl 3-(4-amino-1H-1,2,3-triazol-1-yl)pyrrolidine-1-carboxylate

To a stirring solution of tert-butyl 3-(4-(1,3-dioxoisoindolin-2-yl)-1H-1,2,3-triazol-1-yl)pyrrolidine-1-carboxylate (617.7 mg, 1.611 mmol) in MeOH (16 ml) was added hydrazine hydrate (0.157 ml, 3.22 mmol) and the reaction was heated at 80° C. until completion. The reaction mixture was concentrated, diluted with MeOH, and acidified with TFA added dropwise. The resulting white solid was filtered off and the filtrate was diluted with water and lyophilized to give the title compound (500 mg, 73%) as an off-white semi-solid. MS (ES$^+$) $C_{11}H_{19}N_5O_2$ requires: 253, found: 254 [M+H]$^+$.

Step 5: Tert-butyl 3-(4-acetamido-1H-1,2,3-triazol-1-yl)pyrrolidine-1-carboxylate To a stirred solution of tert-butyl 3-(4-amino-1H-1,2,3-triazol-1-yl)pyrrolidine-1-carboxylate (100 mg, 0.395 mmol) in DMF (2 ml) was added pyridine (0.064 ml, 0.790 mmol) and the reaction was cooled in an ice bath. To the reaction was added acetyl chloride (0.056 ml, 0.790 mmol) and the reaction mixture was allowed to warm to room temperature over 20 hrs. The reaction mixture was concentrated, diluted with DCM, and washed with water (3×), saturated sodium bicarbonate (3×) and brine. The organic layer was dried over magnesium sulfate, and concentrated to give the title compound (54.5 mg, 46.7%) as an off-white solid. MS (ES$^+$) $C_{13}H_{21}N_5O_3$ requires: 295, found: 318 [M+Na]$^+$.

Step 6: N-(1-(Pyrrolidin-3-yl)-1H-1,2,3-triazol-4-yl)acetamide

To a stirred solution of tert-butyl 3-(4-acetamido-1H-1,2,3-triazol-1-yl)pyrrolidine-1-carboxylate (54.5 mg, 0.185 mmol) in DCM (0.923 ml), was added TFA (0.284 ml, 3.69 mmol) dropwise, and the reaction allowed to stir for 3 hrs. The reaction mixture was concentrated to give the title compound (51 mg, 90%) as a pale yellow solid. MS (ES+) C8H13N5O requires: 195, found: 196 [M+H]+.

Step 7: N-(6-(3-(4-Acetamido-1H-1,2,3-triazol-1-yl)pyrrolidin-1-yl)pyridazin-3-yl)-2-(3-(trifluoromethoxy)phenyl)acetamide To a vial containing N-(6-chloropyridazin-3-yl)-2-(3-(trifluoromethoxy)phenyl)acetamide (20 mg, 0.060 mmol), N-(1-(pyrrolidin-3-yl)-1H-1,2,3-triazol-4-yl)acetamide (11.77 mg, 0.060 mmol), and TEA (84 µl, 0.603 mmol) was stirred and heated at 100° C. for 48 hrs. The reaction was diluted with MeOH/DMSO, acidified with TFA, and purified by mass-triggered preparative HPLC (Mobile phase: A=0.1% TFA/H2O, B=0.1% TFA/MeCN; Gradient: B=20-50%; 12 min; Column: C18) to give the title compound as a yellow powder. MS (ES+) C21H21F3N8O3 requires: 490 found: 491 [M+H]+. 1H NMR (600 MHz, DMSO-d6) δ: 10.97 (brs, 1H), 10.86 (s, 1H), 8.20 (s, 1H), 8.06 (brs, 1H), 7.40-7.49 (m, 1H), 7.33-7.39 (m, 2H), 7.18-7.30 (m, 2H), 5.42 (brs, 1H), 3.89-4.05 (m, 2H), 3.80 (s, 2H), 3.61-3.70 (m, 2H), 2.57-2.65 (m, 2H), 2.03 (s, 3H).

Example 12: N-(6-(3-(5-acetamido-1,3,4-thiadiazol-2-yl)pyrrolidin-1-yl)pyridazin-3-yl)-2-(pyridin-2-yl)acetamide

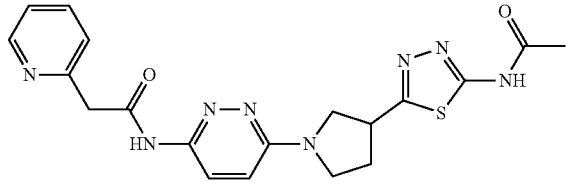 [SMILES: CC(=O)Nc1nnc(C2CCN(c3ccc(NC(=O)Cc4ccccn4)nn3)C2)s1]

The title compound was synthesized by a similar procedure to that used for Example 14. MS (ES+) C19H20N8O2S requires: 424, found: 425 [M+H]+.

Example 14: 2-(pyridin-2-yl)-N-(5-(1-(6-(2-(3-(trifluoromethoxy)phenyl)acetamido)pyridazin-3-yl)piperidin-3-yl)-1,3,4-thiadiazol-2-yl)acetamide

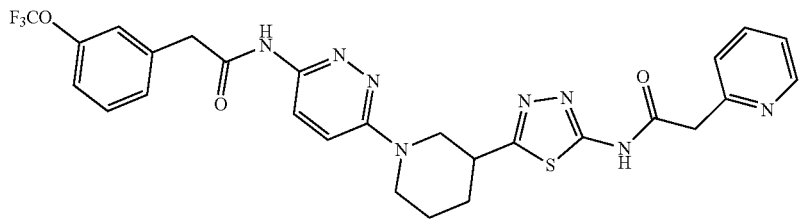 [SMILES: O=C(Cc1cccc(OC(F)(F)F)c1)Nc1ccc(N2CCCC(c3nnc(NC(=O)Cc4ccccn4)s3)C2)nn1]

Steps 1-4

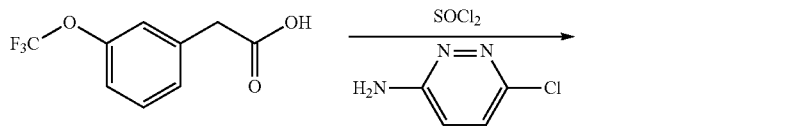

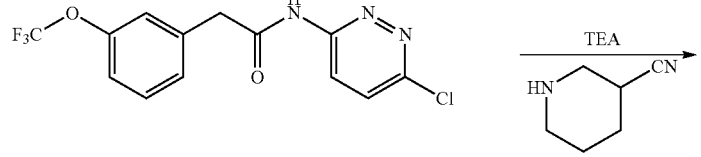

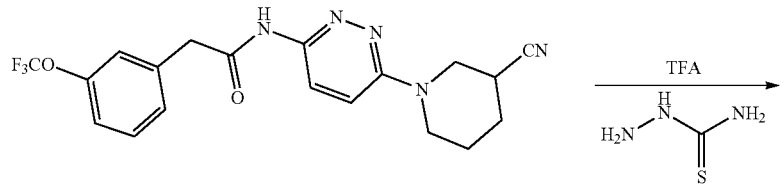

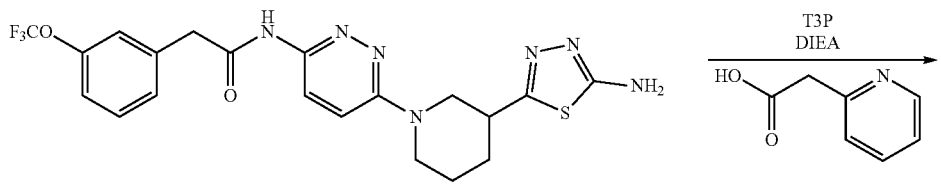

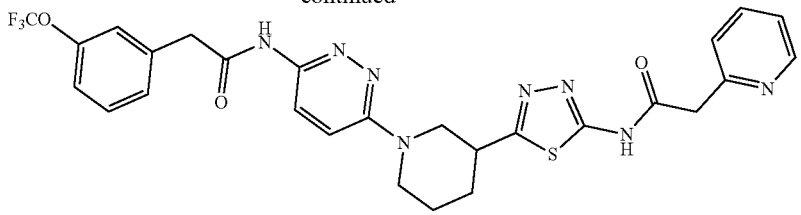

Step 1: N-(6-chloropyridazin-3-yl)-2-(3-(trifluoromethoxy)phenyl)acetamide

To a round bottom flask containing 2-(3-(trifluoromethoxy)phenyl)acetic acid (13.59 g, 61.8 mmol) was added thionyl chloride (9.01 ml, 124 mmol) and the reaction was stirred at room temperature overnight. The reaction was concentrated and then azeotroped with mixtures of DCM/toluene and then DCM/hexanes. In a round bottom flask containing 6-chloropyridazin-3-amine (4 g, 30.9 mmol) mixed with NMP (50 ml) was added dropwise via addition funnel 2-(3-(trifluoromethoxy)phenyl)acetyl chloride (7.37 g, 30.9 mmol) dissolved in NMP (10 ml). Reaction was stirred at room temperature overnight. The reaction was then heated at 50° C. for 3.5 hrs. The reaction mixture was dripped into a solution of saturated NaHCO$_3$ (200 ml) and ice. The mixture was transferred to a larger flask, diluted with more saturated NaHCO$_3$ and water and stirred until all of the ice melted and mixture warmed to room temperature. The solid was filtered off and washed with saturated NaHCO$_3$, water, and hexanes, to give the title compound (6.24 g, 61%) as an off white solid. MS (ES$^+$) C$_{13}$H$_9$ClF$_3$N$_3$O$_2$ requires: 331, found: 332 [M+H]$^+$.

Step 2: N-(6-(3-cyanopiperidin-1-yl)pyridazin-3-yl)-2-(3-(trifluoromethoxy)phenyl)acetamide In a vial was added N-(6-chloropyridazin-3-yl)-2-phenylacetamide (2 g, 6.03 mmol) piperidine-3-carbonitrile (0.731 g, 6.63 mmol), and TEA (1 ml, 7.24 mmol) and the reaction was stirred and heated in sand bath at 100° C. overnight. The reaction was then heated in a microwave reactor for 2.5 hr at 150° C. To the reaction was added piperidine-3-carbonitrile (0.44 g, 4.0 mmol) and TEA (0.5 ml, 3.6 mmol) and was heated in dry block at 120° C. overnight. The reaction was diluted with DCM and saturated NaHCO$_3$, the phases separated, and the DCM layer was washed with water and brine. Each aqueous layer was extracted twice with DCM. The organic layers were combined, dried over MgSO$_4$, filtered, concentrated and the residue was dissolved in minimal DCM and purified via silica gel chromatography (0-100% EtOAc in hexanes) to give the title compound (397 mg, 16%) as a pale yellow solid. MS (ES$^+$) C$_{19}$H$_{18}$F$_3$N$_5$O$_2$ requires: 405, found: 406 [M+H]$^+$.

Step 3: Example 13: N-(6-(3-(5-amino-1,3,4-thiadiazol-2-yl)piperidin-1-yl)pyridazin-3-yl)-2-(3-(trifluoromethoxy)phenyl)acetamide In a round bottom flask containing N-(6-(3-cyanopiperidin-1-yl)pyridazin-3-yl)-2-(3-(trifluoromethoxy)phenyl)acetamide (396 mg, 0.977 mmol) was added TFA (2 ml, 26 mmol) and hydrazinecarbothioamide (116 mg, 1.28 mmol). The reaction was heated in a dry block at 80° C. for 30 min (cooled to room temperature overnight) and 60° C. for 4 hr, then cooled to room temperature over 2 days. The reaction was heated to 80° C. for 30 min and then cooled to room temperature, diluted with EtOH and concentrated. The thick oil was concentrated from DCM/hexanes, and the residue was adsorbed onto celite and purified via flash chromatography (0-50% of an 80/20/1 DCM/MeOH/NH$_4$OH solution in DCM) to give the title compound (381 mg, 81%) as a yellow solid. MS (ES$^+$) C$_{20}$H$_{20}$F$_3$N$_7$O$_2$S requires: 479, found: 480 [M+H]$^+$.

Step 4: 2-(pyridin-2-yl)-N-(5-(1-(6-(2-(3-(trifluoromethoxy)phenyl)acetamido)pyridazin-3-yl)piperidin-3-yl)-1,3,4-thiadiazol-2-yl)acetamide To a vial containing N-(6-(3-(5-amino-1,3,4-thiadiazol-2-yl)piperidin-1-yl)pyridazin-3-yl)-2-(3-(trifluoromethoxy)phenyl)acetamide, DIEA (146 μl, 0.834 mmol) and 2-(pyridin-2-yl)acetic acid hydrochloride (72.4 mg, 0.417 mmol) dissolved in DMF (2 ml) was placed under nitrogen and cooled in an ice bath. To this mixture was added T3P (50% solution in DMF, 131 μl, 0.417 mmol) dropwise. The reaction was allowed to warm to room temperature over 4.5 hrs. The reaction was diluted with MeOH and water and the yellow solution was concentrated to a thick oil. The residue was adsorbed onto silica gel and purified via flash chromatography (Hexanes, then 0-50% of an 80/20/1 DCM/MeOH/NH$_4$OH solution in DCM) to give the title compound (64.9 mg, 52.0%) as a yellow solid. MS (ES$^+$) C$_{27}$H$_{25}$F$_3$N$_8$O$_3$S requires: 598, found: 599 [M+H]$^+$. $^1$H NMR (600 MHz, DMSO-d$_6$) δ: 12.73 (s, 1H), 10.97 (s, 1H), 8.49 (dd, J=4.9, 0.8 Hz, 1H), 8.00 (d, J=9.8 Hz, 1H), 7.77 (t d, J=7.6, 1.7 Hz, 1H), 7.44-7.49 (m, 1H), 7.33-7.44 (m, 4H), 7.23-7.31 (m, 2H), 4.43 (br d, J=11.0 Hz, 1H), 3.97-4.08 (m, 3H), 3.80 (s, 2H), 3.33-3.38 (m, 2H), 3.11-3.21 (m, 1H), 2.12-2.20 (m, 1H), 1.74-1.89 (m, 2H), 1.54-1.69 (m, 1H).

Example 15: N-(6-(3-(5-acetamido-1,3,4-thiadiazol-2-yl)piperidin-1-yl)pyridazin-3-yl)-2-(3-(trifluoromethoxy)phenyl)acetamide

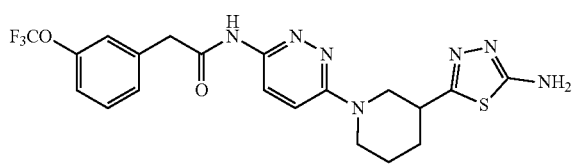 [SMILES: Nc1nnc(C2CCCN(c3ccc(NC(=O)Cc4cccc(OC(F)(F)F)c4)nn3)C2)s1]

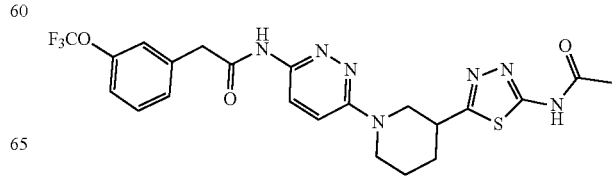

The title compound was synthesized by a similar procedure to Example 14. MS (ES+) $C_{22}H_{22}F_3N_7O_3S$ requires: 521, found: 522 [M+H]+.

Example 17: 2-(pyridin-2-yl)-N-(5-(1-(6-(2-(3-(trifluoromethoxy)phenyl)acetamido)pyridazin-3-yl)pyrrolidin-3-yl)-1,3,4-thiadiazol-2-yl)acetamide 2,2,2-trifluoroacetate

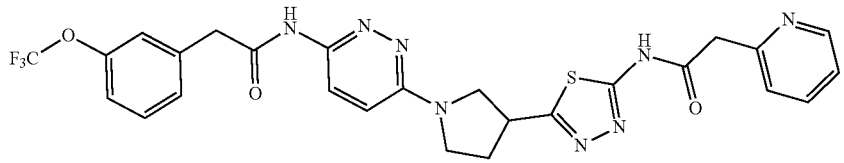 [SMILES: O=C(Cc1cccc(OC(F)(F)F)c1)Nc1ccc(N2CCC(c3nnc(NC(=O)Cc4ccccn4)s3)C2)nn1]

Steps 1-3

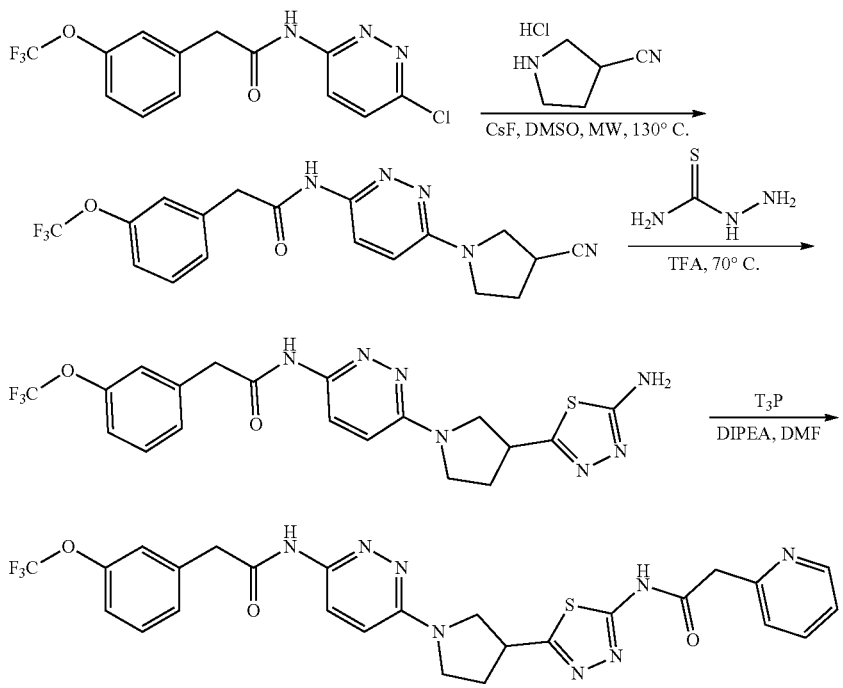

Step 1: N-(6-(3-cyanopyrrolidin-1-yl)pyridazin-3-yl)-2-(3-(trifluoromethoxy)phenyl)acetamide A microwave vial was charged with N-(6-chloropyridazin-3-yl)-2-(3-(trifluoromethoxy)phenyl)acetamide (1000 mg, 3.01 mmol), pyrrolidine-3-carbonitrile hydrochloride (600 mg, 4.52 mmol), cesium fluoride (458 mg, 3.01 mmol) and DMSO (4 ml) was added. The vial was sealed and the reaction mixture was heated to 130° C. in a microwave reactor for 6 hrs (60% conversion). The mixture was evaporated and taken up in EtOAc washed with saturated NaHCO₃ and brine and dried over Na₂SO₄. The residue was purified via silica gel chromatography (0-100% EtOAc in DCM to give the title compound (240 mg, 20%) as a green solid. MS (ES+) $C_{18}H_{16}F_3N_5O_2$ requires: 391, found: 392 [M+H]+.

Step 2: Example 19: N-(6-(3-(5-amino-1,3,4-thiadiazol-2-yl)pyrrolidin-1-yl)pyridazin-3-yl)-2-(3-(trifluoromethoxy)phenyl)acetamide

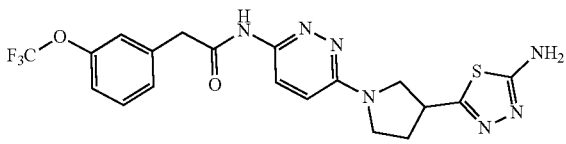 [SMILES: Nc1nnc(C2CCN(c3ccc(NC(=O)Cc4cccc(OC(F)(F)F)c4)nn3)C2)s1]

To a solution of N-(6-(3-cyanopyrrolidin-1-yl)pyridazin-3-yl)-2-(3-(trifluoromethoxy)phenyl)acetamide (240 mg, 0.613 mmol) in TFA (1 ml) were added hydrazinecarbothioamide (6 1.5 mg, 0.675 mmol) and the resulting mixture was stirred at 70° C. for 6 hrs. The mixture was evaporated and dissolved in DCM containing methanol (10-15%) and then washed with 1:1 mixture saturated NaHCO₃:H₂O. The aqueous phase was then washed with DCM and all the organic phases were combined and evaporated in vacuo. The residue was purified via silica gel chromatography (0-7% MeOH in DCM and then isocratic 7% of methanol in DCM) to give the title compound (182 mg, 64%) as a yellow solid. MS (ES$^+$) $C_{18}H_{16}F_3N_5O_2S$ requires: 465, found: 466 [M+H]$^+$.

Step 3: 2-(pyridin-2-yl)-N-(5-(1-(6-(2-(3(trifluoromethoxy)phenyl)acetamido)pyridazin-3-yl)pyrrolidin-3-yl)-1,3,4-thiadiazol-2-yl)acetamide 2,2,2-trifluoroacetate To a solution of N-(6-(3-(5-amino-1,3,4-thiadiazol-2-yl)pyrrolidin-1-yl)pyridazin-3-yl)-2-(3-(trifluoromethoxy)phenyl)acetamide (40 mg, 0.086 mmol) in DMF (0.5 ml) were added 2-(pyridin-2-yl)acetic acid hydrochloride (44.8 mg, 0.258 mmol) and DIEA (0.090 ml, 0.516 mmol) at 0° C., then T3P (50% DMF, 0.149 ml, 0.258 mmol) and the mixture was allowed to reach room temperature. After 3 hr the mixture was diluted with water and extracted with DCM/MeOH (10-15%). The organic phase was evaporated, redissolved in DMSO, acidified with aq HCl (6N, few drops) and purified by mass-triggered preparative HPLC (Mobile phase: A=0.1% TFA/H$_2$O, B=0.1% TFA/MeCN; Gradient: B=20-60%; 20 min; Column: C18) to give the title compound (23 mg, 0.033 mmol, 38% yield) as a pale yellow solid. MS (ES$^+$) $C_{26}H_{23}F_3N_8O_3S$ requires: 584, found: 585 [M+H]$^+$. $^1$H NMR (600 MHz, d$_6$-DMSO) δ: 12.82 (s, 1H), 11.13 (brs, 1H), 8.53 (d, J=4.6 Hz, 1H), 8.21 (br d, J=5.8 Hz, 1H), 7.86 (t, J=7.6 Hz, 1H), 7.49-7.43 (m, 3H), 7.38-7.33 (m, 3H), 7.26 (d, J=7.4 Hz, 1H), 4.12-4.06 (m, 1H), 4.06 (s, 2H), 4.05-3.99 (m, 1H), 3.87-3.82 (m, 1H), 3.82 (s, 2H), 3.74-3.68 (m, 1H), 3.67-3.61 (m, 1H), 2.59-2.51 (m, 1H), 2.35-2.26 (m, 1H).

Example 18: IACS-005992 2-(1-methyl-1H-pyrazol-4-yl)-N-(5-(1-(6-(2-(3-(trifluoromethoxy)phenyl)acetamido)pyridazin-3-yl)pyrrolidin-3-yl)-1,3,4-thiadiazol-2-yl)acetamide 2,2,2-trifluoroacetate

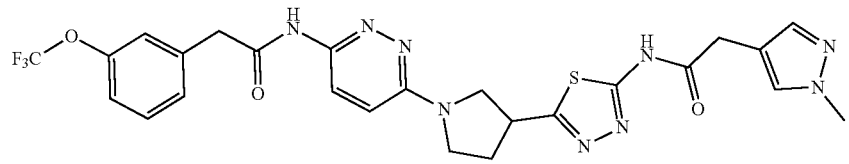 [SMILES: Cn1cc(CC(=O)Nc2nnc(C3CCN(c4ccc(NC(=O)Cc5cccc(OC(F)(F)F)c5)nn4)C3)s2)cn1]

The compound was prepared by the procedure of Example 20, 2-(2-fluorophenyl)-N-(5-(1-(6-(2-(3-(trifluoromethoxy)phenyl)acetamido)pyridazin-3-yl)pyrrolidin-3-yl)-1,3,4-thiadiazol-2-yl)acetamide 2,2,2-trifluoroacetate. The residue was purified by mass-triggered preparative HPLC (Mobile phase: A=0.1% TFA/H$_2$O, B=0.1% TFA/MeCN; Gradient: B=20-60%; 20 min; Column: C18) to give the title compound (8 mg, 26%) as a pale yellow solid. MS (ES+) $C_{25}H_{24}F_3N_9O_3S$ requires: 587, found: 588 [M+H]$^+$.

Example 20: 2-(2-fluorophenyl)-N-(5-(1-(6-(2-(3-(trifluoromethoxy)phenyl)acetamido)pyridazin-3-yl) pyrrolidin-3-yl)-1,3,4-thiadiazol-2-yl)acetamide 2,2,2-trifluoroacetate

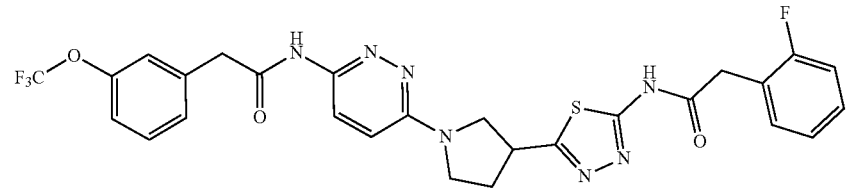 [SMILES: O=C(Cc1cccc(OC(F)(F)F)c1)Nc1ccc(N2CCC(c3nnc(NC(=O)Cc4ccccc4F)s3)C2)nn1]

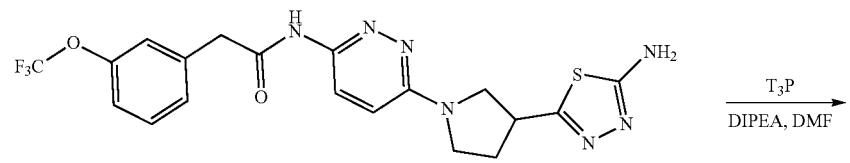

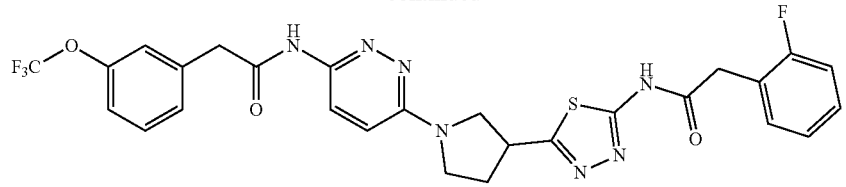

To a solution of N-(6-(3-(5-amino-1,3,4-thiadiazol-2-yl)pyrrolidin-1-yl)pyridazin-3-yl)-2-(3-(trifluoromethoxy)phenyl)acetamide (15 mg, 0.032 mmol) in DMF (0.5 ml) were added 2-(2-fluorophenyl)acetic acid (14.90 mg, 0.097 mmol) and DIEA (0.034 ml, 0.193 mmol) at 0° C., then T3P (50% DMF, 0.056 ml, 0.097 mmol), and the mixture was allowed to reach room temperature over 30 min. The reaction was concentrated and purified by mass-triggered preparative HPLC (Mobile phase: A=0.1% TFA/H$_2$O, B=0.1% TFA/MeCN; Gradient: B=30-70%; 20 min; Column: C18) to give the title compound (10 mg, 43%) as a pale yellow solid. MS (ES$^+$) $C_{27}H_{23}F_4N_7O_3S$ requires: 601, found: 602 [M+H]$^+$ $^1$H NMR (600 MHz, DMSO-d$_6$) δ: 12.79 (s, 1H), 11.00 (brs, 1H), 8.06 (brs, 1H), 7.46 (t, J=7.9 Hz, 1H), 7.40-7.30 (m, 4H), 7.26 (d, J=8.2 Hz, 1H), 7.24-7.03 (m, 3H), 4.07-4.01 (m, 1H), 3.98-3.91 (m, 1H), 3.89 (s, 2H), 3.80 (s, 2H), 3.79-3.73 (m, 2H), 3.68-3.52 (m, 1H), 2.35-2.48 (m, 1H), 2.29-2.22 (m, 1H).

Example 21: 2-(pyridin-2-yl)-N-(5-(3-(6-(2-(3-(trifluoromethoxy)phenyl)acetamido)pyridazin-3-yl)pyrrolidin-1-yl)-1,3,4-thiadiazol-2-yl)acetamide

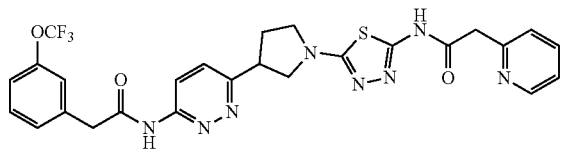 [SMILES: O=C(Cc1cccc(OC(F)(F)F)c1)Nc1ccc(C2CCN(c3nnc(NC(=O)Cc4ccccn4)s3)C2)nn1]

Steps 1-2

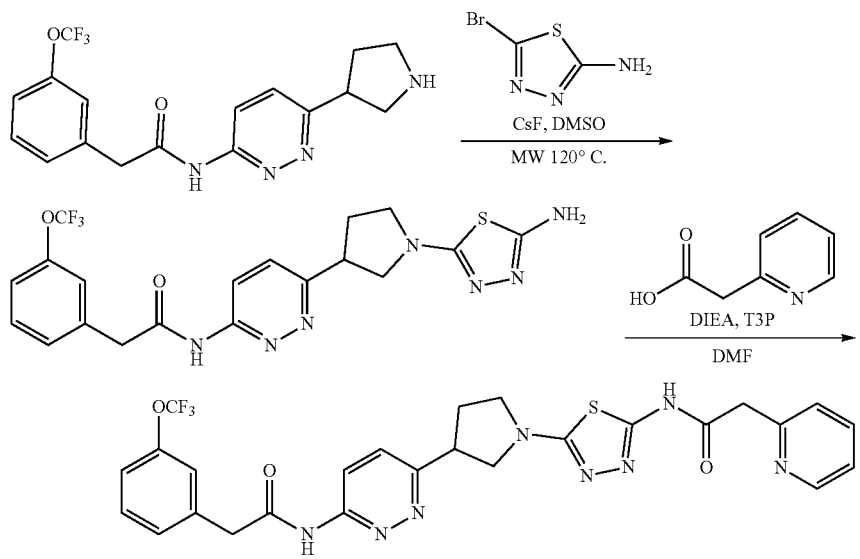

Step 1: N-(6-(1-(5-amino-1,3,4-thiadiazol-2-yl)pyrrolidin-3-yl)pyridazin-3-yl)-2-(3-(trifluoromethoxy)phenyl)acetamide The compound was prepared by the procedure of Example 22, Step 5. The mixture was taken up in EtOAc and washed with water. The combined organic layers were washed with saturated NaCl, dried over Na$_2$SO$_4$, filtered and concentrated under reduced pressure to give the title compound (used directly for the next step). MS (ES$^+$) $C_{19}H_{18}F_3N_7O_2S$ requires: 465, found: 466 [M+H]$^+$.

Step 2: 2-(pyridin-2-yl)-N-(5-(3-(6-(2-(3-(trifluoromethoxy)phenyl)acetamido)pyridazin-3-yl)pyrrolidin-1-yl)-1,3,4-thiadiazol-2-yl)acetamide To a solution of N-(6-(1-(5-amino-1,3,4-thiadiazol-2-yl)pyrrolidin-3-yl)pyridazin-3-yl)-2-(3-(trifluoromethoxy)phenyl)acetamide (20 mg, 0.043 mmol) in DMF (0.5 ml) were added 2-(pyridin-2-yl)acetic acid hydrochloride (22.38 mg, 0.129 mmol) and DIEA (0.045 ml, 0.258 mmol) and cooled in an ice bath. To the reaction was added T3P (50% solution in DMF, 0.075 ml, 0.129 mmol) and the mixture was allowed to reach RT. Upon completion the volatiles were removed under reduced pressure and the residue was purified by mass-triggered preparative HPLC (Mobile phase: A=0.1% TFA/H$_2$O, B=0.1% TFA/MeCN; Gradient: B=40-60%; 20 min; Column: C18) to give the title compound (2.4 mg, 9%). MS (ES$^+$) $C_{26}H_{23}F_3N_8O_3S$ requires: 584, found: 585 [M+H]$^+$. $^1$H NMR (600 MHz, DMSO-d$_6$) δ 12.44 (brs, 1H), 11.37 (s, 1H), 8.60 (d, J=4.4 Hz, 1H), 8.25 (d, J=9.2 Hz, 1H), 8.01-7.94 (m, 1H), 7.71 (d, J=9.2 Hz, 1H), 7.55 (d, J=7.3 Hz, 1H), 7.50-7.43 (m, 2H), 7.40-7.34 (m, 2H), 7.26 (d, J=8.2 Hz, 1H), 4.05 (s, 2H), 3.93-3.80 (m, 2H), 3.86 (s, 2H), 3.72-3.65 (m, 1H), 3.65-3.58, (m, 1H), 3.58-3.51 (m, 1H), 2.52-2.44 (m, 1H), 2.30-2.22 (m, 1H).

Example 22: N-(pyridin-2-ylmethyl)-5-(3-(6-(2-(3-(trifluoromethoxy)phenyl)acetamido)pyridazin-3-yl) pyrrolidin-1-yl)-1,3,4-thiadiazole-2-carboxamide

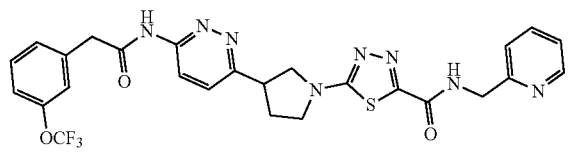 [SMILES: O=C(Cc1cccc(OC(F)(F)F)c1)Nc1ccc(C2CCN(c3nnc(C(=O)NCc4ccccn4)s3)C2)nn1]

Step 1-5

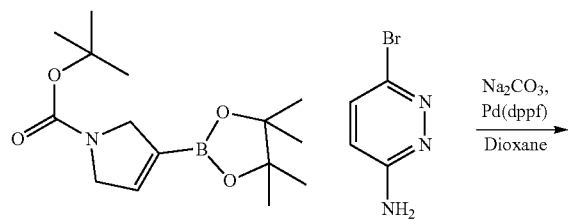

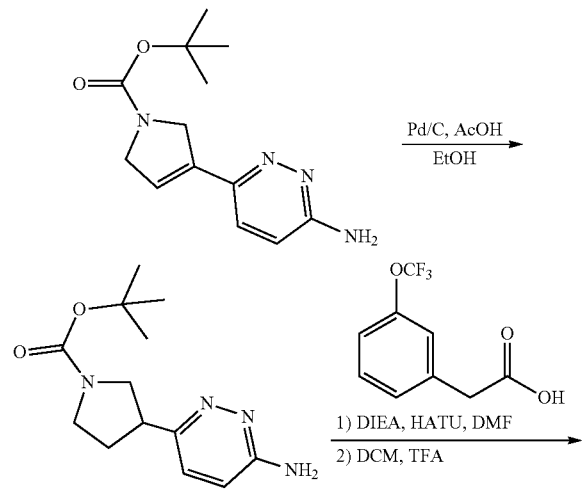

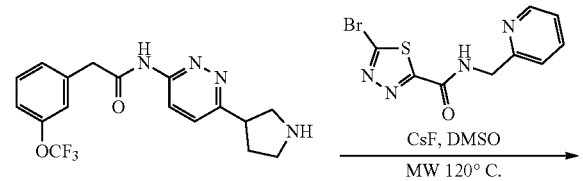

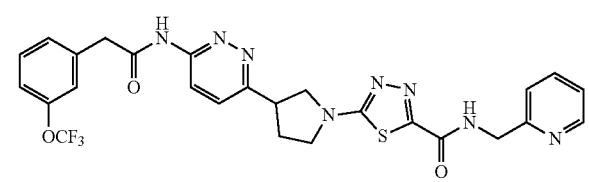

Step 1: Tert-butyl 3-(6-aminopyridazin-3-yl)-2,5-dihydro-1H-pyrrole-1-carboxylate A suspension of tert-butyl 3-(4,4,5,5-tetramethyl-1,3,2-dioxaborolan-2-yl)-2,5-dihydro-1H-pyrrole-1-carboxylate (500 mg, 1.694 mmol), 6-bromopyridazin-3-amine (246 mg, 1.412 mmol) and 2M sodium carbonate (2.117 ml, 4.23 mmol) was treated with $PdCl_2$(dppf)-DCM adduct (115 mg, 0.141 mmol), stirred and heated to 90° C. for 2.5 hrs. The volatiles were removed under reduced pressure and the residue was purified via silica gel chromatography (0-10% MeOH in DCM) to give the title compound (263 mg, 71%). MS (ES$^+$) $C_{13}H_{18}N_4O_2$ requires: 262, found: 263 [M+H]$^+$.

Step 2: Tert-butyl 3-(6-aminopyridazin-3-yl)pyrrolidine-1-carboxylate

A reaction vessel was charged with tert-butyl 3-(6-aminopyridazin-3-yl)-2,5-dihydro-1H-pyrrole-1-carboxylate (263 mg, 1.003 mmol), acetic acid (0.115 ml, 2.005 mmol) and ethanol (3.0 ml) under an atmosphere of nitrogen. The suspension was degassed with nitrogen and purged with hydrogen (3×). The reaction mixture was subjected to hydrogen at 40 psi for 48 hr in a Parr shaker. The reaction mixture was purged with nitrogen and filtered through Celite. The filtrate was concentrated under reduced pressure. The residue was purified via silica gel chromatography (0-10% MeOH in DCM) to give the title compound (140 mg, 52%) as an off-white amorphous material. MS (ES$^+$) $C_{13}H_{20}N_4O_2$ requires: 264, found: 265 [M+H]$^+$.

Step 3: Tert-butyl 3-(6-(2-(3-(trifluoromethoxy) phenyl)acetamido)pyridazin-3-yl)pyrrolidine-1-carboxylate To a solution of tert-butyl 3-(6-aminopyridazin-3-yl)pyrrolidine-1-carboxylate (70 mg, 0.265 mmol) in DMF (1 ml) were added 2-(3-(trifluoromethoxy)phenyl)acetic acid (117 mg, 0.530 mmol), HATU (151 mg, 0.397 mmol) and DIEA (0.185 ml, 1.059 mmol) and the resulting mixture was stirred at RT overnight. The volatiles were removed under reduced pressure. The residue was taken up in EtOAc and washed with water. The aqueous phase was extracted and the combined organic layers were concentrated under reduced pressure. The residue was purified via silica gel chromatography (0-20% MeOH in DCM) to give the title compound as an orange solid which was used as such in the next step. MS (ES$^+$) $C_{22}H_{25}F_3N_4O_4$ requires: 466, found: 467 [M+H]$^+$.

Step 4: N-(6-(pyrrolidin-3-yl)pyridazin-3-yl)-2-(3-(trifluoromethoxy)phenyl)acetamide A solution of tert-butyl 3-(6-(2-(3-(trifluoromethoxy)phenyl)acetamido)pyridazin-3-yl)pyrrolidine-1-carboxylate in DCM (0.8 ml) was treated with TFA (0.2 ml) and stirred for 1 hr. The volatiles were removed under reduced pressure. The residue was dissolved in MeOH and neutralized using an MP-HCO$_3$ cartridge. The eluent was concentrated under reduced pressure to give the title compound (100 mg, 100%). MS (ES$^+$) $C_{17}H_{17}F_3N_4O_2$ requires: 366, found: 367 [M+H]$^+$.

Step 5: N-(pyridin-2-ylmethyl)-5-(3-(6-(2-(3-(trifluoromethoxy)phenyl)acetamido)pyridazin-3-yl) pyrrolidin-1-yl)-1,3,4-thiadiazole-2-carboxamide A microwave vial was charged with N-(6-(pyrrolidin-3-yl)pyridazin-3-yl)-2-(3-(trifluoromethoxy)phenyl)acetamide (15 mg, 0.041 mmol), 5-bromo-N-(pyridin-2-ylmethyl)-1,3,4-thiadiazole-2-carboxamide (12.25 mg, 0.041 mmol) (synthesized by a similar procedure as 5-Bromo-N-(3-(trifluoromethoxy)benzyl)-1,3,4-thiadiazole-2-carboxamide), CsF (6.22 mg, 0.041 mmol) and DMSO (0.25 ml). The vial was sealed and the reaction mixture was heated in the microwave at 120° C. for 20 min. The mixture was purified by mass-triggered preparative HPLC (Mobile phase: A=0.1% TFA/H$_2$O, B=0.1% TFA/MeCN; Gradient: B=30-70%; 20 min; Column: C18) to give the title compound (2.6 mg, 10%) as a pale yellow amorphous material. MS (ES$^+$) C$_{26}$H$_{23}$F$_3$N$_8$O$_3$S requires: 584, found: 585 [M+H]$^+$. $^1$H NMR (600 MHz, DMSO-d$_6$) δ 11.38 (s, 1H), 9.43 (t, J=6.0 Hz, 1H), 8.65 (d, J=4.8 Hz, 1H), 8.26 (d, J=9.3 Hz, 1H), 8.09 (t, J=7.6 Hz, 1H), 7.73 (d, J=9.2 Hz, 1H), 7.59 (d, J=7.9 Hz, 1H), 7.56 (t, J=6.1 Hz, 1H), 7.47 (t, J=7.9 Hz, 1H), 7.40-7.35 (m, 2H), 7.26 (d, J=7.6 Hz, 1H), 4.65 (d, J=6.1 Hz, 2H), 4.03-3.97 (m, 1H), 3.97-3.90 (m, 1H), 3.87 (s, 2H), 3.82-3.77 (m, 1H), 3.73-3.67 (m, 1H), 3.67-3.61 (m, 1H), 2.55-2.50 (m, 1H), 2.35-2.27 (m, 1H).

Example 23: 2-(2-fluorophenyl)-N-(5-(1-(6-(2-(3-(trifluoromethoxy)phenyl)acetamido)pyridazin-3-yl)piperidin-3-yl)-1,3,4-thiadiazol-2-yl)acetamide

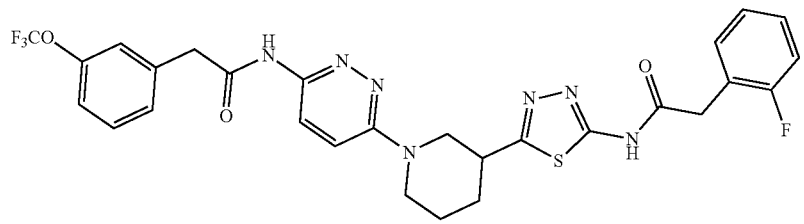 [SMILES: O=C(Cc1cccc(OC(F)(F)F)c1)Nc1ccc(N2CCCC(c3nnc(NC(=O)Cc4ccccc4F)s3)C2)nn1]

The title compound was synthesized by a similar procedure to Example 14. MS (ES$^+$) C$_{28}$H$_{25}$F$_4$N$_7$O$_3$S requires: 615, found: 616 [M+H]$^+$. $^1$H NMR (600 MHz, DMSO-d$_6$) δ: 12.75 (brs, 1H), 10.97 (s, 1H), 8.00 (d, J=9.8 Hz, 1H), 7.44-7.50 (m, 1H), 7.31-7.43 (m, 5H), 7.25 (d, J=7.9 Hz, 1H), 7.15-7.21 (m, 2H), 4.43 (d, J=11.0 Hz, 1H), 4.03 (d, J=12.8 Hz, 1H), 3.89 (s, 2H), 3.79 (s, 2H), 3.36-3.45 (m, 1H), 3.12-3.21 (m, 1H), 2.53-2.60 (m, 1H), 2.10-2.21 (m, 1H), 1.73-1.90 (m, 2H), 1.57-1.69 (m, 1H).

Example 24: 2-(1-Methyl-1H-pyrazol-4-yl)-N-(5-(1-(6-(2-(3-(trifluoromethoxy)phenyl)acetamido)pyridazin-3-yl)piperidin-3-yl)-1,3,4-thiadiazol-2-yl)acetamide

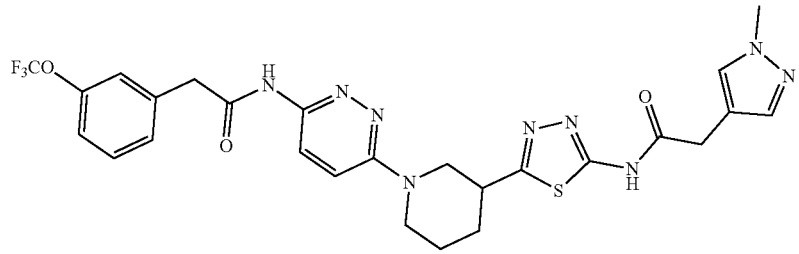 [SMILES: Cn1cc(CC(=O)Nc2nnc(C3CCCN(c4ccc(NC(=O)Cc5cccc(OC(F)(F)F)c5)nn4)C3)s2)cn1]

The title compound was synthesized by a similar procedure to Example 14. MS (ES$^+$) C$_{26}$H$_{26}$F$_3$N$_9$O$_3$S requires: 601, found: 602 [M+H]$^+$. $^1$H NMR (600 MHz, DMSO-d$_6$) δ: 12.59 (brs, 1H), 10.97 (s, 1H), 8.00 (d, J=9.8 Hz, 1H), 7.59 (s, 1H), 7.44-7.49 (m, 1H), 7.41 (d, J=9.8 Hz, 1H), 7.34-7.38 (m, 2H), 7.32 (s, 1H), 7.25 (br d, 1H), 4.42 (d, J=10.6 Hz, 1H), 4.03 (br d, 1H), 3.75-3.83 (m, 6H), 3.61 (s, 2H), 3.30-3.35 (m, 1H), 3.12-3.21 (m, 1H), 2.11-2.20 (m, 1H), 1.74-1.90 (m, 2H), 1.57-1.68 (m, 1H).

Example 25: N-(5-(3-(5-acetamido-1,3,4-thiadiazol-2-yl)piperidin-1-yl)-1,3,4-thiadiazol-2-yl)-2-(3-(trifluoromethoxy)phenyl)acetamide

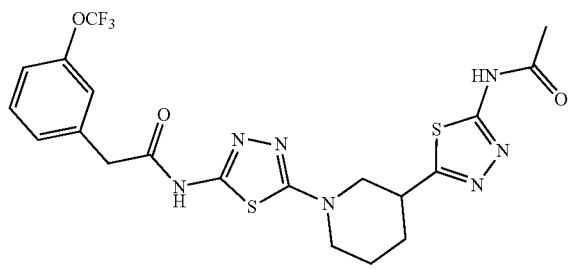 [SMILES: CC(=O)Nc1nnc(C2CCCN(c3nnc(NC(=O)Cc4cccc(OC(F)(F)F)c4)s3)C2)s1]

The title compounds was synthesized by a similar procedure to Example 26, step 4 (3.6 mg, 23%). MS (ES$^+$) C$_{20}$H$_{20}$F$_3$N$_7$O$_3$S$_2$ requires: 527, found: 528 [M+H]$^+$.

Example 26: 2-(pyridin-2-yl)-N-(5-(1-(5-(2-(3-(trifluoromethoxy)phenyl)acetamido)-1,3,4-thiadiazol-2-yl)piperidin-3-yl)-1,3,4-thiadiazol-2-yl)acetamide

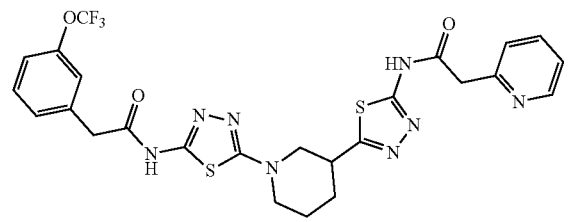 [SMILES: O=C(Cc1ccccn1)Nc1nnc(C2CCCN(c3nnc(NC(=O)Cc4cccc(OC(F)(F)F)c4)s3)C2)s1]

Steps 1-4

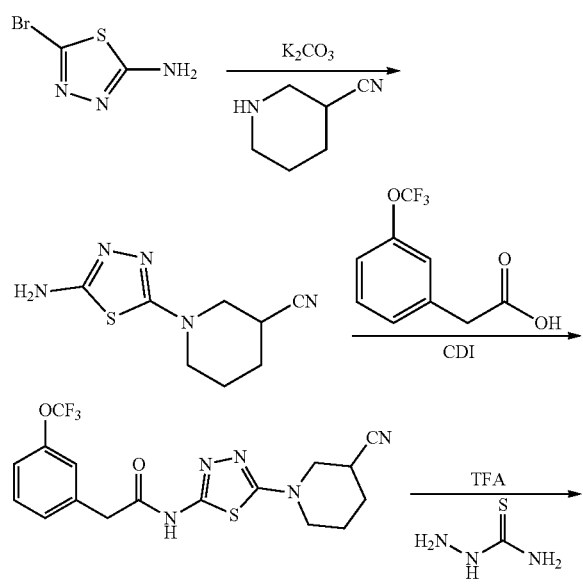

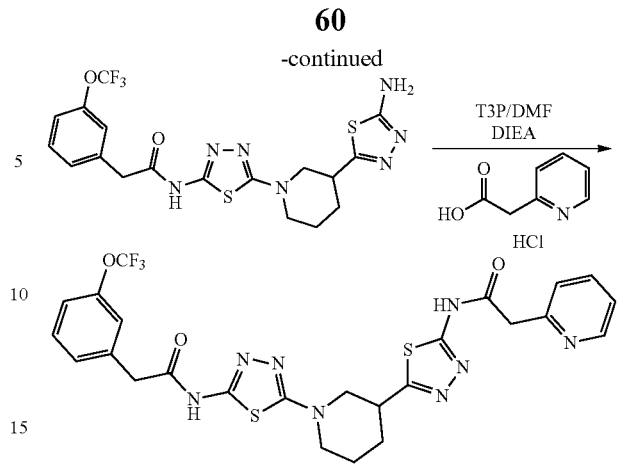

Step 1: 1-(5-amino-1,3,4-thiadiazol-2-yl)piperidine-3-carbonitrile

To a microwave vial containing 5-bromo-1,3,4-thiadiazol-2-amine (200 mg, 1.111 mmol), piperidine-3-carbonitrile (245 mg, 2.222 mmol), and K$_2$CO$_3$ (307 mg, 2.222 mmol) was added DMF (1 ml). The vial was heated in a microwave reactor at 120° C. for 30 min. The reaction mixture was concentrated, diluted with DCM and washed with saturated sodium bicarbonate. The aqueous layer was extracted with DCM (2×). The organic layers were combined, washed with brine, dried over sodium sulfate and concentrated to give crude product as a dark green semi-solid. The aqueous layer containing product was diluted with MeOH and the resulting precipitate filtered off. The filtrate was concentrated and triturated with DCM to give additional crude product. The two batches of crude product were combined to give a light brown semi-solid. The residue was purified via silica gel chromatography in (0-50% of an 80/20/1 DCM/MeOH/NH$_4$OH solution in DCM) to give the title compound as a light gray semi-solid. MS (ES$^+$) C$_8$H$_{11}$N$_5$S requires: 209, found: 210 [M+H]$^+$.

Step 2: N-(5-(3-cyanopiperidin-1-yl)-1,3,4-thiadiazol-2-yl)-2-(3-(trifluoromethoxy)phenyl)acetamide To a solution of 2-(3-(trifluoromethoxy)phenyl)acetic acid (245 mg, 1.112 mmol) in acetonitrile (2 ml), was added CDI (180 mg, 1.112 mmol) and the reaction stirred at room temperature for 1 hr. To the reaction was added 1-(5-amino-1,3,4-thiadiazol-2-yl)piperidine-3-carbonitrile (194 mg, 0.927 mmol) and the reaction was stirred and heated to 60° C. for 1 hr and then 40° C. for 20 hrs. The reaction mixture was concentrated, diluted with DCM, and washed with saturated sodium bicarbonate. The aqueous layer was extracted with DCM (2×). The organic layers were combined, washed with brine, dried over sodium sulfate, and concentrated to give the crude product as a yellow semi-solid. The residue was purified via silica gel chromatography (0-25% of an 80/20/1 DCM/MeOH/NH$_4$OH solution in DCM) to give the desired product. Isolated impure fractions were repurified by the same procedure and combined with the first isolation to give the title compound (74 mg, 19%) as a white solid. MS (ES$^+$) C$_{17}$H$_{16}$F$_3$N$_5$O$_2$S requires: 411, found: 412 [M+H]$^+$.

Step 3: Example 16: N-(5-(3-(5-amino-1,3,4-thiadiazol-2-yl)piperidin-1-yl)-1,3,4-thiadiazol-2-yl)-2-(3-(trifluoromethoxy)phenyl)acetamide

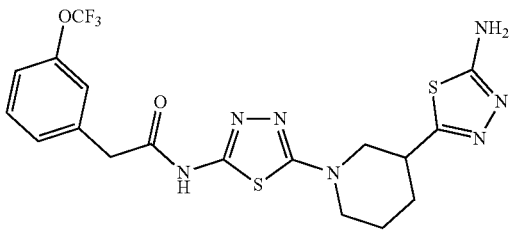 [SMILES: Nc1nnc(C2CCCN(c3nnc(NC(=O)Cc4cccc(OC(F)(F)F)c4)s3)C2)s1]

To a vial containing N-(5-(3-cyanopiperidin-1-yl)-1,3,4-thiadiazol-2-yl)-2-(3-(trifluoromethoxy)phenyl)acetamide (49.1 mg, 0.119 mmol) was added TFA (211 µl, 2.75 mmol) and hydrazinecarbothioamide (15.23 mg, 0.167 mmol) and the reaction was stirred at 80° C. for 1 hr and then allowed to cool to RT overnight. The reaction was then heated at 80° C. for 21 hrs. The reaction mixture was concentrated and purified via silica gel chromatography (0-50% of an 80/20/1 DCM/MeOH/NH$_4$OH solution in DCM) to give the title compound (39 mg, 68%). MS (ES$^+$) C$_{18}$H$_{18}$F$_3$N$_7$O$_2$S$_2$ requires: 485, found: 486 [M+H]$^+$.

Step 4: 2-(pyridin-2-yl)-N-(5-(1-(5-(2-(3-(trifluoromethoxy)phenyl)acetamido)-1,3,4-thiadiazol-2-yl)piperidin-3-yl)-1,3,4-thiadiazol-2-yl) acetamide To a stirred solution of N-(5-(3-(5-amino-1,3,4-thiadiazol-2-yl)piperidin-1-yl)-1,3,4-thiadiazol-2-yl)-2-(3-(trifluoromethoxy)phenyl)acetamide (19.4 mg, 0.040 mmol) in DMF (0.200 ml) cooled in an ice bath was added 2-(pyridin-2-yl)acetic acid hydrochloride (24.97 mg, 0.144 mmol), followed by T3P (50% solution in DMF, 0.105 ml, 0.180 mmol) added dropwise, and then TEA (0.050 ml, 0.360 mmol) added dropwise and the reaction was warmed to room temperature and stirred 15 hrs. The reaction mixture was concentrated, diluted with DCM, washed with sodium bicarbonate (2×), brine, and concentrated to reveal a bright yellow solid. The crude product was adsorbed onto silica gel and purified via silica gel chromatography (0-50% of an 80/20/1 DCM/MeOH/NH$_4$OH solution in DCM) to give the title compound (12 mg, 51%) as a pale yellow solid. MS (ES$^+$) C$_{25}$H$_{23}$F$_3$N$_8$O$_3$S$_2$ requires: 604, found: 605 [M+H]$^+$.
$^1$H NMR (600 MHz, DMSO-d$_6$) δ: 12.74 (brs, 1H), 12.34 (brs, 1H), 8.49 (d, J=4.53 Hz, 1H), 7.77 (t, J=7.55 Hz, 1H); 7.43-7.49 (m, 1H); 7.39 (d, J=7.93 Hz, 1H); 7.31-7.35 (m, 2H); 7.24-7.30 (m, 2H); 4.02-4.06 (m, 1H); 4.01 (s, 2H); 3.82 (s, 2H); 3.57-3.67 (m, 1H); 3.2-3.5 (m, 3H), 2.06-2.17 (m, 1H), 1.64-1.87 (m, 3H).

Example 27: N-(6-(1-(5-acetamido-1,3,4-thiadiazol-2-yl)pyrrolidin-3-yl)pyridazin-3-yl)-2-(3-(trifluoromethoxy)phenyl)acetamide

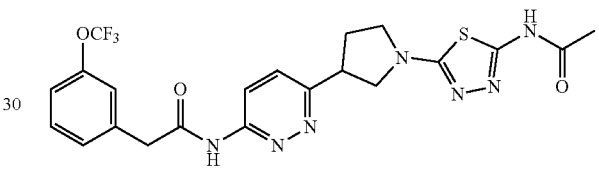

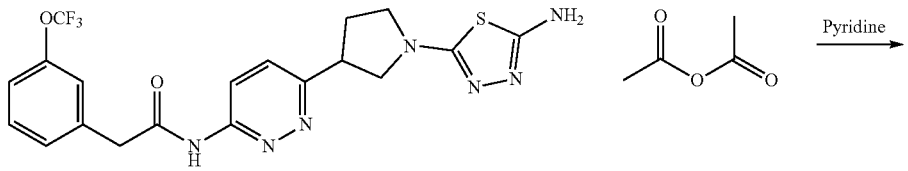

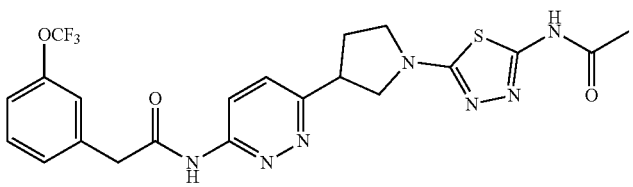

To a solution of N-(6-(1-(5-amino-1,3,4-thiadiazol-2-yl)pyrrolidin-3-yl)pyridazin-3-yl)-2-(3-(trifluoromethoxy)phenyl)acetamide (20 mg, 0.043 mmol) in pyridine (0.5 ml) was cooled in an ice bath and acetic anhydride (4.46 μl, 0.047 mmol) was added dropwise. The resulting mixture was stirred and warmed to room temperature over 1 hr. The volatiles were removed under reduced pressure and the residue was purified by mass-triggered preparative HPLC (Mobile phase: A=0.1% TFA/H₂O, B=0.1% TFA/MeCN; Gradient: B=30-70%; 20 min; Column: C18) to give the title compound (2.6 mg, 12%) as a pale yellow foam solid. MS (ES⁺) C₂₁H₂₀F₃N₇O₃S requires: 507, found: 508 [M+H]⁺. ¹H NMR (600 MHz, TFA+DMSO-d₆) δ 12.81 (brs, 1H), 11.46 (s, 1H), 8.32 (d, J=9.3 Hz, 1H), 7.77 (d, J=9.3 Hz, 1H), 7.47 (t, J=7.9 Hz, 1H), 7.41-7.35 (s, 2H), 7.25 (d, J=8.2 Hz, 1H), 4.12-4.06 (m, 1H), 4.04-3.93 (m, 2H), 3.89 (s, 2H), 3.81-3.72 (m, 2H), 2.63-2.57 (m, 1H), 2.38-2.30 (m, 1H), 2.21 (s, 3H).

Example 28: [this Example is Intentionally Left Blank]

Example 29: N-(6-(3-(5-acetamido-1,3,4-thiadiazol-2-yl)pyrrolidin-1-yl)pyridazin-3-yl)-2-(3-(trifluoromethoxy)phenyl)acetamide

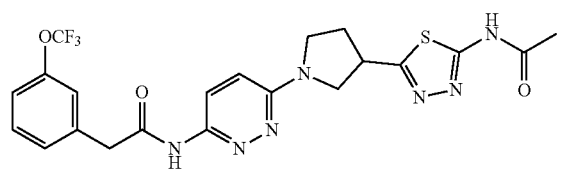 [SMILES: CC(=O)Nc1nnc(C2CCN(c3ccc(NC(=O)Cc4cccc(OC(F)(F)F)c4)nn3)C2)s1]

The compound was prepared by the same procedure as Example 27. The residue was purified by mass-triggered preparative HPLC (Mobile phase: A=0.1% TFA/H₂O, B=0.1% TFA/MeCN; Gradient: B=30-70%; 20 min; Column: C18) to give the title compound (5.5 mg, 10.84 μmol, 16.8% yield) as a pale yellow solid. MS (ES⁺) C₂₁H₂₀F₃N₇O₃S requires: 507, found: 508 [M+H]⁺. ¹H NMR (600 MHz, DMSO-d₆) δ 12.49 (s, 1H), 11.13 (brs, 1H), 8.20 (br d, J=9.7 Hz, 1H), 7.53-7.41 (m, 2H), 7.39-7.33 (m, 2H), 7.27 (d, J=8.1 Hz, 1H), 4.11-4.00 (m, 2H), 3.85-3.79 (m, 1H), 3.82 (s, 2H), 3.74-3.68 (m, 1H), 3.67-3.60 (m, 1H), 2.59-2.52 (m, 1H), 2.34-2.25 (m, 1H), 2.17 (s, 3H).

Example 30: 2-(2-phenylthiazol-4-yl)-N-(5-(1-(6-(2-(3-(trifluoromethoxy)phenyl)acetamido)pyridazin-3-yl)pyrrolidin-3-yl)-1,3,4-thiadiazol-2-yl)acetamide

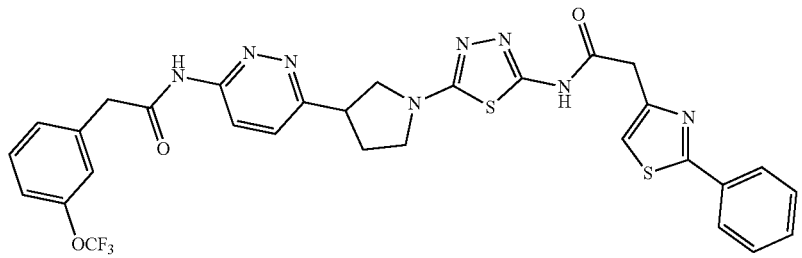 [SMILES: O=C(Cc1cccc(OC(F)(F)F)c1)Nc1ccc(C2CCN(c3nnc(NC(=O)Cc4csc(-c5ccccc5)n4)s3)C2)nn1]

The compound was prepared by the same procedure as Example 21, Step 2. The residue was purified by mass-triggered preparative HPLC (Mobile phase: A=0.1% TFA/H₂O, B=0.1% TFA/MeCN; Gradient: B=30-70%; 20 min; Column: C18) to give the title compound (6.8 mg, 24%). MS (ES⁺) C₃₀H₂₅F₃N₈O₃S₂ requires: 666, found: 667 [M+H]⁺. ¹H NMR (600 MHz, DMSO-d₆) δ 12.79 (s, 1H), 10.98 (brs, 1H), 8.06 (brs, 1H), 7.90 (d, J=7.8 Hz, 2H), 7.57 (s, 1H), 7.52-7.44 (m, 4H), 7.38-7.33 (m, 2H), 7.25 (d, J=8.7 Hz, 1H), 7.16 (brs, 1H), 4.08-4.03 (m, 1H), 4.05 (s, 2H), 3.99-3.92 (m, 1H), 3.79 (s, 2H), 3.78-3.73 (m, 1H), 3.68-3.62 (m, 1H), 3.61-3.55 (m, 1H), 2.57-2.47 (m, 1H), 2.31-2.24 (m, 1H).

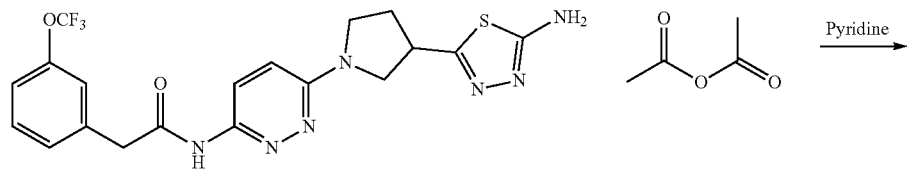

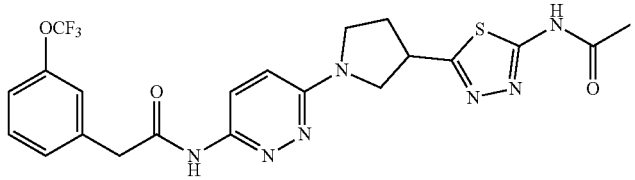

Example 31: 2-(thiazol-4-yl)-N-(5-(1-(6-(2-(3-(trifluoromethoxy)phenyl)acetamido)pyridazin-3-yl)pyrrolidin-3-yl)-1,3,4-thiadiazol-2-yl)acetamide

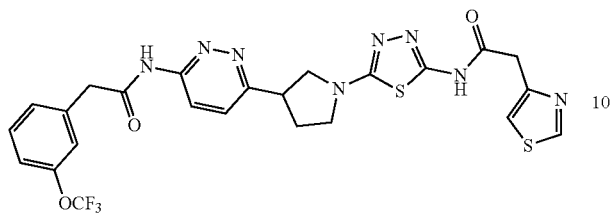

The compound was prepared by the same procedure as Example 21, Step 2. The residue was purified by mass-triggered preparative HPLC (Mobile phase: A=0.1% TFA/H₂O, B=0.1% TFA/MeCN; Gradient: B=40-60%; 20 min; Column: C18) to give the title compound (3.9 mg, 15%) MS (ES⁺) $C_{24}H_{21}F_3N_8O_3S_2$ requires: 590, found: 591 [M+H]⁺. ¹H NMR (600 MHz, DMSO-d₆) δ 12.80 (brs, 1H), 11.22 (s, 1H), 9.04 (d, J=1.9 Hz, 1H), 8.28 (d, J=9.9 Hz, 1H), 7.63 (br d, J=9.2 Hz, 1H), 7.58-7.56 (m, 1H), 7.47 (t, J=7.9 Hz, 1H), 7.38-7.34 (m, 2H), 7.27 (d, J=8.1 Hz, 1H), 4.14-4.03 (m, 2H), 4.03 (s, 2H), 3.91-3.85 (m, 1H), 3.84 (s, 2H), 3.77-3.71 (m, 1H), 3.71-3.64 (m, 1H), 2.61-2.53 (m, 1H), 2.35-2.27 (m, 1H).

Example 32: IACS-006086 2-(pyridin-2-yl)-N-(5-(1-(5-(2-(3-(trifluoromethoxy)phenyl)acetamido)-1,3,4-thiadiazol-2-yl)pyrrolidin-3-yl)-1,3,4-thiadiazol-2-yl)acetamide

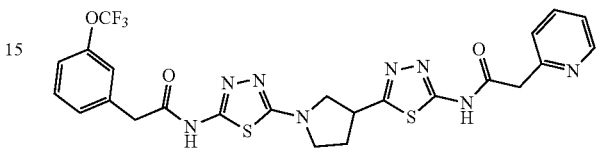

The title compound was synthesized by a similar procedure to Example 26. MS (ES⁺) $C_{24}H_{21}F_3N_8O_3S_2$ requires: 590, found: 591 [M+H]⁺.

Example 33: 2-(2,4-difluorophenyl)-N-(5-(1-(6-(2-(3-(trifluoromethoxy)phenyl)acetamido)pyridazin-3-yl)pyrrolidin-3-yl)-1,3,4-thiadiazol-2-yl)acetamide

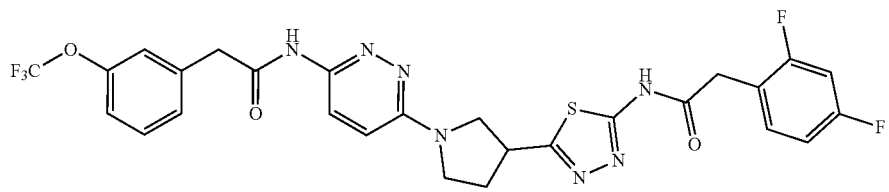 [SMILES: O=C(Cc1cccc(OC(F)(F)F)c1)Nc1ccc(N2CCC(c3nnc(NC(=O)Cc4ccc(F)cc4F)s3)C2)nn1]

The compound was synthesized by a similar procedure to Example 20. 2-(2-fluorophenyl)-N-(5-(1-(6-(2-(3-(trifluoromethoxy)phenyl)acetamido)pyridazin-3-yl)pyrrolidin-3-yl)-1,3,4-thiadiazol-2-yl)acetamide 2,2,2-trifluoroacetate. The residue was purified by mass-triggered preparative HPLC (Mobile phase: A=0.1% TFA/H₂O, B=0.1% TFA/MeCN; Gradient: B=30-70%; 20 min; Column: C18) to give the title compound (2 mg, 6%). MS (ES+) $C_{27}H_{22}F_5N_7O_3S$ requires: 619, found: 620 [M+H]⁺

Example 34: 2-(tetrahydro-2H-pyran-2-yl)-N-(5-(1-(6-(2-(3-(trifluoromethoxy)phenyl)acetamido)pyridazin-3-yl)pyrrolidin-3-yl)-1,3,4-thiadiazol-2-yl)acetamide

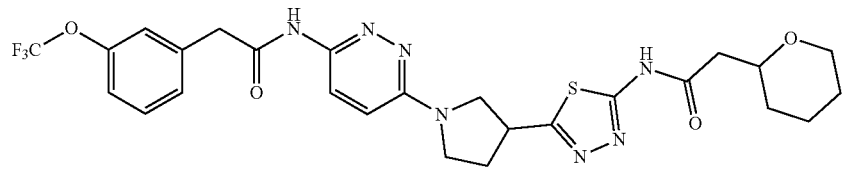 [SMILES: O=C(Cc1cccc(OC(F)(F)F)c1)Nc1ccc(N2CCC(c3nnc(NC(=O)CC4CCCCO4)s3)C2)nn1]

The compound was synthesized by a similar procedure to Example 20. 2-(2-fluorophenyl)-N-(5-(1-(6-(2-(3-(trifluoromethoxy)phenyl)acetamido)pyridazin-3-yl)pyrrolidin-3-yl)-1,3,4-thiadiazol-2-yl)acetamide 2,2,2-trifluoroacetate. The residue was purified by mass-triggered preparative HPLC (Mobile phase: A=0.1% TFA/H$_2$O, B=0.1% TFA/MeCN; Gradient: B=30-70%; 20 min; Column: C18) to give the title compound (7 mg, 16%) as a white solid. MS (ES+) C$_{26}$H$_{28}$F$_3$N$_7$O$_4$S requires: 591, found: 592 [M+H]$^+$. $^1$H NMR (600 MHz, d$_6$-DMSO) δ: 12.46 (s, 1H), 11.00 (brs, 1H), 8.07 (brs, 1H), 7.46 (t, J=7.9 Hz, 1H), 7.38-7.30 (m, 2H), 7.26 (d, J=8.4 Hz, 1H), 7.25-7.08 (m, 1H), 4.07-4.01 (m, 1H), 3.98-3.91 (m, 1H), 3.80 (s, 2H), 3.82-3.74 (m, 1H), 3.73-3.65 (m, 2H), 3.62-3.54 (m, 1H), 3.34-3.25 (m, 2H), 2.62-2.49 (m, 3H), 2.32-2.23 (m, 1H), 1.79-1.72 (m, 1H), 1.62-1.57 (m, 1H), 1.51-1.35 (m, 3H), 1.27-1.17 (m, 1H).

Example 36: 2-(benzo[d]isoxazol-3-yl)-N-(5-(1-(6-(2-(3-(trifluoromethoxy)phenyl)acetamido)pyridazin-3-yl)pyrrolidin-3-yl)-1,3,4-thiadiazol-2-yl)acetamide

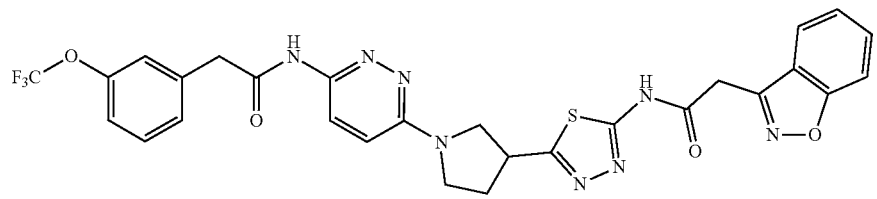 [SMILES: O=C(Cc1cccc(OC(F)(F)F)c1)Nc1ccc(N2CCC(c3nnc(NC(=O)Cc4noc5ccccc45)s3)C2)nn1]

The compound was synthesized by a similar procedure to Example 20. MS (ES+) C$_{28}$H$_{23}$F$_3$N$_8$O$_4$S requires: 624, found: 625 [M+H]$^+$.

Example 37: N-((1-methyl-1H-pyrazol-3-yl)methyl)-5-(3-(6-(2-(pyridin-2-yl)acetamido)pyridazin-3-yl)pyrrolidin-1-yl)-1,3,4-thiadiazole-2-carboxamide

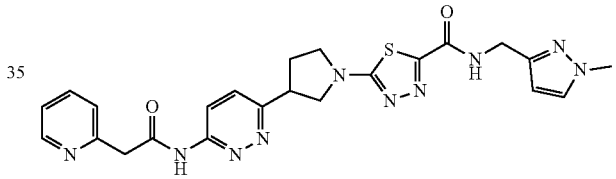

Steps 1-3

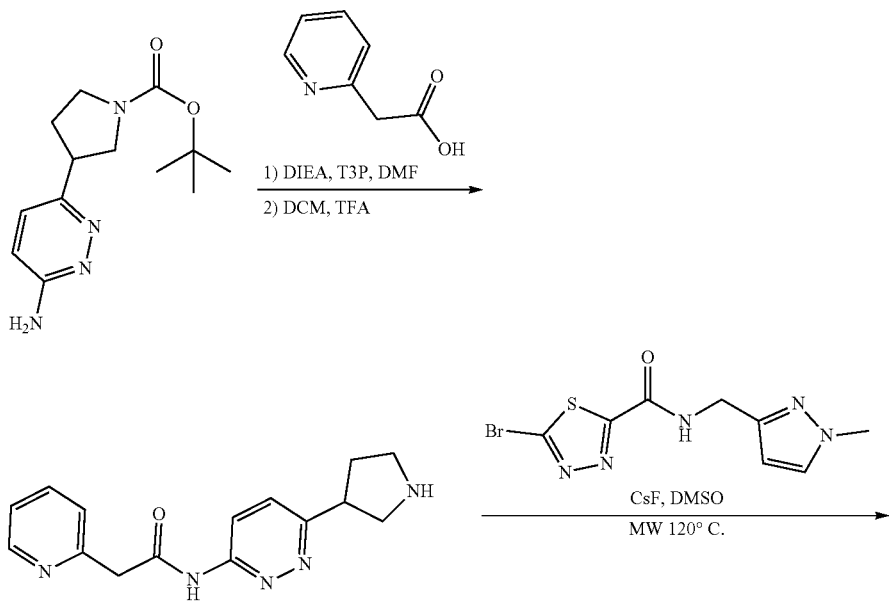

-continued

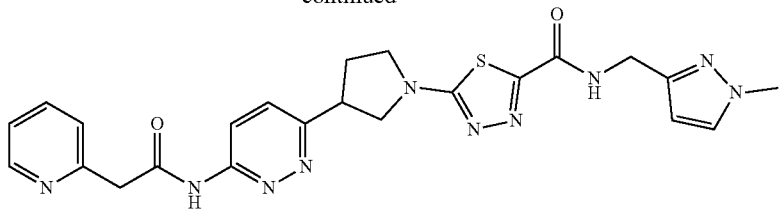

Step 1: Tert-butyl 3-(6-(2-(pyridin-2-yl)acetamido)pyridazin-3-yl)pyrrolidine-1-carboxylate To a solution of tert-butyl 3-(6-aminopyridazin-3-yl)pyrrolidine-1-carboxylate (180 mg, 0.681 mmol), 2-(pyridin-2-yl)acetic acid hydrochloride (236 mg, 1.362 mmol) and DIEA (0.476 ml, 2.72 mmol) in DMF (2 ml), cooled in an ice bath, was added T3P (50% solution in DMF, 0.867 ml, 1.362 mmol) and the reaction was stirred for 15 min, allowed to reach RT and stirred for 2 hrs. The mixture was taken up in DCM/MeOH (10%) and washed with water. The aqueous phase was extracted twice with DCM/MeOH (10%). The combined organic layers were concentrated and the residue was purified via silica gel chromatography (0-10% MeOH in DCM) to give the title compound (244 mg, 93%). MS (ES$^+$) C$_{20}$H$_{25}$N$_5$O$_3$ requires: 383, found: 384 [M+H]$^+$.

Step 2: 2-(pyridin-2-yl)-N-(6-(pyrrolidin-3-yl)pyridazin-3-yl)acetamide

To a solution of tert-butyl 3-(6-(2-(pyridin-2-yl)acetamido)pyridazin 3-yl)pyrrolidine-1-carboxylate (244 mg, 0.636 mmol) in DCM (1.5 ml) was added TFA (0.75 ml) and the resulting mixture was stirred at RT for 1 hr. The volatiles were removed under reduced pressure. Water was added to the residue and the aqueous layer was extracted 3 times with EtOAc/MeOH (10%). The combined organic layers were washed with brine, dried over Na$_2$SO$_4$, filtered and concentrated under reduced pressure to give the title compound which was used as is. MS (ES$^+$) C$_{15}$H$_{17}$N$_5$O requires: 283, found: 284 [M+H]$^+$.

Step 3: N-((1-methyl-1H-pyrazol-3-yl)methyl)-5-(3-(6-(2-(pyridin-2-yl)acetamido)pyridazin-3-yl)pyrrolidin-1-yl)-1,3,4-thiadiazole-2-carboxamide The compound was prepared by the procedure of Example 22, Step 5. The residue was purified by mass-triggered preparative HPLC (Mobile phase: A=0.1% TFA/H$_2$O, B=0.1% TFA/MeCN; Gradient: B=10-40%; 20 min; Column: C18) to give of the title compound (13.4 mg, 37%) as a pale yellow amorphous material. MS (ES$^+$) C$_{23}$H$_{24}$N$_{10}$O$_2$S requires: 504, found: 505 [M+H]$^+$. $^1$H NMR (600 MHz, DMSO-d$_6$) δ 11.50 (s, 1H), 9.06 (t, J=6.1 Hz, 1H), 8.74 (d, J=5.1 Hz, 1H), 8.29-8.16 (m, 2H), 7.80-7.73 (m, 2H), 7.69-7.64 (m, 1H), 7.58-7.55 (m, 1H), 6.12 (d, J=1.8 Hz, 1H), 4.36 (d, J=6.1 Hz, 2H), 4.22 (s, 2H), 4.02-3.89 (m, 2H), 3.81-3.78 (m, 1H), 3.77 (s, 3H), 3.73-3.58 (m, 2H), 2.55-2.48 (m, 1H), 2.34-2.27 (m, 1H).

Example 38: 5-(3-(6-(2-(pyridin-2-yl)acetamido)pyridazin-3-yl)pyrrolidin-1-yl)-N-((4-(trifluoromethyl)pyridin-2-yl)methyl)-1,3,4-thiadiazole-2-carboxamide

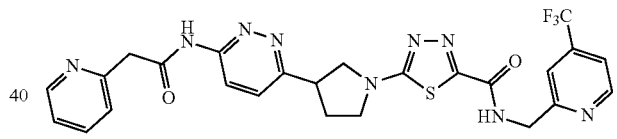

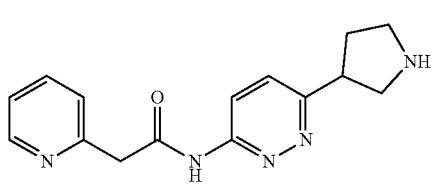 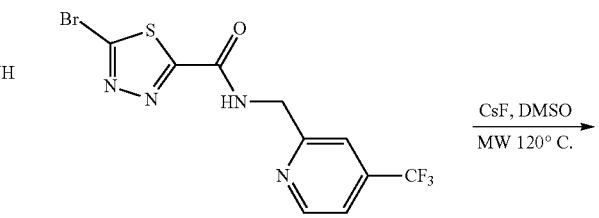

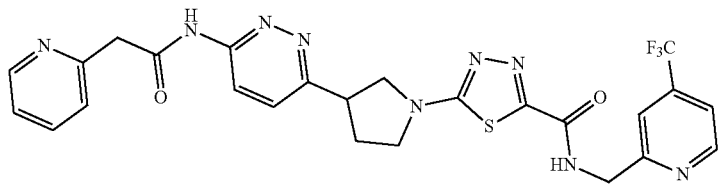

The compound was prepared by the procedure of Example 37, step 3. N-((1-methyl-1H-pyrazol-3-yl)methyl)-5-(3-(6-(2-(pyridin-2-yl)acetamido)pyridazin-3-yl)pyrrolidin-1-yl)-1,3,4-thiadiazole-2-carboxamide was prepared from 5-bromo-N-((4-(trifluoromethyl)pyridin-2-yl)methyl)-1,3,4-thiadiazole-2-carboxamide (synthesized by a similar procedure as 5-Bromo-N-(3-(trifluoromethoxy)benzyl)-1,3,4-thiadiazole-2-carboxamide). The residue was purified by mass-triggered preparative HPLC (Mobile phase: A=0.1% TFA/H$_2$O, B=0.1% TFA/MeCN; Gradient: B=10-30%; 20 min; Column: C18) to give the title compound (9.5 mg, 24%) as a white powder. MS (ES$^+$) C$_{25}$H$_{22}$F$_3$N$_9$O$_2$S requires: 569, found: 570 [M+H]$^+$. $^1$H NMR (600 MHz, DMSO-d$_6$) δ 11.45 (s, 1H), 9.42 (t, J=6.0 Hz, 1H), 8.81 (d, J=5.0 Hz, 1H), 8.66 (brd, J=4.2 Hz, 1H), 8.25 (d, J=9.1 Hz, 1H), 8.06 (brs, 1H), 7.75 (d, J=9.2 Hz, 1H), 7.69-7.61 (m, 3H), 7.54 (brs, 1H), 4.65 (d, J=6.0 Hz, 2H), 4.14 (s, 2H), 4.03-3.90 (m, 2H), 3.83-3.77 (m, 1H), 3.74-3.59 (m, 2H), 2.57-2.47 (m, 1H), 2.35-2.27 (m, 1H).

Example 39: 5-(3-(6-(2-(pyridin-2-yl)acetamido)pyridazin-3-yl)pyrrolidin-1-yl)-1,3,4-thiadiazole-2-carboxamide

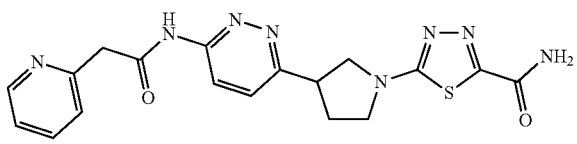 [SMILES: NC(=O)c1nnc(N2CCC(c3ccc(NC(=O)Cc4ccccn4)nn3)C2)s1]

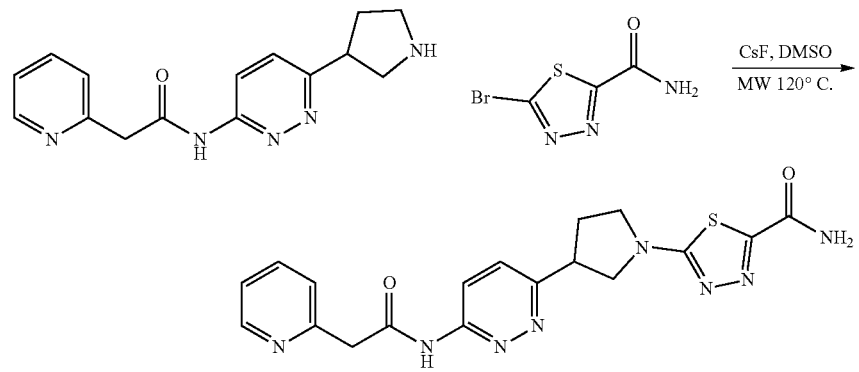

The compound was prepared by a similar procedure to Example 37, step 3, from 5-bromo-1,3,4-thiadiazole-2-carboxamide (synthesized by a similar procedure to 5-Bromo-N-(3-(trifluoromethoxy)benzyl)-1,3,4-thiadiazole-2-carboxamide). MS (ES$^+$) C$_{18}$H$_{18}$F$_3$N$_8$O$_2$S requires: 410, found: 411 [M+H]$^+$.

Example 40: N-methyl-5-(3-(6-(2-(1-(3-(trifluoromethoxy)phenyl)-1H-imidazol-4-yl)acetamido)pyridazin-3-yl)pyrrolidin-1-yl)-1,3,4-thiadiazole-2-carboxamide

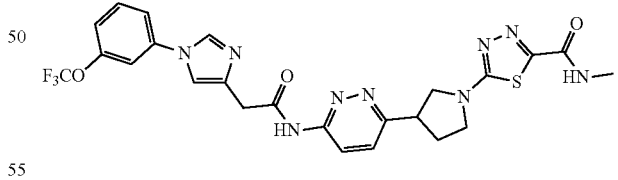

Steps 1-5

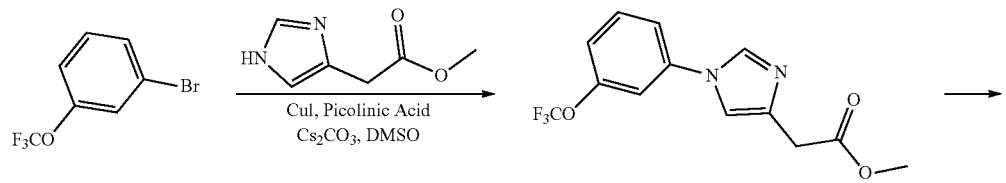

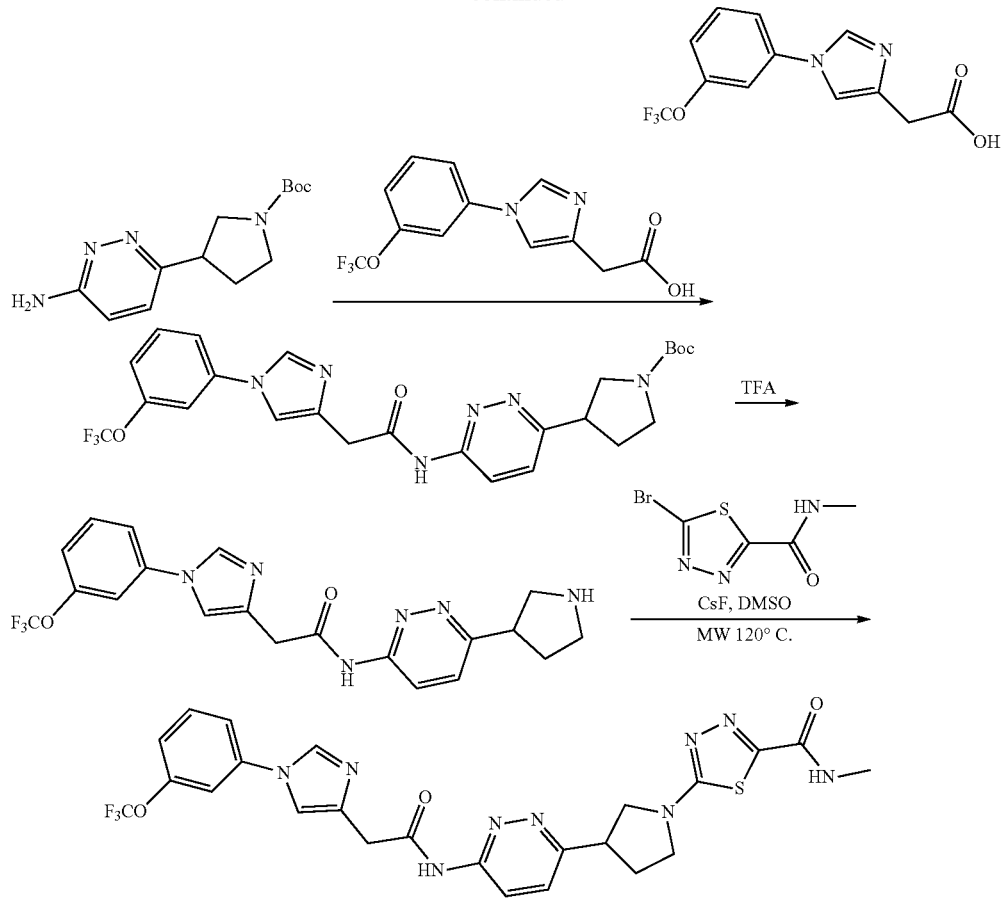

Step 1: Methyl 2-(1-(3-(trifluoromethoxy)phenyl)-1H-imidazol-4-yl)acetate

To a solution of 1-bromo-3-(trifluoromethoxy)benzene (2.6 g, 10.8 mmol), methyl 2-(1H-imidazol-4-yl)acetate (1.5 g, 10.8 mmol), CuI (205 mg, 1.08 mmol), picolinic acid (133 mg, 1.08 mmol), Cs$_2$CO$_3$ (10.5 g, 32.4 mmol) in DMSO (50 ml) were added, flushed with argon, stirred at 120° C. overnight. The reaction was diluted with water (100 ml) and the solution was washed with EtOAc. The organic phase was separated and the aqueous layer was extracted with EtOAc (100 ml×3). The organic layers were combined, washed with brine (100 ml), concentrated and purified by silica gel chromatography column (EtOAc in Hexanes from 30% to 70%) to give the title compound as a light brown solid (980 mg, 25%). MS (ES$^+$) C$_{13}$H$_{11}$F$_3$N$_2$O$_3$ requires: 300, found: 301 [M+H]$^+$.

Step 2: 2-(1-(3-(trifluoromethoxy)phenyl)-1H-imidazol-4-yl)acetic acid (MDA3462)

A mixture of methyl 2-(1-(3-(trifluoromethoxy)phenyl)-1H-imidazol-4-yl)acetate (980 mg, 3.27 mmol) in HCl (4N, 10 ml) was stirred at 75° C. overnight and monitored by LCMS. The mixture was concentrated to give the title compound as a light yellow solid (900 mg, 90%). MS (ES$^+$) C$_{12}$H$_9$F$_3$N$_2$O$_3$ requires: 286, found: 287 [M+H]$^+$.

Steps 3-4: N-(6-(pyrrolidin-3-yl)pyridazin-3-yl)-2-(1-(3-(trifluoromethoxy)phenyl)-1H-imidazol-4-yl)acetamide The compound was synthesized by a similar procedure to Example 37, step 1.

Step 5: N-methyl-5-(3-(6-(2-(1-(3-(trifluoromethoxy)phenyl)-1H-imidazol-4-yl)acetamido)pyridazin-3-yl)pyrrolidin-1-yl)-1,3,4-thiadiazole-2-carboxamide The compound was prepared by a similar procedure to Example 8, Step 5, from 5-bromo-N-methyl-1,3,4-thiadiazole-2-carboxamide (synthesized by a similar procedure to 5-Bromo-N-(3-(trifluoromethoxy)benzyl)-1,3,4-thiadiazole-2-carboxamide). The residue was purified by mass-triggered preparative HPLC (Mobile phase: A=0.1% TFA/H$_2$O, B=0.1% TFA/MeCN; Gradient: B=10-40%; 20 min; Column: C18) to give the title compound (2.5 mg, 12%) as an orange solid. MS (ES$^+$) C$_{24}$H$_{22}$F$_3$N$_9$O$_3$S requires: 573, found: 574 [M+H]$^+$. $^1$H NMR (600 MHz, DMSO-d$_6$) δ 11.35 (s, 1H), 8.98 (br-s, 1H), 8.75-8.69 (m, 1H), 8.28 (d, J=9.1 Hz, 1H), 7.95 (s, 1H), 7.86 (s, 1H), 7.80 (d, J=8.0 Hz, 1H), 7.76 (d, J=9.1 Hz, 1H), 7.71 (t, J=8.0 Hz, 1H), 7.47 (d, J=8.6 Hz, 1H), 4.01-3.89 (m, 4H), 3.78 (t, J=8.2 Hz, 1H), 3.72-3.60 (m, 2H), 2.76 (d, J=4.7 Hz, 3H), 2.54-2.47 (m, 1H), 2.34-2.26 (m, 1H).

Example 41: N-methyl-5-(3-(6-(2-(pyridin-2-yl)
acetamido)pyridazin-3-yl)pyrrolidin-1-yl)-1,3,4-
thiadiazole-2-carboxamide

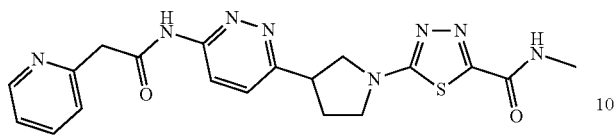

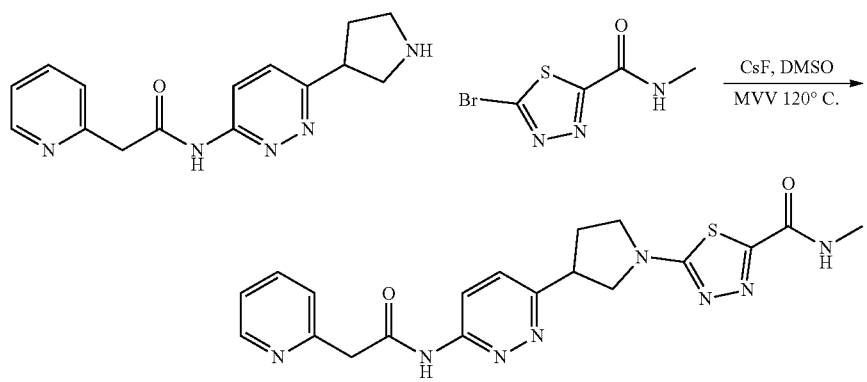

The compound was prepared by a similar procedure to Example 37, step 3. MS (ES+) $C_{19}H_{20}F_3N_8O_2S$ requires: 424, found: 425[M+H]+.

Example 42: 2-(pyridin-2-yl)-N-(6-(3-(5-(2-(3-(trif-
luoromethoxy)phenyl)acetamido)-1,3,4-thiadiazol-2-
yl)pyrrolidin-1-yl)pyridazin-3-yl)acetamide

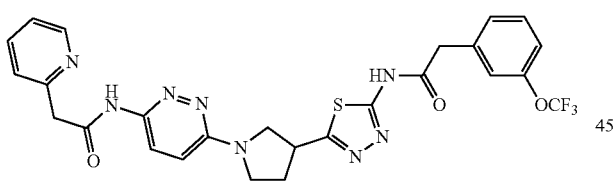

The compound was prepared using the procedure of Example 17 to give the title compound. MS (ES+) $C_{26}H_{23}F_3N_8O_3S$ requires: 584, found: 585 [M+H]+.

Example 43: 5-(3-(6-(2-(pyridin-2-yl)acetamido)
pyridazin-3-yl)pyrrolidin-1-yl)-N-(3-(trifluo-
romethoxy)benzyl)-1,3,4-thiadiazole-2-carboxamide

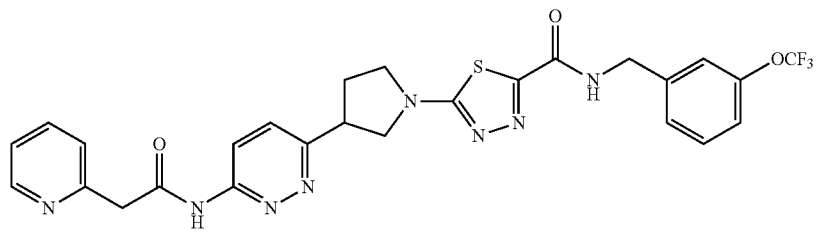 [SMILES: O=C(Cc1ccccn1)Nc1ccc(C2CCN(c3nnc(C(=O)NCc4cccc(OC(F)(F)F)c4)s3)C2)nn1]

Step 1

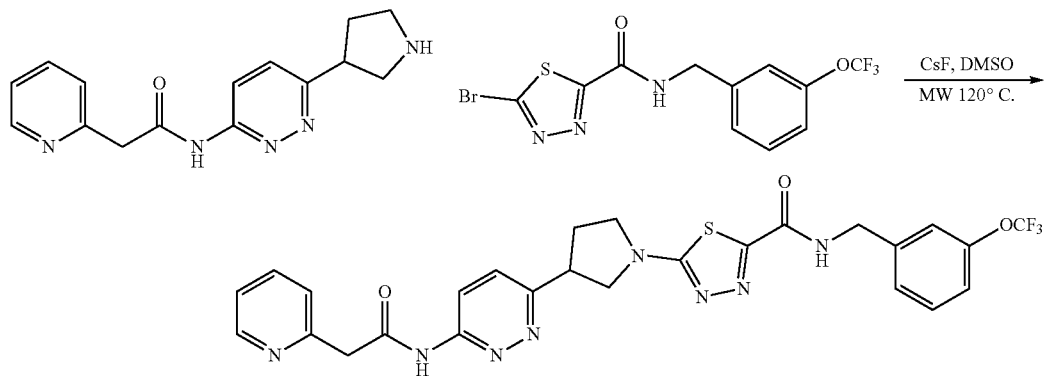

The compound was prepared by a similar procedure to Example 22, Step 5. The mixture was purified by mass-triggered preparative HPLC (Mobile phase: A=0.1% TFA/H$_2$O, B=0.1% TFA/MeCN; Gradient: B=30-70%; 20 min; Column: C18) to give the title compound (1.6 mg, 3%) as a white solid. MS (ES$^+$) C$_{26}$H$_{23}$F$_3$N$_8$O$_3$S requires: 584, found: 585 [M+H]$^+$.

Example 44: (R)-5-(3-(6-(2-(pyridin-2-yl)acetamido)pyridazin-3-yl)pyrrolidin-1-yl)-N-((4-(trifluoromethyl)pyridin-2-yl)methyl)-1,3,4-thiadiazole-2-carboxamide

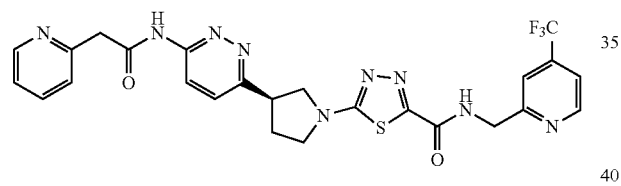

Steps 1-10

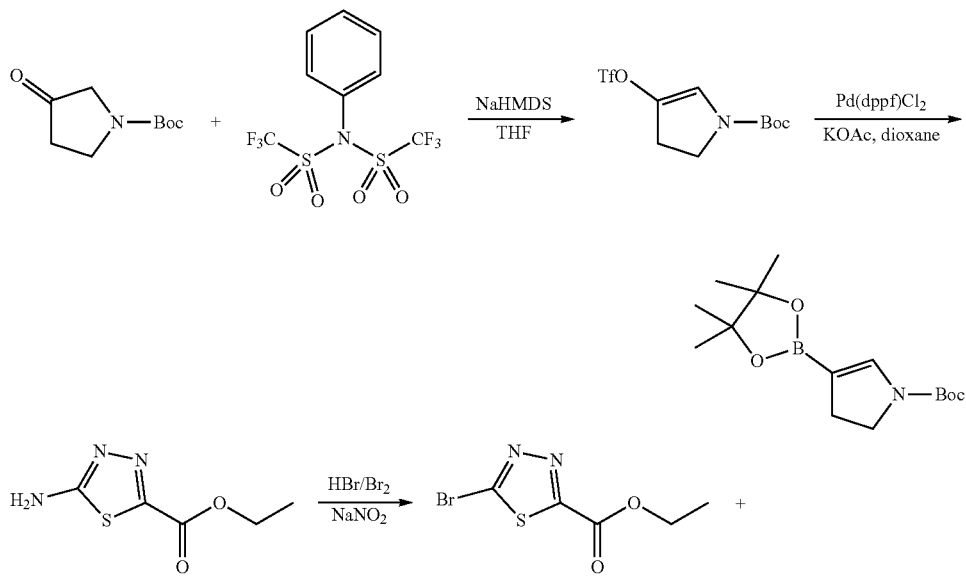

-continued
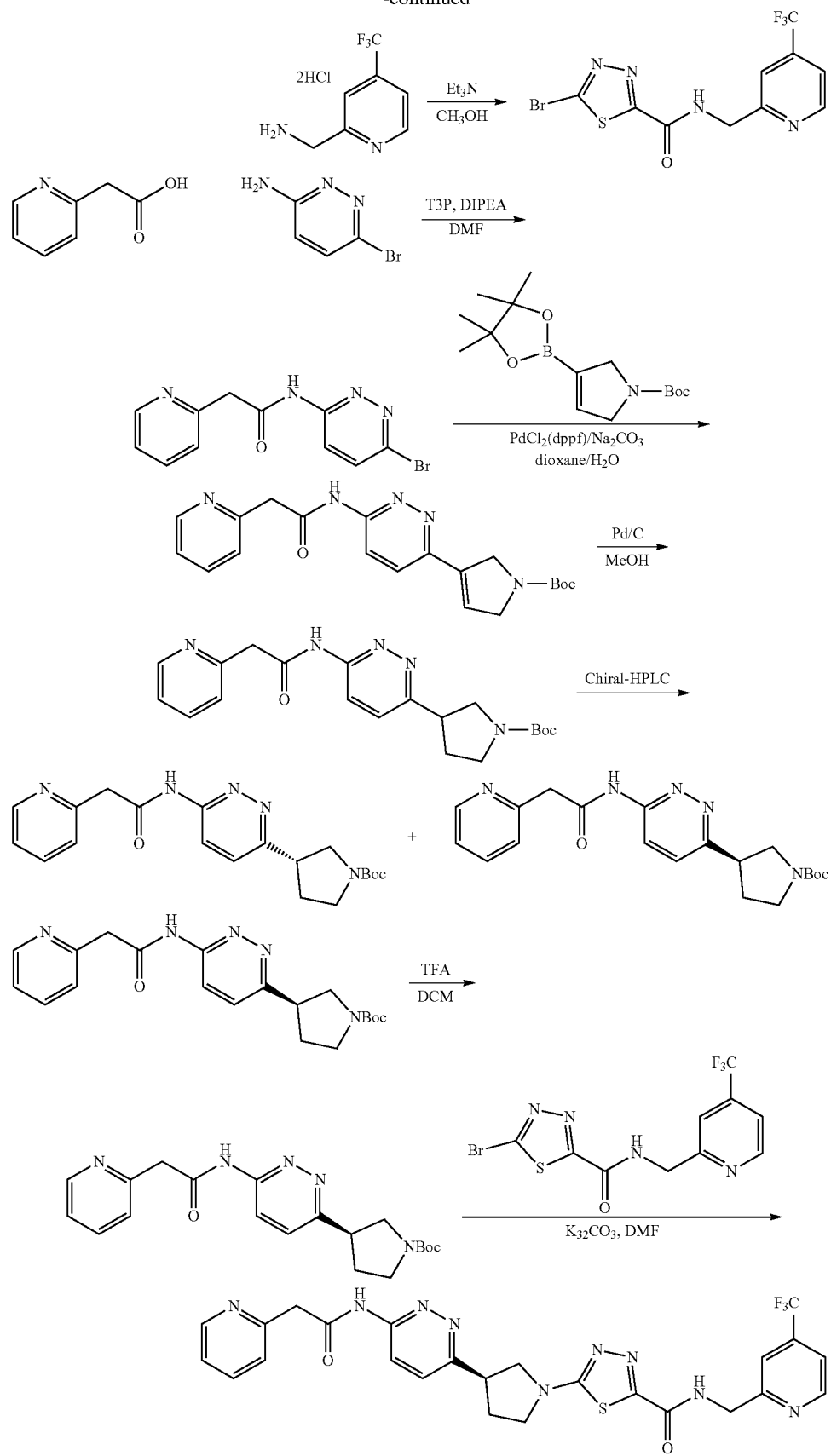

Step 1: Tert-butyl 4-(trifluoromethylsulfonyloxy)-2,3-dihydropyrrole-1-carboxylate

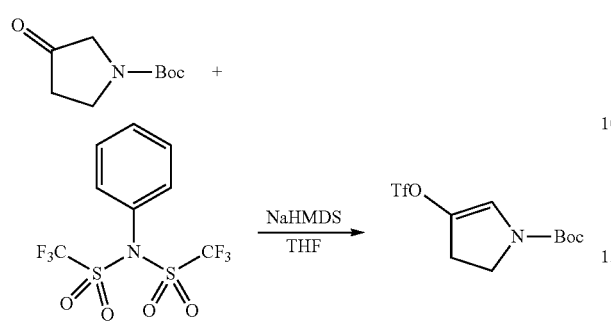

To a stirred solution of sodium bis(trimethylsilyl) amide (2M in THF, 27.5 ml, 55 mmol) in THF (200 ml) was added dropwise a solution of tert-butyl 3-oxopyrrolidine-1-carboxylate (9.25 g, 50 mmol) in THF (100 ml) at −78° C. After stirring for 15 min, trifluoro-N-phenyl-N-(trifluoromethylsulfonyl)methanesulfonamide (17.8 g, 50 mmol) in THF (100 ml) was added and the reaction mixture was stirred for 3 h at −78° C., and then at RT for 1 hr. The reaction mixture was quenched with aq. NaHCO$_3$ and extracted with EtOAc. The organic layer was washed with brine, dried and concentrated. The crude product was purified via silica gel chromatography (20-25% EtOAc in petroleum ether) to give the title compound (14.5 g, 92%) as a yellow oil. MS (ES+) $C_{10}H_{14}F_3NO_5S$ requires: 317, found: 262 [M-56+H]$^+$.

Step 2: Tert-butyl 4-(4,4,5,5-tetramethyl-1,3,2-dioxaborolan-2-yl)-2,3-dihydro-1H-pyrrole-1-carboxylate

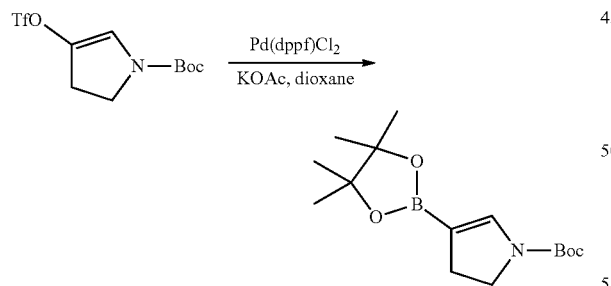

A mixture of tert-butyl 4-(trifluoromethylsulfonyloxy)-2,3-dihydropyrrole-1-carboxylate (14.5 g, 45.7 mmol), 4,4,4',4',5,5,5',5'-octamethyl-2,2'-bi(1,3,2-dioxaborolane) (12.8 g, 50.3 mmol), KOAc (13.4 g, 137 mmol) and Pd(dppf)Cl$_2$ (1.67 g, 2.3 mmol) in dioxane (200 ml) was heated at 80° C. for 16 h under Ar. The reaction mixture was cooled to RT and the mixture was purified via silica gel chromatography (20-25% EtOAc in Petroleum Ether) to give the title compound as a yellow oil (12.5 g, 93%). MS (ES+) $C_{15}H_{26}BNO_4$ requires: 295, found: 240 [M-56+H]$^+$.

Step 3: Ethyl 5-bromo-1,3,4-thiadiazole-2-carboxylate

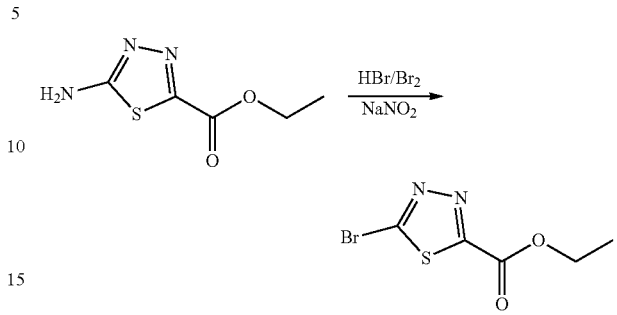

To a solution of aqueous hydrobromic acid (48%, 17 ml) at 5° C. was added ethyl 5-amino-1,3,4-thiadiazole-2-carboxylate (5.71 g, 33 mmol) followed by bromine (12.8 ml, 0.24 mol) at a rate such that the reaction mixture was kept at a temperature ≤11° C. A solution of sodium nitrite (6.0 g, 85 mmol) in water (8.5 ml) was added at a rate such that the reaction mixture was maintained at ~5° C. The reaction mixture was kept at 0° C. for 2 hrs. Water was added and it was extracted with EtOAc. The organic layer was washed with sat. Na$_2$S$_2$O$_3$ and brine, dried and concentrated. The crude product was purified via silica gel chromatography (20-25% EtOAc in Petroleum Ether) to afford the title compound (3.2 g, 41%) as a white solid. MS (ES+) $C_5H_5BrN_2O_2S$ requires: 236, found: 237 [M+H]$^+$.

Step 4: 5-bromo-N-((4-(trifluoromethyl)pyridin-2-yl)methyl)-1,3,4-thiadiazole-2-carboxamide

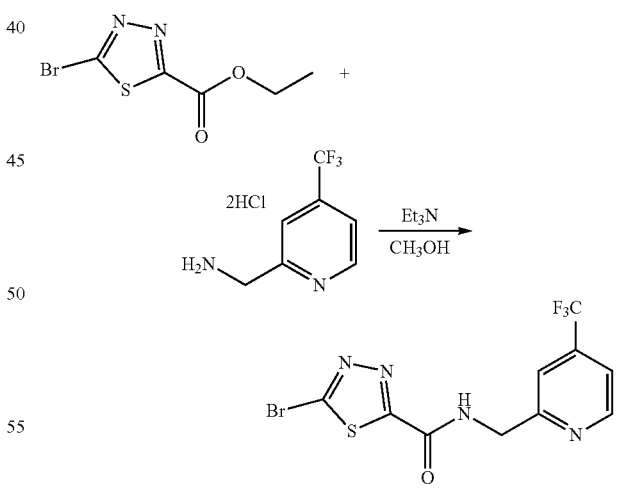

A mixture of ethyl 5-bromo-1,3,4-thiadiazole-2-carboxylate (2.0 g, 8.4 mmol), (4-(trifluoromethyl)pyridin-2-yl)methanamine dihydrochloride salt (2.1 g, 8.4 mmol) and Et$_3$N (2.13 g, 21.1 mmol) in MeOH (30 ml) was stirred at RT overnight. The mixture was purified via silica gel chromatography (20-35% EtOAc in Petroleum Ether) to afford the title compound as a beige solid (2.0 g, 65%). MS (ES+) $C_{10}H_6BrF_3N_4OS$ requires: 366, found: 367 [M+H]$^+$.

Step 5: N-(6-bromopyridazin-3-yl)-2-(pyridin-2-yl) acetamide

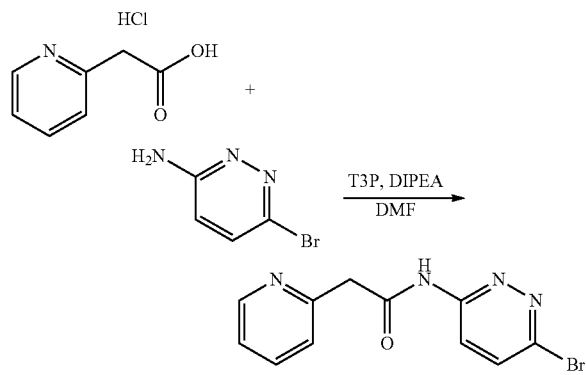

A mixture of 2-(pyridin-2-yl)acetic acid hydrochloride salt (28 g, 160 mmol), 6-bromopyridazin-3-amine (23.3 g, 134 mmol), T3P (102 g, 161 mmol, 50 wt % in DMF) and DIPEA (26 g, 200 mmol) in DMF (400 ml) was stirred at RT overnight. The reaction was added slowly to a mixture of sat. NaHCO$_3$ (300 ml) and ice (300 ml). The precipitated solid was collected by filtration to give the title compound (29 g, 74%) as a brown solid. MS (ES+) $C_{11}H_9BrN_4O$ requires: 292, found: 293 [M+H]$^+$.

Step 6: Tert-butyl 3-(6-(2-(pyridin-2-yl)acetamido) pyridazin-3-yl)-2H-pyrrole-1(5H)-carboxylate

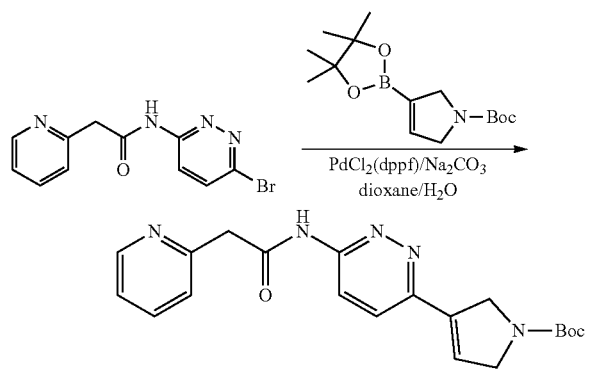

A mixture of N-(6-bromopyridazin-3-yl)-2-(pyridin-2-yl) acetamide (25.6 g, 87.4 mmol), tert-butyl 4-(4,4,5,5-tetramethyl-1,3,2-dioxaborolan-2-yl)-2,3-dihydropyrrole-1-carboxylate (38.6 g, 131 mmol), Na$_2$CO$_3$ (37 g, 350 mmol) and Pd(dppf)C$_{1-2}$ (6.0 g, 8.2 mmol) in 1,4-dioxane (500 ml) and H$_2$O (25 ml) was heated at 110° C. overnight under Ar. The reaction was cooled to RT, diluted with water, and extracted with EtOAc. The organic layer was washed with brine, dried and concentrated. The residue was purified via silica gel chromatography (2-5% MeOH in DCM) to give the title compound as a beige solid (17.2 g, 52%). MS (ES+) $C_{20}H_{23}N_5O_3$ requires: 381, found: 382 [M+H]$^+$.

Step 7: Tert-butyl 3-(6-(2-(pyridin-2-yl)acetamido) pyridazin-3-yl)pyrrolidine-1-carboxylate

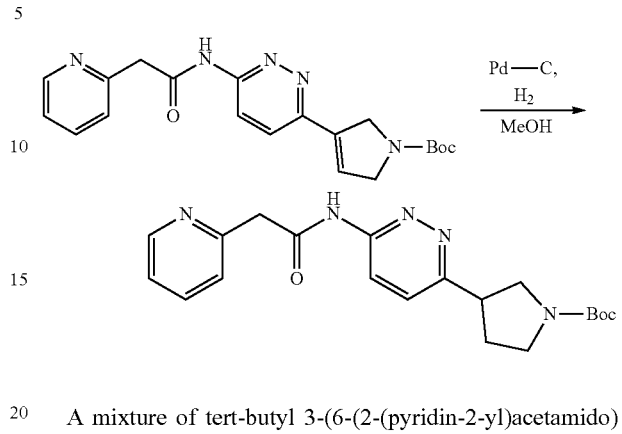

A mixture of tert-butyl 3-(6-(2-(pyridin-2-yl)acetamido) pyridazin-3-yl)-2H-pyrrole-1(5H)-carboxylate (7.0 g, 18 mmol) and Pd/C (3 g) in MeOH (1400 ml) was stirred at RT overnight under H$_2$. The mixture was filtered and the filtrate was concentrated to afford the title compound as a brown oil (6.5 g, 93%). MS (ES+) $C_{20}H_{25}N_5O_3$ requires: 383, found: 384 [M+H]$^+$.

Step 8: (S)-tert-butyl 3-(6-(2-(pyridin-2-yl)acetamido)pyridazin-3-yl)pyrrolidine-1-carboxylate & (R)-tert-butyl 3-(6-(2-(pyridin-2-yl)acetamido) pyridazin-3-yl)pyrrolidine-1-carboxylate

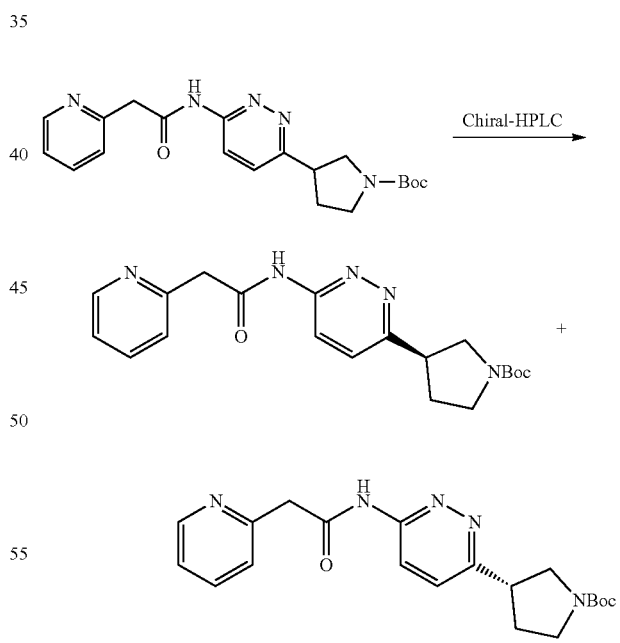

Tert-butyl 3-(6-(2-(pyridin-2-yl)acetamido)pyridazin-3-yl)pyrrolidine-1-carboxylate (1.0 g) was separated by chiral SFC (Thar/Waters SFC-80, column: OJ 4.6×250 mm, 80:20 CO$_2$/MeOH with 0.2% NH$_3$, 80 g/min flow rate) to give the title compounds as off-white solids (1st eluting: 270 mg, 27%; 2nd eluting: 230 mg, 23%).

Step 9: (R)-2-(pyridin-2-yl)-N-(6-(pyrrolidin-3-yl)pyridazin-3-yl)acetamide

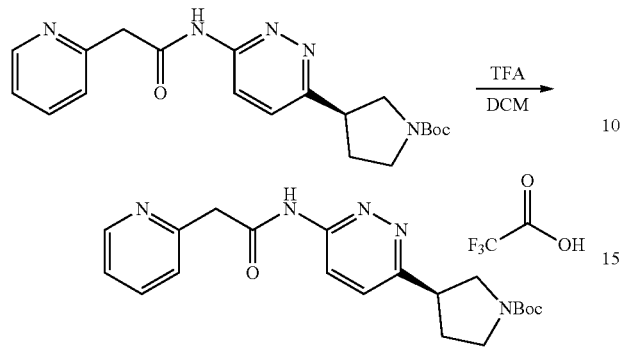

A mixture of tert-butyl 3-(6-(2-(pyridin-2-yl)acetamido)pyridazin-3-yl)pyrrolidine-1-carboxylate (230 mg, 0.60 mmol, 1st eluting product from step 8) and TFA (1 ml) in DCM (1 ml) was stirred at RT for 2 hrs. The reaction mixture was concentrated to afford the title compound as a brown oil (238 mg, 100%, TFA salt) which was used in the next step without purification. MS (ES+) $C_{15}H_{17}N_5O$ requires: 283, found: 284 [M+H]$^+$.

To determine the absolute stereochemistry of the two enantiomers, the Mosher amide protocol was followed according to Hoye, T. R. & Renner, M. K., J. Org. Chem. 1996, 61, 2056-2064 and J. Org. Chem. 1996, 61, 8489-8495.

Step 9a: 2-(pyridin-2-yl)-N-(6-((R)-1-((S)-3,3,3-trifluoro-2-methoxy-2-phenylpropanoyl) pyrrolidin-3-yl)pyridazin-3-yl)acetamide (S-Mosher amide)

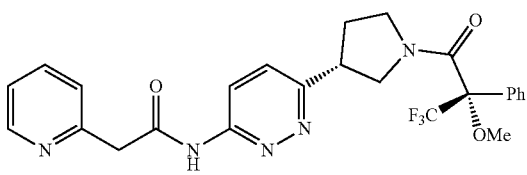 [SMILES: CO[C@](C(=O)N1CC[C@@H](c2ccc(NC(=O)Cc3ccccn3)nn2)C1)(c1ccccc1)C(F)(F)F]

To a solution of 2-(pyridin-2-yl)-N-(6-(pyrrolidin-3-yl)pyridazin-3-yl)acetamide 2,2,2-trifluoroacetate (25 mg, 0.063 mmol) and DIEA (38 µl, 0.22 mmol) in CH$_2$Cl$_2$ (629 µl) at RT was added (R)-3,3,3-trifluoro-2-methoxy-2-phenylpropanoyl chloride (29.4 µl, 0.157 mmol) and the resulting mixture was stirred at RT for 1 hr. The volatiles were removed under reduced pressure. The residue was purified by mass-triggered preparative HPLC (Mobile phase: A=0.1% TFA/H$_2$O, B=0.1% TFA/MeCN; Gradient: B=30-70%; 12 min; Column: C18) to give the title compound as a pale yellow solid (TFA salt, ~90% purity). The product was repurified via silica gel chromatography (0-100% EtOAc (with 10% MeOH) in hexanes) to give the title compound (23 mg, 73%) as a colorless amorphous material. MS (ES+) $C_{25}H_{24}F_3N_5O_3$ requires: 499, found: 500 [M+H]$^+$. $^1$H NMR (500 MHz, Chloroform-d, ~1:1 mixture of syn/anti rotomers) δ 11.12 (brs, 0.5H), 11.07 (brs, 0.5H), 8.67 (dd, J=5.0, 1.0 Hz, 1H), 8.43 (d, J=9.2 Hz, 0.5H, anti), 8.20 (d, J=9.2 Hz, 0.5H, syn), 7.74-7.68 (m, 1H), 7.58-7.52 (m, 1H), 7.45-7.36 (m, 2.5H), 7.33-7.20 (m, 4H), 6.74 (d, J=9.2 Hz, 0.5H, syn), 4.13 (dd, J=12.6, 7.9 Hz, 0.5H, anti), 3.97 (s, 2H), 3.96-3.87 (m, 1H), 3.82 (dd, J=11.9, 6.9 Hz, 0.5H, syn), 3.73-3.60 (m, 4H), 3.57-3.51 (m, 0.5H, syn), 3.48-3.41 (m, 0.5H, anti), 2.92 (dd, J=11.8, 6.3 Hz, 0.5H, syn), 2.64 (dt, J=11.5, 7.3 Hz, 0.5H, anti), 2.28-2.14 (m, 1.5H), 2.08 (dtd, J=12.5, 7.0, 5.6 Hz, 0.5H, anti).

Step 9b: 2-(pyridin-2-yl)-N-(6-((R)-1-((R)-3,3,3-trifluoro-2-methoxy-2-phenylpropanoyl) pyrrolidin-3-yl)pyridazin-3-yl)acetamide (R-Mosher amide)

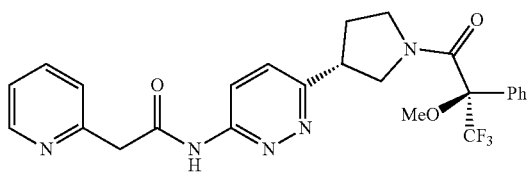 [SMILES: CO[C@@](C(=O)N1CC[C@@H](c2ccc(NC(=O)Cc3ccccn3)nn2)C1)(c1ccccc1)C(F)(F)F]

Using the procedure for the S-Mosher amide above, starting with (S)-3,3,3-trifluoro-2-methoxy-2-phenylpropanoyl chloride (39.7 mg, 0.157 mmol), the title compound was obtained as colorless amorphous material (8.0 mg, 26%). MS (ES+) $C_{25}H_{24}F_3N_5O_3$ requires: 499, found: 500 [M+H]$^+$. $^1$H NMR (500 MHz, Chloroform-d, ~1:1 mixture of syn/anti rotomers) δ 11.12 (br s, 0.5H, syn), 11.08 (brs, 0.5H, anti), 8.70-8.64 (m, 1H), 8.40 (d, J=9.2 Hz, 0.5H, anti), 8.37 (d, J=9.2 Hz, 0.5H, syn), 7.74-7.68 (m, 1H), 7.57-7.51 (m, 2H), 7.40-7.35 (m, 3H), 7.31-7.24 (m, 1.5H), 7.17 (d, J=9.2 Hz, 0.5H, syn), 4.12 (dd, J=12.5, 8.0 Hz, 0.5H, anti), 3.96 (s, 1H, anti), 3.94 (s, 1H, syn), 3.93-3.89 (m, 0.5H, syn), 3.86 (dd, J=12.5, 8.9 Hz, 0.5H, anti), 3.76-3.69 (m, 1.5H), 3.65-3.60 (m, 1.5H), 3.59-3.52 (m, 0.5H, anti), 3.39 (ddd, J=11.6, 9.6, 6.6 Hz, 0.5H, anti), 3.29 (dd, J=11.6, 7.3 Hz, 0.5H, syn), 3.20 (tt, J=9.5, 6.9 Hz, 0.5H, syn), 3.02 (ddd, J=11.4, 7.8, 3.3 Hz, 0.5H, anti), 2.30-2.09 (m, 1.5H), 2.01-1.90 (m, 0.5H, anti).

Proton assignments for $H_1$-$H_8$ were made using DEPT, COSY, NOESY, and HSQC spectra in combination with expected chemical shift predictions (ChemDraw Professional, v15.0). Syn/anti rotomers were grouped using this data and the assumption that the Mosher amide phenyl ring would shift adjacent protons upfield, specifically, for the (S)-Mosher amide: syn=$H_{2(down)}$ shielded and anti=$H_{5(Up)}$ shielded; for the (R)-Mosher amide: syn=$H_{2(up)}$ shielded and anti=$H_{5(down)}$ shielded.

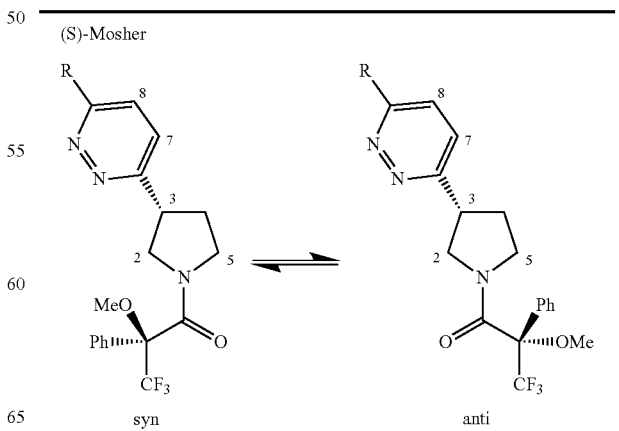

(S)-Mosher

87

-continued (R)-Mosher

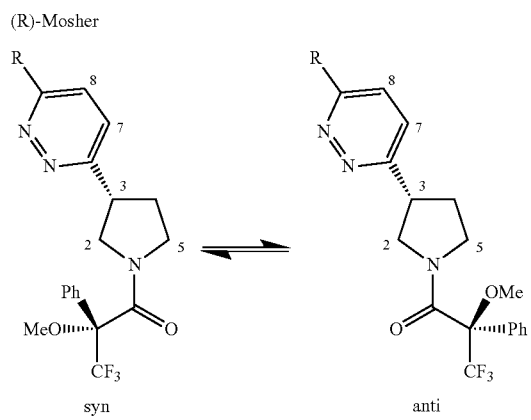

| H | (S)-syn | (S)-anti | (R)-syn | (R)-anti | syn δ (S-R) | anti δ (S-R) |
|---|---------|----------|---------|----------|-------------|--------------|
| 2up | 3.82 | 4.12 | 3.28 | 4.11 | 0.54 | 0.01 |
| 2down | 2.91 | 3.89 | 3.62 | 3.85 | −0.71 | 0.04 |
| 3 | 3.53 | 3.44 | 3.19 | 3.55 | 0.34 | −0.11 |
| 4 | 2.23 | 2.19 | 2.24 | 2.18 | −0.01 | 0.01 |
| 4 | 2.23 | 2.07 | 2.15 | 1.95 | 0.08 | 0.12 |
| 5up | 3.91 | 2.64 | 3.91 | 3.38 | 0 | −0.74 |
| 5down | 3.69 | 3.63 | 3.71 | 3.00 | −0.02 | 0.63 |
| 7 | 6.74 | 7.30 | 7.17 | 7.28 | −0.43 | 0.02 |
| 8 | 8.12 | 8.42 | 8.36 | 8.40 | −0.24 | 0.02 |

Using the Mosher amide protocol, calculated δ(S—R) values were largest in the syn rotomers at $H_2$, $H_3$, and $H_{7/8}$, whereas with the anti rotomer only $H_5$ was significantly affected. These values are in agreement with the stereochemistry at $H_3$ being (R) as drawn.

Step 10: (R)-5-(3-(6-(2-(pyridin-2-yl)acetamido)pyridazin-3-yl)pyrrolidin-1-yl)-N-((4-(trifluoromethyl)pyridin-2-yl) methyl)-1,3,4-thiadiazole-2-carboxamide

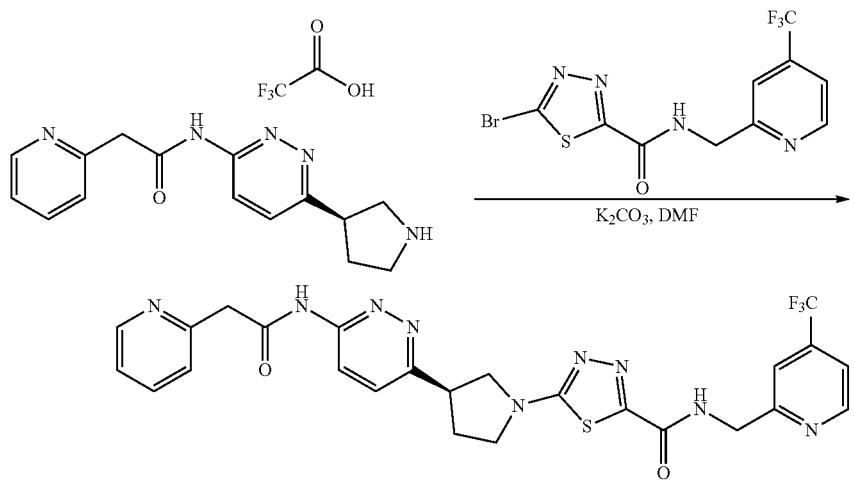

A mixture of (R)-2-(pyridin-2-yl)-N-(6-(pyrrolidin-3-yl)pyridazin-3-yl)acetamide 2,2,2-trifluoroacetatee (240 mg, 0.60 mmol), 5-bromo-N-((4-(trifluoromethyl)pyridin-2-yl)methyl)-1,3,4-thiadiazole-2-carboxamide (184 mg, 0.500 mmol) and $K_2CO_3$ (276 mg, 2.00 mmol) in DMF (3 ml) was stirred at 40° C. overnight. The reaction mixture was diluted with EtOAc and wash successively with water and brine. The organic layer was dried and concentrated. The crude product was washed with EtOAc to afford the title compound as a beige solid (230 mg, 81%). MS (ES+) $C_{25}H_{22}F_3N_9O_2S$ requires: 569, found: 570 [M+H]$^+$. $^1$H NMR (500 MHz, DMSO) δ 11.37 (s, 1H), 9.44 (t, J=6.0 Hz, 1H), 8.82 (d, J=4.9 Hz, 1H), 8.51 (d, J=4.4 Hz, 1H), 8.29 (d, J=9.2 Hz, 1H), 7.78-7.67 (m, 4H), 7.41 (d, J=7.8 Hz, 1H), 7.29 (dd, J=6.9, 5.4 Hz, 1H), 4.67 (d, J=6.0 Hz, 2H), 4.08-3.87 (m, 4H), 3.85-3.77 (m, 1H), 3.75-3.60 (m, 2H), 2.60-2.52 (m, 1H), 2.39-2.25 (m, 1H). Chiral HPLC analysis (50:50 EtOH/Hexanes with 0.1% diethylamine, column: ChiralPak IA, 4.6×250 mm, 5 uM, 1.0 ml/min, temperature: 40° C.): >99% ee, $R_t$=18.2 min.

Example 45: (S)-5-(3-(6-(2-(pyridin-2-yl)acetamido)pyridazin-3-yl)pyrrolidin-1-yl)-N-(pyridin-2-ylmethyl)-1,3,4-thiadiazole-2-carboxamide

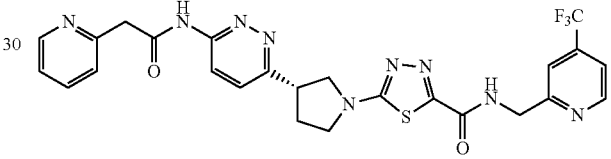

Using the procedure from Example 44, steps 9 and 10, starting from (S)-tert-butyl 3-(6-(2-(pyridin-2-yl)acetamido)pyridazin-3-yl)pyrrolidine-1-carboxylate (230 mg, 0.60 mmol, 2nd eluting product from Example 44, step 8), the title compound was obtained as a beige solid (250 mg, 73%). MS (ES+) $C_{25}H_{22}F_3N_9O_2S$ requires: 569, found: 570 [M+H]$^+$. Chiral HPLC analysis (50:50 EtOH/Hexanes with 0.1% diethylamine, column: ChiralPak IA, 4.6×250 mm, 5 uM, 1.0 ml/min, temperature: 40° C.): >99% ee, $R_t$=14.3 min.

Example 46: (R)-5-(3-(6-(2-(pyridin-2-yl)acetamido)pyridazin-3-yl)pyrrolidin-1-yl)-N-(pyridin-2-ylmethyl)-1,3,4-thiadiazole-2-carboxamide

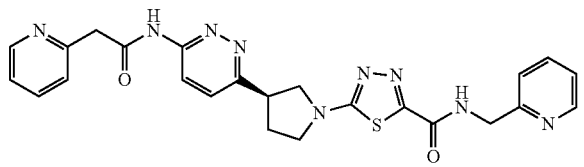 [SMILES: O=C(Cc1ccccn1)Nc1ccc([C@@H]2CCN(c3nnc(C(=O)NCc4ccccn4)s3)C2)nn1]

Step 1: 5-bromo-N-(pyridin-2-ylmethyl)-1,3,4-thiadiazole-2-carboxamide

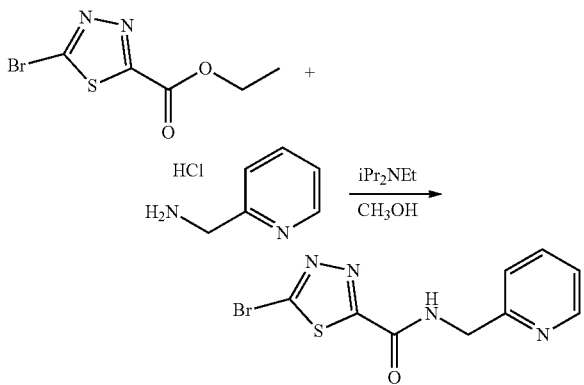

To a solution of ethyl 5-bromo-1,3,4-thiadiazole-2-carboxylate (150 mg, 0.633 mmol) and pyridin-2-ylmethanamine hydrochloride (91 mg, 0.63 mmol) in MeOH (2.5 ml) was added iPr₂NEt (276 µl, 1.58 mmol) and the resulting mixture was stirred at RT for 2 hrs. The mixture was concentrated. The residue was purified via silica gel chromatography (0-100% EtOAc (with 10% MeOH) in hexanes) to give the title compound (169 mg, 89%) as a white solid. MS (ES+) $C_9H_7BrN_4OS$ requires: 298, found: 299 [M+H]⁺.

Step 2: (R)-5-(3-(6-(2-(pyridin-2-yl)acetamido)pyridazin-3-yl)pyrrolidin-1-yl)-N-(pyridin-2-ylmethyl)-1,3,4-thiadiazole-2-carboxamide

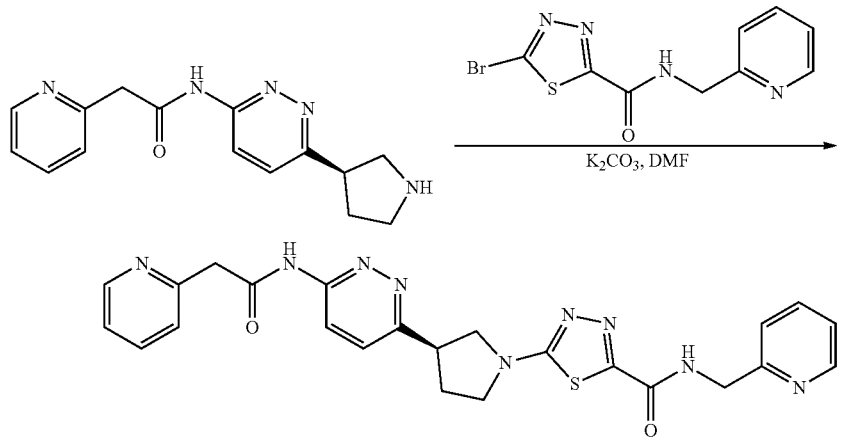

To a suspension of (R)-2-(pyridin-2-yl)-N-(6-(pyrrolidin-3-yl)pyridazin-3-yl)acetamide dihydrochloride (50 mg, 0.14 mmol) in DMF (638 µl) was added 5-bromo-N-(pyridin-2-ylmethyl)-1,3,4-thiadiazole-2-carboxamide (38 mg, 0.13 mmol) and potassium carbonate (70 mg, 0.51 mmol) and the resulting mixture was stirred at 40° C. for 12 hrs. The reaction mixture was diluted with EtOAc (3 ml) and washed with water (3 ml) and brine (3 ml) before drying over MgSO₄. The volatiles were removed under reduced pressure. The residue was purified via silica gel chromatography (0-10% MeOH in DCM with 0.5% NH₄OH) to give the title compound (25 mg, 39%) as a yellow solid. MS (ES+) $C_{24}H_{23}N_9O_2S$ requires: 501, found: 502 [M+H]⁺. ¹H NMR (600 MHz, DMSO-d₆) δ 11.36 (s, 1H), 9.31 (t, J=6.1 Hz, 1H), 8.56-8.47 (m, 2H), 8.28 (d, J=9.2 Hz, 1H), 7.79-7.71 (m, 3H), 7.41 (d, J=7.8 Hz, 1H), 7.32 (d, J=7.8 Hz, 1H), 7.30-7.25 (m, 2H), 4.55 (d, J=6.0 Hz, 2H), 4.04-3.98 (m, 3H), 3.98-3.90 (m, 1H), 3.80 (dd, J=9.8, 7.7 Hz, 1H), 3.75-3.68 (m, 1H), 3.68-3.60 (m, 1H), 2.57-2.51 (m, 1H), 2.36-2.26 (m, 1H).

Example 47: (R)—N-((4-cyclopropylpyridin-2-yl)methyl)-5-(3-(6-(2-(pyridin-2-yl)acetamido)pyridazin-3-yl)pyrrolidin-1-yl)-1,3,4-thiadiazole-2-carboxamide

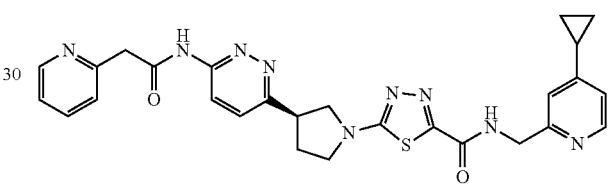

Step 1: (4-cyclopropylpyridin-2-yl)methanamine

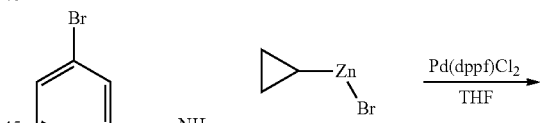

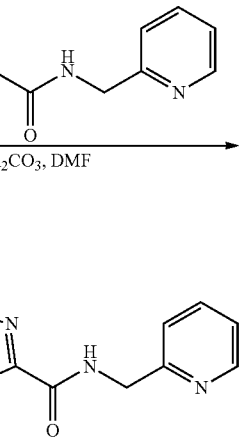

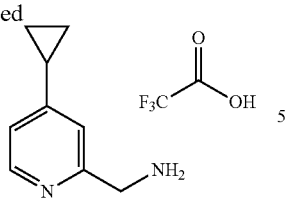

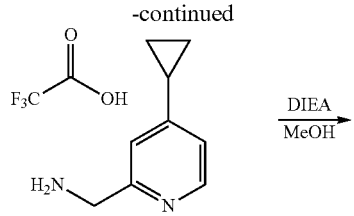

A degassed solution of (4-bromopyridin-2-yl)methanamine (200 mg, 1.07 mmol), cyclopropylzinc(II) bromide (10.7 ml, 5.35 mmol, 0.5 M in THF) and PdCl$_2$(dppf)-CH$_2$Cl$_{1-2}$ adduct (44 mg, 0.054 mmol) was stirred at 65° C. for 3 hrs. The volatiles were removed under reduced pressure. The residue was purified by mass-triggered preparative HPLC (Mobile phase: A=0.1% TFA/H$_2$O, B=0.1% TFA/MeCN; Gradient: B=0-30%; 20 min; Column: C18) to give the title compound (99 mg, 35%, TFA salt) as an off-white solid. MS (ES+) C$_9$H$_{12}$N$_2$ requires: 148, found: 149 [M+H]$^+$.

Step 2: 5-bromo-N-((4-cyclopropylpyridin-2-yl)methyl)-1,3,4-thiadiazole-2-carboxamide

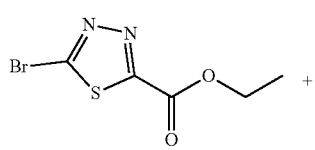

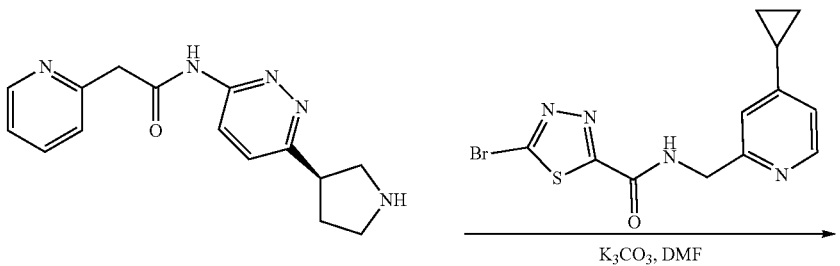

Using the procedure in Example 46, step 1 the title compound was obtained as a pale yellow solid (101 mg, 78%). MS (ES+) C$_{12}$H$_{11}$BrN$_4$OS requires: 338, found: 339 [M+H]$^+$.

Step 3: (R)—N-((4-cyclopropylpyridin-2-yl)methyl)-5-(3-(6-(2-(pyridin-2-yl)acetamido)pyridazin-3-yl)pyrrolidin-1-yl)-1,3,4-thiadiazole-2-carboxamide

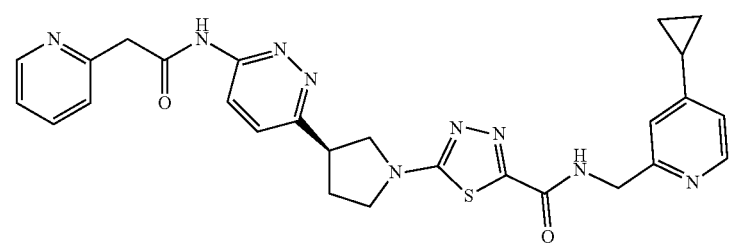

Using the procedure in Example 46, step 2 the title compound was obtained as a yellow solid (7 mg, 9%). MS (ES+) $C_{27}H_{27}N_9O_2S$ requires: 541, found: 542 $[M+H]^+$. $^1H$ NMR (600 MHz, DMSO-$d_6$) δ 11.36 (s, 1H), 9.22 (t, J=6.1 Hz, 1H), 8.51 (d, J=3.4 Hz, 1H), 8.32 (d, J=5.2 Hz, 1H), 8.28 (d, J=9.2 Hz, 1H), 7.80-7.72 (m, 2H), 7.41 (d, J=7.8 Hz, 1H), 7.28 (dd, J=7.4, 4.9 Hz, 1H), 7.07 (s, 1H), 6.96 (d, J=3.6 Hz, 1H), 4.49 (d, J=5.6 Hz, 2H), 4.03-3.98 (m, 3H), 3.98-3.90 (m, 1H), 3.80 (dd, J=9.8, 7.6 Hz, 1H), 3.74-3.67 (m, 1H), 3.67-3.61 (m, 1H), 2.57-2.51 (m, 1H), 2.36-2.26 (m, 1H), 1.97-1.87 (m, 1H), 1.09-1.01 (m, 2H), 0.80-0.72 (m, 2H).

Example 48: (R)—N-((6-methyl-4-(trifluoromethyl) pyridin-2-yl)methyl)-5-(3-(6-(2-(pyridin-2-yl)acet- amido)pyridazin-3-yl)pyrrolidin-1-yl)-1,3,4-thiadiaz- ole-2-carboxamide

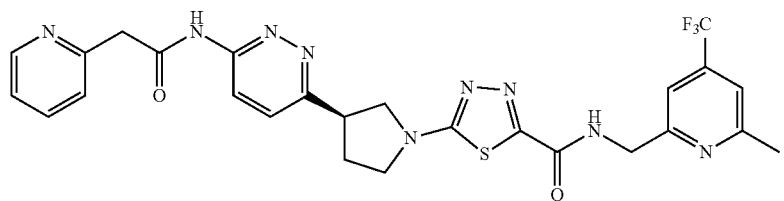 [SMILES: Cc1cc(C(F)(F)F)cc(CNC(=O)c2nnc(N3CC[C@@H](c4ccc(NC(=O)Cc5ccccn5)nn4)C3)s2)n1]

Step 1: Tert-butyl ((6-methyl-4-(trifluoromethyl) pyridin-2-yl)methyl)carbamate

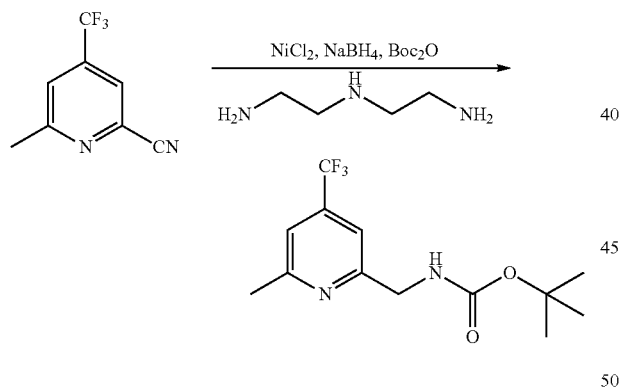

To a solution of 6-methyl-4-(trifluoromethyl)picolinoni- trile (100 mg, 0.537 mmol, prepared according to EP 1362850 A1, 2003, p. 38), di-tert-butyl dicarbonate (176 mg, 0.806 mmol) and nickel(II) chloride hexahydrate (31.9 mg, 0.134 mmol) in MeOH (2.7 ml) at 0° C. was added NaBH$_4$ (81 mg, 2.1 mmol) portionwise. The resulting mixture was stirred at 0° C. for 30 min and allowed to warm to RT. N1-(2-aminoethyl)ethane-1,2-diamine (58 μl, 0.54 mmol) was then added, stirred at RT for 30 min, and concentrated. The residue was partitioned between EtOAc (6 ml) and water (6 ml). The organic layer was separated and washed with aq. NaHCO$_3$ (6 ml), brine (6 ml), and dried over MgSO$_4$. The volatiles were removed under reduced pres- sure. The residue was purified via silica gel chromatography (0-100% EtOAc in hexanes) to give the title compound (138 mg, 88%) as a pale yellow liquid. MS (ES+) $C_{13}H_{17}F_3N_2O_2$ requires: 290, found: 235 $[M-tBu+H]^+$.

Step 2: (6-methyl-4-(trifluoromethyl)pyridin-2-yl) methanamine hydrochloride

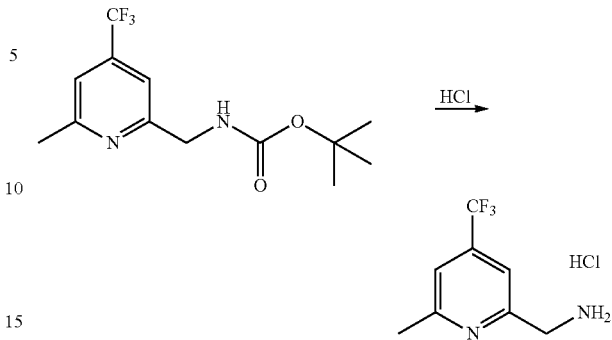

HCl in dioxane (538 μl, 2.15 mmol, 4M in dioxane) was added to tert-butyl ((6-methyl-4-(trifluoromethyl)pyridin-2- yl)methyl)carbamate (125 mg, 0.431 mmol) at RT and the resulting solution was allowed to stir for 1 hr. The reaction mixture was concentrated and the residue was triturated with Et$_2$O (2×4 ml) to give the title compound (98 mg, 100%) as an off-white solid. MS (ES+) $C_8H_9F_3N_2$ requires: 190, found: 191 $[M+H]^+$.

Step 3: 5-bromo-N-((6-methyl-4-(trifluoromethyl) pyridin-2-yl)methyl)-1,3,4-thiadiazole-2-carboxam- ide

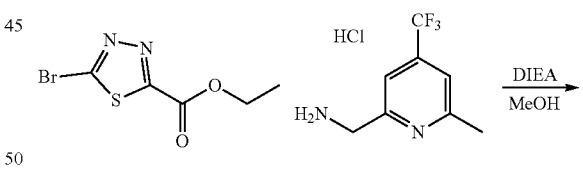

Using the procedure in Example 46, step 1 the title compound was obtained as an off-white solid (106 mg, 67%). MS (ES+) $C_{11}H_8BrF_3N_4OS$ requires: 380, found: 381 $[M+H]^+$.

Step 4: (R)—N-((6-methyl-4-(trifluoromethyl)pyridin-2-yl)methyl)-5-(3-(6-(2-(pyridin-2-yl)acetamido)pyridazin-3-yl)pyrrolidin-1-yl)-1,3,4-thiadiazole-2-carboxamide

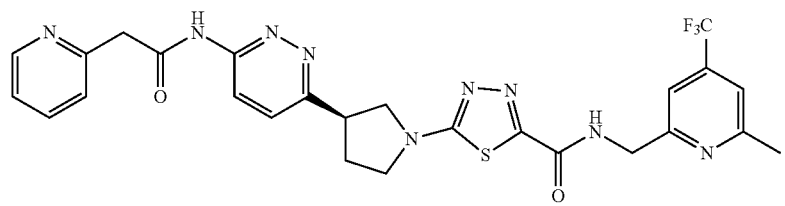 [SMILES: Cc1cc(C(F)(F)F)cc(CNC(=O)c2nnc(N3CC[C@@H](c4ccc(NC(=O)Cc5ccccn5)nn4)C3)s2)n1]

Using the procedure in Example 46, step 2 the title compound was obtained as a yellow solid (24 mg, 32%). MS (ES+) $C_{26}H_{24}F_3N_9O_2S$ requires: 583, found: 584 $[M+H]^+$. $^1$H NMR (600 MHz, DMSO-$d_6$) δ 11.36 (s, 1H), 9.43 (t, J=6.2 Hz, 1H), 8.51 (d, J=4.9 Hz, 1H), 8.28 (d, J=9.2 Hz, 1H), 7.79-7.72 (m, 2H), 7.55 (s, 1H), 7.43-7.38 (m, 2H), 7.28 (dd, J=7.4, 5.1 Hz, 1H), 4.60 (d, J=6.1 Hz, 2H), 4.03-3.97 (m, 3H), 3.97-3.90 (m, 1H), 3.80 (dd, J=9.9, 7.6 Hz, 1H), 3.73-3.67 (m, 1H), 3.67-3.61 (m, 1H), 2.58 (s, 3H), 2.56-2.51 (m, 1H), 2.35-2.27 (m, 1H).

Example 49: 5-(3-(6-(2-(6-methylpyridin-2-yl)acetamido)pyridazin-3-yl)pyrrolidin-1-yl)-N-((4-(trifluoromethyl)pyridin-2-yl)methyl)-1,3,4-thiadiazole-2-carboxamide

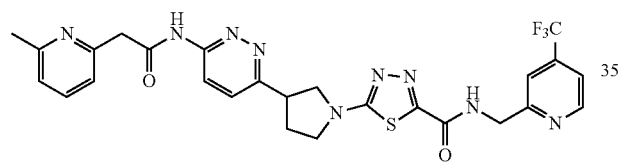

Steps 1-5

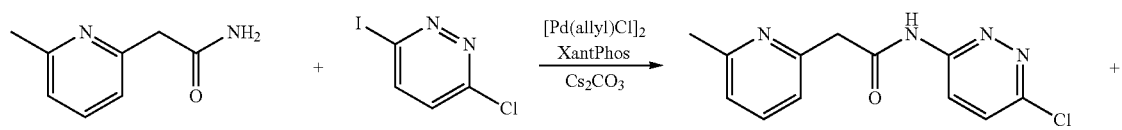

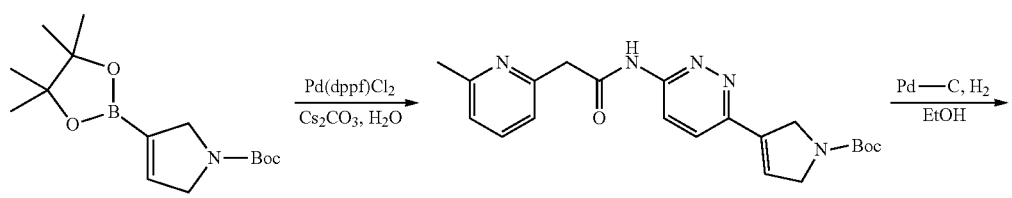

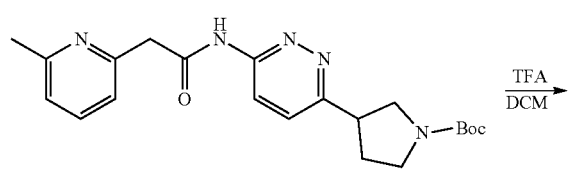

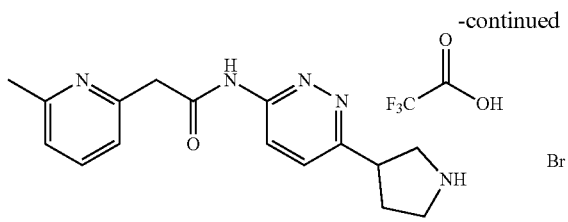
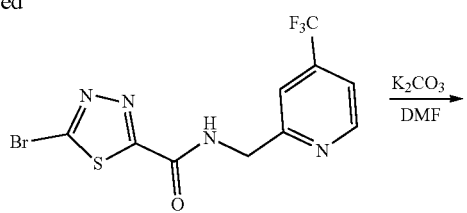

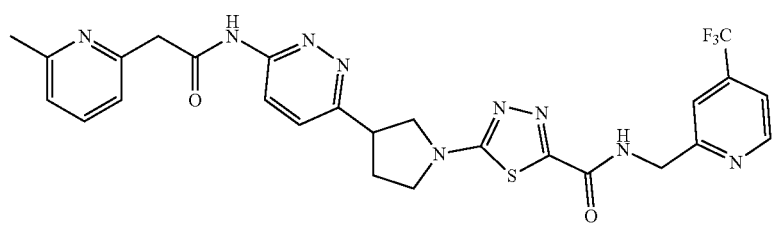

Step 1: A-(6-chloropyridazin-3-yl)-2-(6-methylpyridin-2-yl)acetamide

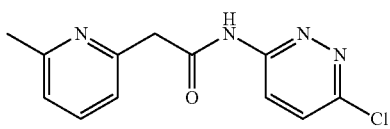 [SMILES: Cc1cccc(CC(=O)Nc2ccc(Cl)nn2)n1]

A vial (20 ml, teflon septa) was charged with 2-(6-methylpyridin-2-yl)acetamide (200 mg, 1.33 mmol), 3-chloro-6-iodopyridazine (352 mg, 1.46 mmol), cesium carbonate (868 mg, 2.66 mmol), allylpalladium chloride dimer (24 mg, 0.067 mmol), Xantphos (154 mg, 0.266 mmol), and Dioxane (6.6 ml). The mixture was degassed by bubbling $N_2$ through the suspension for 5 min and then heated at 50° C. with stirring for 12 hrs. The reaction was filtered and the volatiles were removed under reduced pressure. The residue was purified via silica gel chromatography (0-100% EtOAc (with 10% MeOH) in hexanes) to give the title compound (283 mg, 81%) as a brown amorphous material. MS (ES+) $C_{12}H_{11}ClN_4O$ requires: 262, found: 285 [M+Na]+.

Step 2: Tert-butyl 3-(6-(2-(6-methylpyridin-2-yl)acetamido)pyridazin-3-yl)-2,5-dihydro-1H-pyrrole-1-carboxylate

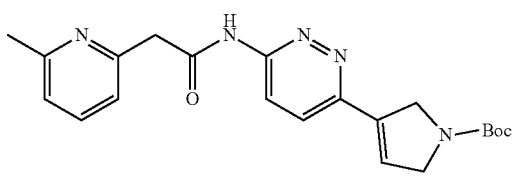 [SMILES: Cc1cccc(CC(=O)Nc2ccc(C3=CCN(C(=O)OC(C)(C)C)C3)nn2)n1]

To a vial (20 ml, teflon septa) containing A-(6-chloropyridazin-3-yl)-2-(6-methylpyridin-2-yl)acetamide (200 mg, 0.761 mmol), tert-butyl 3-(4,4,5,5-tetramethyl-1,3,2-dioxaborolan-2-yl)-2,5-dihydro-1H-pyrrole-1-carboxylate (337 mg, 1.14 mmol), $Cs_2CO_3$ (248 mg, 0.761 mmol) and $PdCl_2$(dppf)-CH2Cl adduct (62 mg, 0.076 mmol) was added dioxane (3.8 ml) and water (69 µl, 3.8 mmol). The reaction mixture was purged with $N_2$ for 5 min and stirred at 50° C. overnight. The reaction mixture was cooled, diluted with DCM (10 ml), and filtered. The volatiles were removed under reduced pressure. The residue was purified via flash chromatography (0-100% EtOAc (with 10% MeOH) in Hexanes) to give the title compound (151 mg, 50%) as a brown solid. MS (ES+) $C_{21}H_{25}N_5O_3$ requires: 395, found: 396 [M+H]+.

Step 3: Tert-butyl 3-(6-(2-(6-methylpyridin-2-yl)acetamido)pyridazin-3-yl)pyrrolidine-1-carboxylate

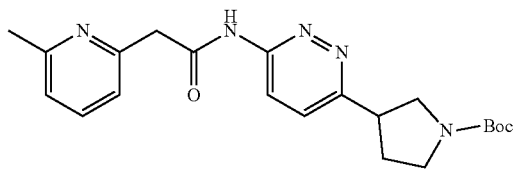 [SMILES: Cc1cccc(CC(=O)Nc2ccc(C3CCN(C(=O)OC(C)(C)C)C3)nn2)n1]

A reaction vessel was charged with 10% Pd—C (81 mg, 0.076 mmol), tert-butyl 3-(6-(2-(6-methylpyridin-2-yl)acetamido)pyridazin-3-yl)-2,5-dihydro-1H-pyrrole-1-carboxylate (150 mg, 0.379 mmol) and Ethanol (3.8 ml) under an atmosphere of $N_2$. The suspension was degassed with $N_2$ for 5 minutes and purged with $H_2$ for 5 minutes. The reaction mixture was stirred under an atmosphere of $H_2$ at 1 atm for 2 hrs at 40° C. The reaction mixture was purged with $N_2$, filtered through Celite, and concentrated under reduced pressure. The residue was purified via silica gel chromatography (0-10% DCM in MeOH with 0.5% $NH_4OH$) to give the title compound (126 mg, 84%) as an orange amorphous material. MS (ES+) $C_{21}H_{27}N_5O_3$ requires: 397, found: 398 [M+H]+.

Step 4: 2-(6-methylpyridin-2-yl)-N-(6-(pyrrolidin-3-yl)pyridazin-3-yl)acetamide 2,2,2-trifluoroacetate

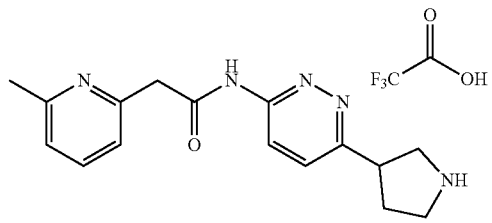

To a solution of tert-butyl 3-(6-(2-(6-methylpyridin-2-yl)acetamido)pyridazin-3-yl)pyrrolidine-1-carboxylate (120 mg, 0.302 mmol) in CH$_2$Cl$_2$ (604 µl) was added trifluoroacetic acid (581 µl, 7.55 mmol) and the resulting mixture was stirred at RT for 30 min. The volatiles were removed under reduced pressure to give the title compound (124 mg, 100%) as a brown oil. MS (ES+) C$_{16}$H$_{19}$N$_5$O requires: 297, found: 298 [M+H]$^+$.

Step 5: 5-(3-(6-(2-(6-methylpyridin-2-yl)acetamido)pyridazin-3-yl)pyrrolidin-1-yl)-N-((4-(trifluoromethyl)pyridin-2-yl)methyl)-1,3,4-thiadiazole-2-carboxamide

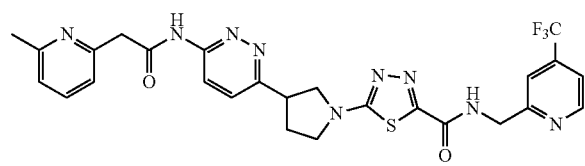 [SMILES: Cc1cccc(CC(=O)Nc2ccc(C3CCN(c4nnc(C(=O)NCc5cc(C(F)(F)F)ccn5)s4)C3)nn2)n1]

Using the procedure in Example 46, step 2 the title compound was obtained as an off-white solid (42 mg, 71%). MS (ES+) C$_{26}$H$_{24}$F$_3$N$_9$O$_2$S requires: 583, found: 584 [M+H]$^+$; $^1$H NMR (600 MHz, DMSO-d$_6$) δ 11.38 (s, 1H), 9.44 (t, J=6.1 Hz, 1H), 8.81 (d, J=5.0 Hz, 1H), 8.27 (s, 1H), 7.74 (d, J=9.2 Hz, 1H), 7.70-7.63 (m, 3H), 7.20 (d, J=7.6 Hz, 1H), 7.14 (d, J=7.7 Hz, 1H), 4.66 (d, J=6.0 Hz, 2H), 4.04-3.98 (m, 1H), 3.97-3.90 (m, 3H), 3.85-3.78 (m, 1H), 3.74-3.68 (m, 1H), 3.68-3.61 (m, 1H), 2.57-2.51 (m, 1H), 2.45 (s, 3H), 2.36-2.26 (m, 1H).

Example 50: 5-(3-(6-(2-(6-methylpyridin-2-yl)acetamido)pyridazin-3-yl)pyrrolidin-1-yl)-N-((6-methylpyridin-2-yl)methyl)-1,3,4-thiadiazole-2-carboxamide

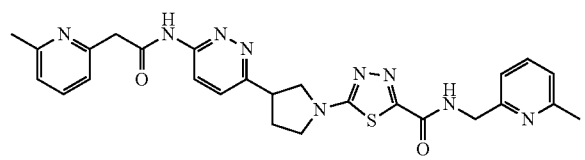

Step 1: 5-bromo-N-((6-methylpyridin-2-yl)methyl)-1,3,4-thiadiazole-2-carboxamide

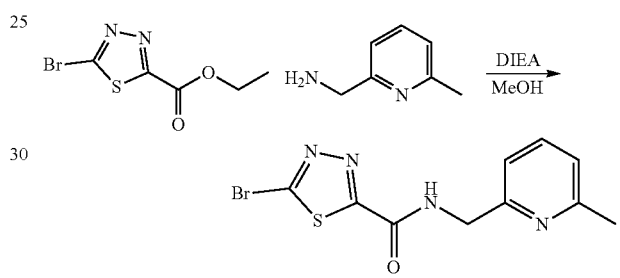

Using the procedure in Example 46, step 1 the title compound was obtained as a yellow liquid (117 mg, 59%). MS (ES+) C$_{10}$H$_9$BrN$_4$OS requires: 312, found: 313 [M+H]$^+$.

Step 2: 5-(3-(6-(2-(6-methylpyridin-2-yl)acetamido)pyridazin-3-yl)pyrrolidin-1-yl)-N-((6-methylpyridin-2-yl)methyl)-1,3,4-thiadiazole-2-carboxamide

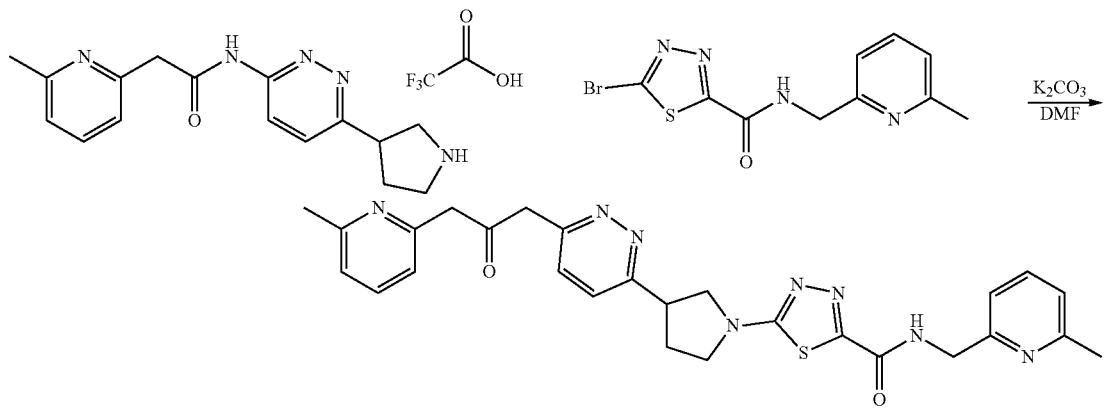

Using the procedure in Example 46, step 2 the title compound was obtained as a pale yellow amorphous material (22 mg, 41%). MS (ES+) C$_{26}$H$_{27}$N$_9$O$_2$S requires: 529, found: 530 [M+H]⁺. ¹H NMR (600 MHz, DMSO-d₆) δ 11.38 (s, 1H), 9.32 (t, J=6.1 Hz, 1H), 8.28 (d, J=9.2 Hz, 1H), 7.74 (d, J=9.3 Hz, 1H), 7.67-7.61 (m, 2H), 7.20 (d, J=7.6 Hz, 1H), 7.13 (t, J=8.3 Hz, 2H), 7.10 (d, J=7.7 Hz, 1H), 4.49 (d, J=6.1 Hz, 2H), 4.03-3.97 (m, 1H), 3.97-3.91 (m, 3H), 3.80 (dd, J=9.8, 7.7 Hz, 1H), 3.73-3.67 (m, 1H), 3.67-3.60 (m, 1H), 2.57-2.51 (m, 1H), 2.45 (s, 3H), 2.45 (s, 3H), 2.35-2.27 (m, 1H).

Example 51: 5-(3-(6-(2-(4-(3,3-difluorocyclobutoxy)-6-methylpyridin-2-yl)acetamido)pyridazin-3-yl)pyrrolidin-1-yl)-N-(pyridin-2-ylmethyl)-1,3,4-thiadiazole-2-carboxamide

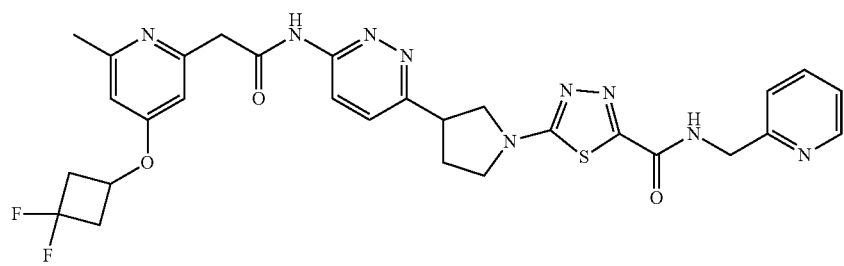 [SMILES: Cc1cc(OC2CC(F)(F)C2)cc(CC(=O)Nc2ccc(C3CCN(c4nnc(C(=O)NCc5ccccn5)s4)C3)nn2)n1]

Steps 1-9

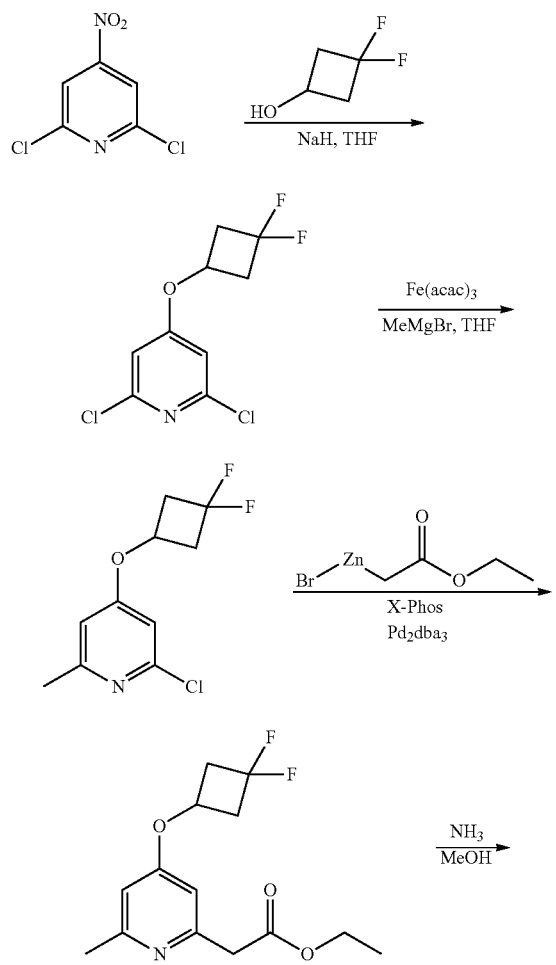

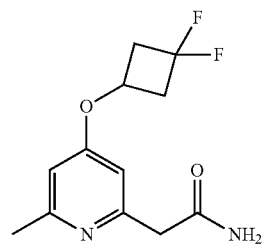

Step 1: 2,6-dichloro-4-(3,3-difluorocyclobutoxy)pyridine

To a suspension of NaH (8.88 g, 60% in mineral oil, 222 mmol) in THF (800 ml) at 0° C. was added 3,3-difluorocyclobutanol (20 g, 19 mmol) dropwise over a period of 10 min. After the completion of addition, 2,6-dichloro-4-nitropyridine (35.7 g, 185 mmol) was added portion wise and the resulting mixture was stirred at 0° C. for 1 hr. Sat. aq. NH₄Cl (200 ml) and water (800 ml) were added, and the layers were separated. The aqueous phase was extracted with EtOAc (3×500 ml), and the combined organic layers were washed with sat. aq. NaCl, dried over MgSO₄, filtered and concentrated under reduced pressure. The residue was purified by silica gel chromatography (0-8% EtOAc in hexanes) to give the title compound as a white crystalline solid (45.0 g, 96%). MS (ES⁺) C₉H₇Cl₂F₂NO requires: 253, found: 254 [M+H]⁺.

Step 2: 2-chloro-4-(3,3-difluorocyclobutoxy)-6-methylpyridine

To a solution of 2,6-dichloro-4-(3,3-difluorocyclobutoxy)pyridine (45 g, 177 mmol), THF (800 ml), NMP (200 ml) and ferric acetylacetonate (1.87 g, 5.31 mmol) at 0° C. was added dropwise methylmagnesium bromide (3 M in ether, 77 ml, 230 mmol) and the resulting mixture was stirred at 0° C. for 0.5 hrs. The reaction was quenched with sat. aq. NH₄Cl (100 ml) at 0° C., water (900 ml) was added, and the layers were separated. The aqueous phase was extracted with EtOAc (3×500 ml), and the combined organic layers were washed with sat. aq. NaCl, dried over MgSO₄, filtered and concentrated under reduced pressure. The residue was purified by silica gel chromatography (0-20% EtOAc in hexanes) to give the title compound as a colorless liquid (36.5 g, 88%). MS (ES⁺) C₁₀H₁₀ClF₂NO requires: 233, found: 234 [M+H]⁺.

Step 3: Ethyl 2-(4-(3,3-difluorocyclobutoxy)-6-methylpyridin-2-yl)acetate

A degassed solution of 2-chloro-4-(3,3-difluorocyclobutoxy)-6-methylpyridine (33.0 g, 141 mmol), (2-ethoxy-2- oxoethyl)zinc(II) bromide (0.5 M in THF, 706 ml, 350 mmol), Pd2(dba)3 (6.47 g, 7.06 mmol) and XPhos (3.37 g, 7.06 mmol) was stirred at 50° C. for 1 hr. The reaction mixture was allowed to cool to RT and sat. aq. NH4Cl (100 ml) and water (900 ml) were added. Precipitate was removed by filtration, and the filtrate layers were separated. The aqueous phase was extracted with EtOAc (3×500 ml), and the combined organic layers were washed with sat. aq. NaCl, dried over MgSO4, filtered and concentrated under reduced pressure. The residue was purified by silica gel chromatography (0-60% EtOAc in hexanes) to give the title compound as a yellow liquid (27.8 g, 69%). MS (ES+) $C_{14}H_{17}F_2NO_3$ requires: 285, found: 286 [M+H]+.

Step 4: 2-(4-(3,3-difluorocyclobutoxy)-6-methylpyridin-2-yl)acetamide

A solution of ethyl 2-(4-(3,3-difluorocyclobutoxy)-6-methylpyridin-2-yl)acetate (27.8 g, 97.0 mmol) and NH3 in MeOH (7 M, 557 ml, 390 mmol) in a pressure bottle was stirred at 85° C. for 20 hrs. The reaction mixture was allowed to cool to RT, then concentrated under reduced pressure. The resulting solid was triturated with ether and isolated by filtration to give the title compound as an off-white solid (22.4 g, 90%). MS (ES+) $C_{12}H_{14}F_2N_2O_2$ requires: 256, found: 257 [M+H]+.

Step 5: A-(6-chloropyridazin-3-yl)-2-(4-(3,3-difluorocyclobutoxy)-6-methylpyridin-2-yl)acetamide

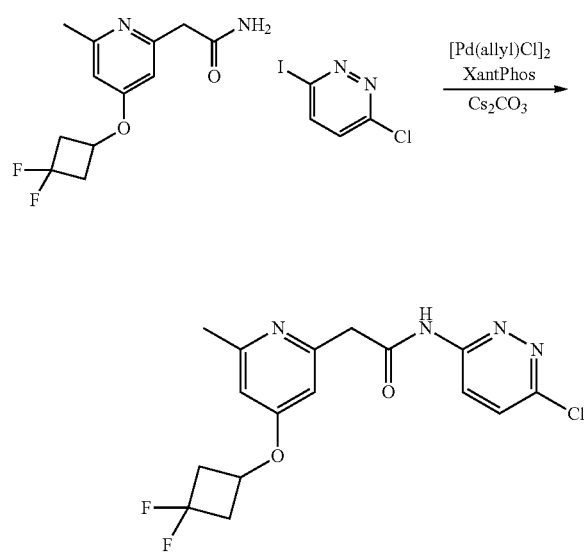

Using the procedure in Example 49, step 1 the title compound was obtained as a brown liquid (278 mg, 77%). MS (ES+) $C_{16}H_{15}ClF_2N_4O_2$ requires: 368, found: 369 [M+H]+.

Step 6: Tert-butyl 3-(6-(2-(4-(3,3-difluorocyclobutoxy)-6-methylpyridin-2-yl)acetamido) pyridazin-3-yl)-2,5-dihydro-1H-pyrrole-1-carboxylate

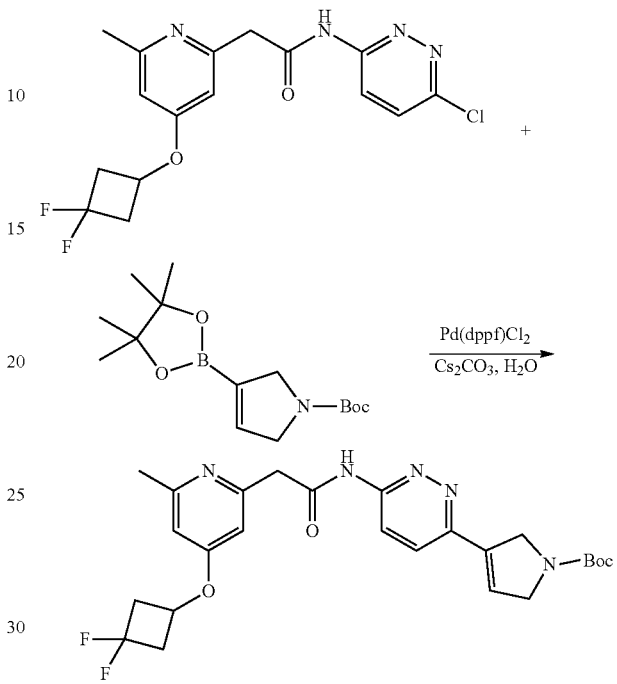

Using the procedure in Example 49, step 2 the title compound was obtained as an orange solid (243 mg, 72%). MS (ES+) $C_{25}H_{29}F_2N_5O_4$ requires: 501, found: 502 [M+H]+.

Step 7: Tert-butyl 3-(6-(2-(4-(3,3-difluorocyclobutoxy)-6-methylpyridin-2-yl)acetamido)pyridazin-3-yl)pyrrolidine-1-carboxylate

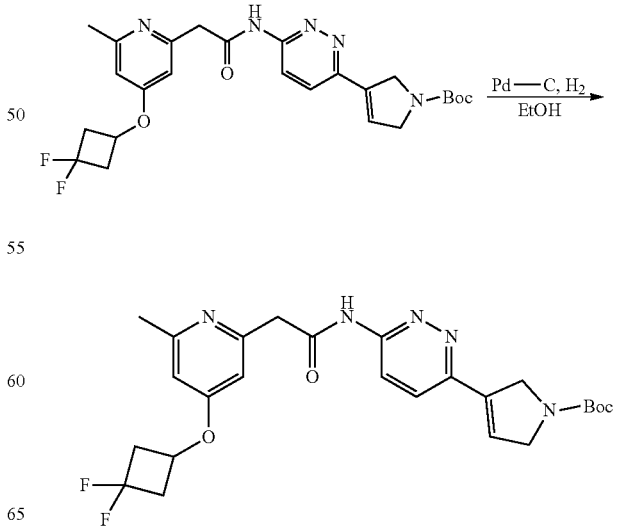

Using the procedure in Example 49, step 3 the title compound was obtained as an orange solid (210 mg, 87%). MS (ES+) $C_{25}H_{31}F_2N_5O_4$ requires: 503, found: 504 $[M+H]^+$.

Step 8: 2-(4-(3,3-difluorocyclobutoxy)-6-methylpyridin-2-yl)-N-(6-(pyrrolidin-3-yl)pyridazin-3-yl)acetamide 2,2,2-trifluoroacetate

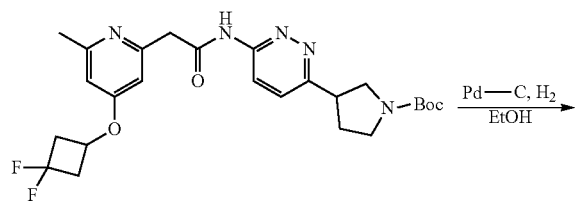

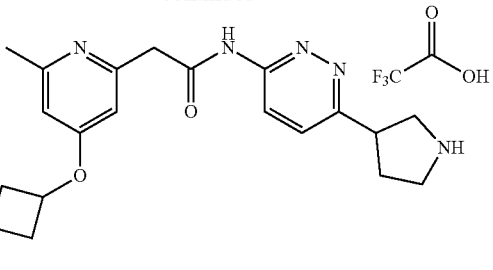

Using the procedure in Example 49, step 4 the title compound was obtained as an orange solid (206 mg, 100%). MS (ES+) $C_{20}H_{23}F_2N_5O_2$ requires: 403, found: 404 $[M+H]^+$.

Step 9: 5-(3-(6-(2-(4-(3,3-difluorocyclobutoxy)-6-methylpyridin-2-yl)acetamido)pyridazin-3-yl)pyrrolidin-1-yl)-N-(pyridin-2-ylmethyl)-1,3,4-thiadiazole-2-carboxamide

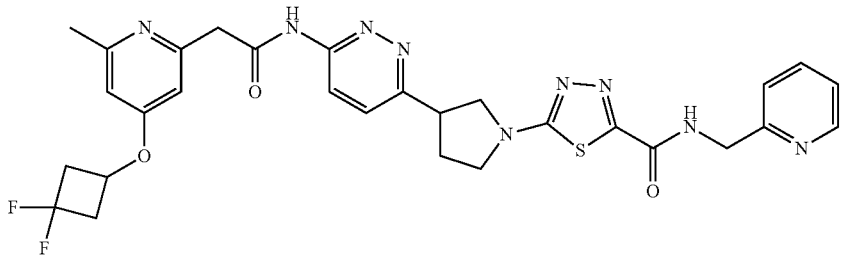 [SMILES: Cc1cc(OC2CC(F)(F)C2)cc(CC(=O)Nc2ccc(C3CCN(c4nnc(C(=O)NCc5ccccn5)s4)C3)nn2)n1]

Using the procedure in Example 46, step 2 the title compound was obtained as a yellow solid (19 mg, 32%). MS (ES+) $C_{29}H_{29}F_2N_9O_3S$ requires: 621, found: 622 $[M+H]^+$.
$^1$H NMR (600 MHz, DMSO-d$_6$) δ 11.36 (s, 1H), 9.31 (t, J=6.1 Hz, 1H), 8.51 (d, J=4.0 Hz, 1H), 8.27 (d, J=9.2 Hz, 1H), 7.81-7.66 (m, 2H), 7.32 (d, J=7.9 Hz, 1H), 7.27 (dd, J=6.4, 4.8 Hz, 1H), 6.80 (d, J=2.2 Hz, 1H), 6.72 (d, J=2.2 Hz, 1H), 4.88-4.77 (m, 1H), 4.55 (d, J=6.1 Hz, 2H), 4.00 (dd, J=9.9, 7.6 Hz, 1H), 3.94 (dt, J=15.2, 7.4 Hz, 1H), 3.89 (s, 2H), 3.80 (dd, J=9.8, 7.6 Hz, 1H), 3.73-3.68 (m, 1H), 3.67-3.61 (m, 1H), 3.28-3.19 (m, 2H), 2.77-2.65 (m, 2H), 2.56-2.51 (m, 1H), 2.40 (s, 3H), 2.35-2.26 (m, 1H).

Example 52: 5-(3-(6-(2-(4-(3,3-difluorocyclobutoxy)-6-methylpyridin-2-yl)acetamido)pyridazin-3-yl)pyrrolidin-1-yl)-N-((4-(trifluoromethyl)pyridin-2-yl)methyl)-1,3,4-thiadiazole-2-carboxamide

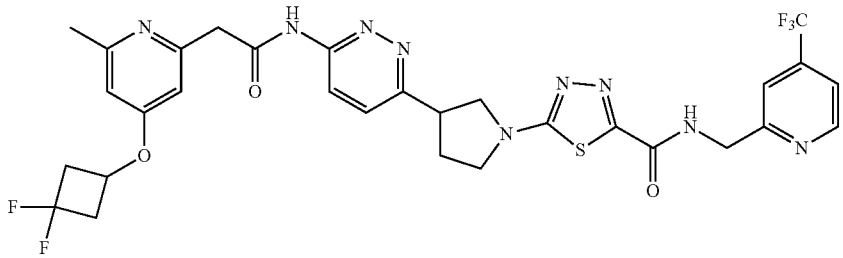 [SMILES: Cc1cc(OC2CC(F)(F)C2)cc(CC(=O)Nc2ccc(C3CCN(c4nnc(C(=O)NCc5cc(C(F)(F)F)ccn5)s4)C3)nn2)n1]

Using the procedure in Example 46, step 2 the title compound was obtained as a pale yellow solid (20 mg, 30%). MS (ES+) $C_{30}H_{28}F_5N_9C_3S$ requires: 689, found: 690 [M+H]$^+$. $^1$H NMR (600 MHz, DMSO-d$_6$) δ 11.36 (s, 1H), 9.43 (t, J=6.1 Hz, 1H), 8.81 (d, J=5.0 Hz, 1H), 8.27 (d, J=9.2 Hz, 1H), 7.74 (d, J=9.2 Hz, 1H), 7.71-7.63 (m, 2H), 6.80 (d, J=2.3 Hz, 1H), 6.72 (d, J=2.2 Hz, 1H), 4.88-4.78 (m, 1H), 4.66 (d, J=6.1 Hz, 2H), 4.00 (dd, J=9.9, 7.6 Hz, 1H), 3.97-3.91 (m, 1H), 3.89 (s, 2H), 3.80 (dd, J=9.9, 7.6 Hz, 1H), 3.74-3.68 (m, 1H), 3.68-3.61 (m, 1H), 3.29-3.19 (m, 2H), 2.76-2.65 (m, 2H), 2.56-2.51 (m, 1H), 2.40 (s, 3H), 2.36-2.27 (m, 1H).

Example 53: 5-(3-(6-(2-(4-(3,3-difluorocyclobutoxy)-6-methylpyridin-2-yl)acetamido)pyridazin-3-yl)pyrrolidin-1-yl)-N-((6-methylpyridin-2-yl)methyl)-1,3,4-thiadiazole-2-carboxamide

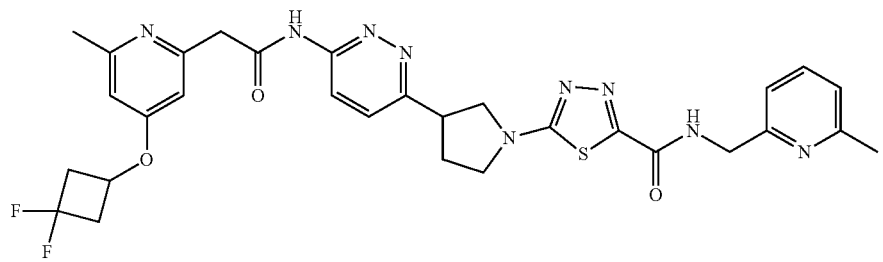 [SMILES: Cc1cccc(CNC(=O)c2nnc(N3CCC(c4ccc(NC(=O)Cc5cc(OC6CC(F)(F)C6)cc(C)n5)nn4)C3)s2)n1]

Using the procedure in Example 46, step 2 the title compound was obtained as a pale yellow solid (23 mg, 32%). MS (ES+) $C_{30}H_{31}F_2N_9O_3S$ requires: 635, found: 636 [M+H]$^+$. $^1$H NMR (600 MHz, DMSO-d$_6$) δ 11.43 (s, 1H), 9.30 (t, J=6.1 Hz, 1H), 8.25 (d, J=9.2 Hz, 1H), 7.75 (d, J=9.2 Hz, 1H), 7.66 (t, J=7.7 Hz, 1H), 7.14 (d, J=7.6 Hz, 1H), 7.11 (d, J=7.7 Hz, 1H), 7.03-6.81 (m, 2H), 4.90 (s, 1H), 4.50 (d, J=6.1 Hz, 2H), 4.04-3.90 (m, 4H), 3.80 (dd, J=9.8, 7.6 Hz, 1H), 3.73-3.61 (m, 2H), 3.30-3.21 (m, 2H), 2.82-2.70 (m, 2H), 2.56-2.51 (m, 1H), 2.48-2.44 (m, 6H), 2.35-2.27 (m, 1H).

TABLE 1

Synthesized Compounds

| Ex. | Structure | IUPAC Name |
|---|---|---|
| 1 | 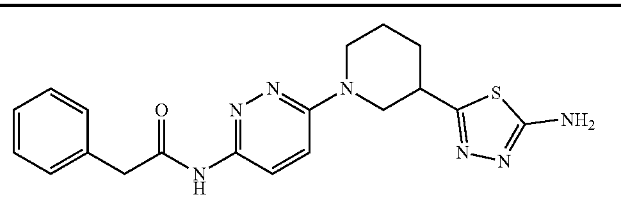 | N-(6-(3-(5-Amino-1,3,4-thiadiazol-2-yl)piperidin-1-yl)pyridazin-3-yl)-2-phenylacetamide |
| 2 | 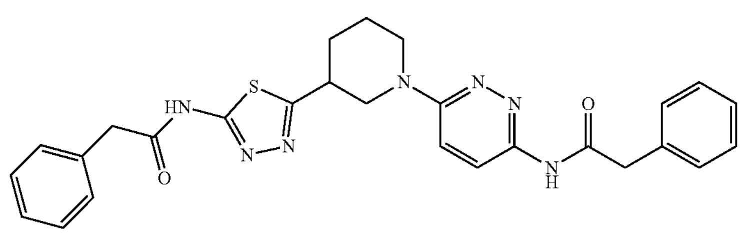 [SMILES: O=C(Cc1ccccc1)Nc1ccc(N2CCCC(c3nnc(NC(=O)Cc4ccccc4)s3)C2)nn1] | 2-Phenyl-N-(6-(3-(5-(2-phenylacetamido)-1,3,4-thiadiazol-2-yl)piperidin-1-yl)pyridazin-3-yl)acetamide |
| 3 | 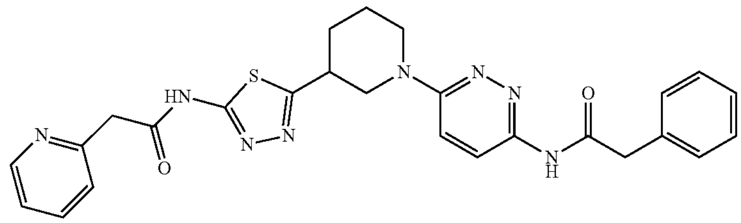 [SMILES: O=C(Cc1ccccc1)Nc1ccc(N2CCCC(c3nnc(NC(=O)Cc4ccccn4)s3)C2)nn1] | 2-Phenyl-N-(6-(3-(5-(2-(pyridin-2-yl)acetamido)-1,3,4-thiadiazol-2-yl)piperidin-1-yl)pyridazin-3-yl)acetamide |

TABLE 1-continued

Synthesized Compounds

| Ex. | Structure | IUPAC Name |
|---|---|---|
| 4 | 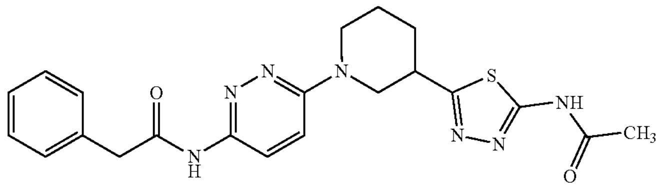 [SMILES: CC(=O)Nc1nnc(C2CCCN(c3ccc(NC(=O)Cc4ccccc4)nn3)C2)s1] | N-(6-(3-(5-Acetamido-1,3,4-thiadiazol-2-yl)piperidin-1-yl)pyridazin-3-yl)-2-phenylacetamide |
| 5 | 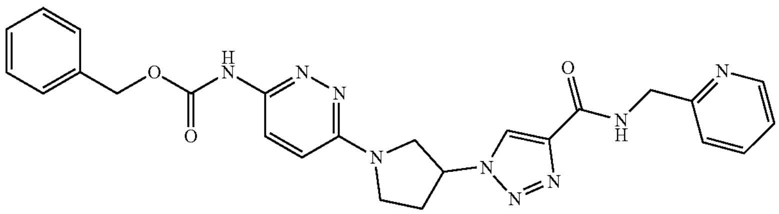 [SMILES: O=C(Nc1ccc(N2CCC(n3cc(C(=O)NCc4ccccn4)nn3)C2)nn1)OCc1ccccc1] | Benzyl (6-(3-(4-((pyridin-2-ylmethyl)carbamoyl)-1H-1,2,3-triazol-1-yl)pyrrolidin-1-yl)pyridazin-3-yl)carbamate |
| 6 | 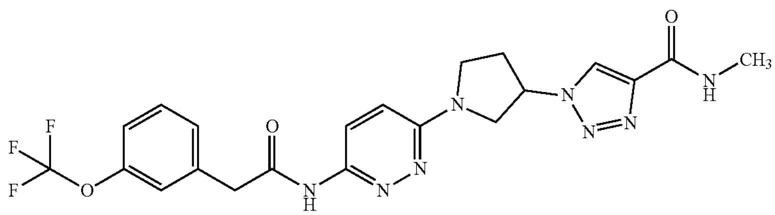 [SMILES: CNC(=O)c1cn(C2CCN(c3ccc(NC(=O)Cc4cccc(OC(F)(F)F)c4)nn3)C2)nn1] | N-Methyl-1-(1-(6-(2-(3-(trifluoromethoxy)phenyl)acetamido)pyridazin-3-yl)pyrrolidin-3-yl)-1H-1,2,3-triazole-4-carboxamide |
| 7 | 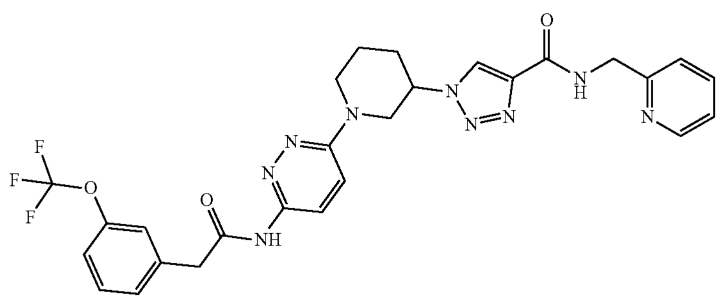 [SMILES: O=C(Cc1cccc(OC(F)(F)F)c1)Nc1ccc(N2CCCC(n3cc(C(=O)NCc4ccccn4)nn3)C2)nn1] | N-(Pyridin-2-ylmethyl)-1-(1-(6-(2-(3-(trifluoromethoxy)phenyl)acetamido)pyridazin-3-yl)piperidin-3-yl)-1H-1,2,3-triazole-4-carboxamide |
| 8 | 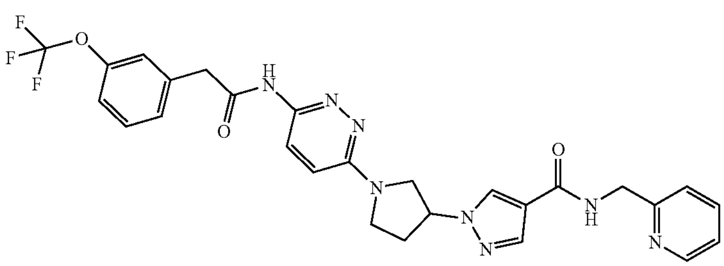 [SMILES: O=C(Cc1cccc(OC(F)(F)F)c1)Nc1ccc(N2CCC(n3cc(C(=O)NCc4ccccn4)cn3)C2)nn1] | N-(pyridin-2-ylmethyl)-1-(1-(6-(2-(3-(trifluoromethoxy)phenyl)acetamido)pyridazin-3-yl)pyrrolidin-3-yl)-1H-1,2,3-triazole-4-carboxamide |
| 9 | 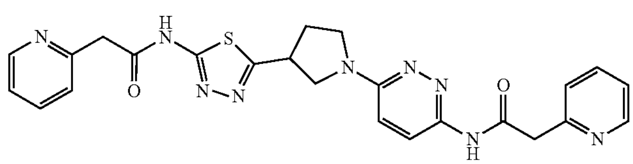 [SMILES: O=C(Cc1ccccn1)Nc1ccc(N2CCC(c3nnc(NC(=O)Cc4ccccn4)s3)C2)nn1] | 2-(Pyridin-2-yl)-N-(6-(3-(5-(2-(pyridin-2-yl)acetamido)-1,3,4-thiadiazol-2-yl)pyrrolidin-1-yl)pyridazin-3-yl)acetamide |
| 10 | 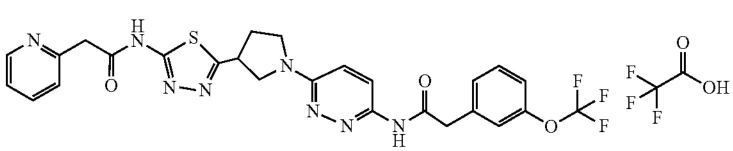 | 2-(pyridin-2-yl)-N-(5-(1-(6-(2-(3-(trifluoromethoxy)phenyl)acetamido)pyridazin-3-yl)pyrrolidin-3-yl)-1,3,4-thiadiazol-2-yl)acetamide 2,2,2-trifluoroacetate |

TABLE 1-continued

Synthesized Compounds

| Ex. | Structure | IUPAC Name |
|---|---|---|
| 11 | 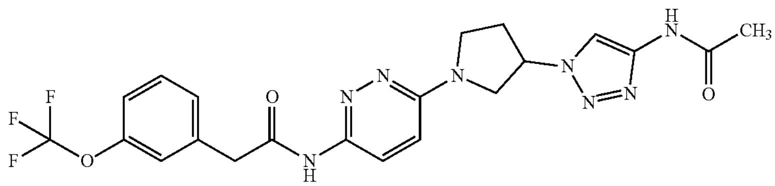 [SMILES: CC(=O)Nc1cn(C2CCN(c3ccc(NC(=O)Cc4cccc(OC(F)(F)F)c4)nn3)C2)nn1] | N-(6-(3-(4-acetamido-1H-1,2,3-triazol-1-yl)pyrrolidin-1-yl)pyridazin-3-yl)-2-(3-(trifluoromethoxy)phenyl)acetamide |
| 12 | 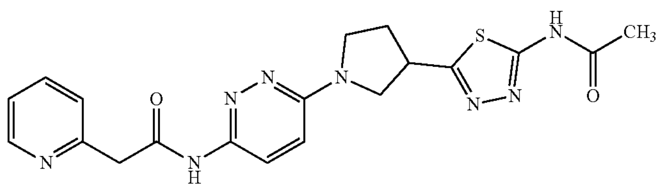 [SMILES: CC(=O)Nc1nnc(C2CCN(c3ccc(NC(=O)Cc4ccccn4)nn3)C2)s1] | N-(6-(3-(5-Acetamido-1,3,4-thiadiazol-2-yl)pyrrolidin-1-yl)pyridazin-3-yl)-2-(pyridin-2-yl)acetamide |
| 13 | 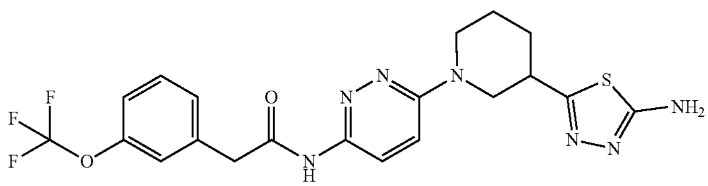 [SMILES: Nc1nnc(C2CCCN(c3ccc(NC(=O)Cc4cccc(OC(F)(F)F)c4)nn3)C2)s1] | N-(6-(3-(5-Amino-1,3,4-thiadiazol-2-yl)piperidin-1-yl)pyridazin-3-yl)-2-(3-(trifluoromethoxy)phenyl)acetamide |
| 14 | 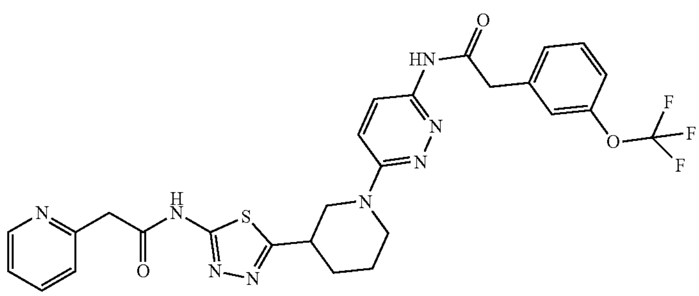 [SMILES: O=C(Cc1cccc(OC(F)(F)F)c1)Nc1ccc(N2CCCC(c3nnc(NC(=O)Cc4ccccn4)s3)C2)nn1] | 2-(pyridin-2-yl)-N-(5-(1-(6-(2-(3-(trifluoromethoxy)phenyl)acetamido)pyridazin-3-yl)piperidin-3-yl)-1,3,4-thiadiazol-2-yl)acetamide |
| 15 | 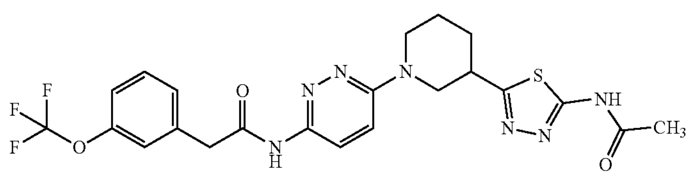 [SMILES: CC(=O)Nc1nnc(C2CCCN(c3ccc(NC(=O)Cc4cccc(OC(F)(F)F)c4)nn3)C2)s1] | N-(6-(3-(5-Acetamido-1,3,4-thiadiazol-2-yl)piperidin-1-yl)pyridazin-3-yl)-2-(3-(trifluoromethoxy)phenyl)acetamide |
| 16 | 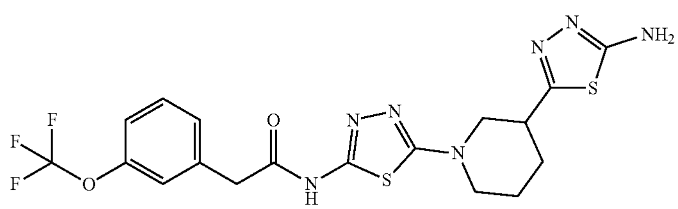 [SMILES: Nc1nnc(C2CCCN(c3nnc(NC(=O)Cc4cccc(OC(F)(F)F)c4)s3)C2)s1] | N-(5-(3-(5-Amino-1,3,4-thiadiazol-2-yl)piperidin-1-yl)-1,3,4-thiadiazol-2-yl)-2-(3-(trifluoromethoxy)phenyl)acetamide |
| 17 | 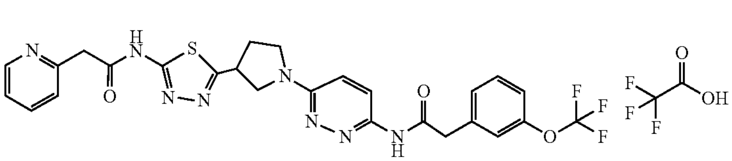 | 2-(pyridin-2-yl)-N-(5-(1-(6-(2-(3-(trifluoromethoxy)phenyl)acetamido)pyridazin-3-yl)pyrrolidin-3-yl)-1,3,4-thiadiazol-2-yl)acetamide 2,2,2-trifluoroacetate |
| 18 | 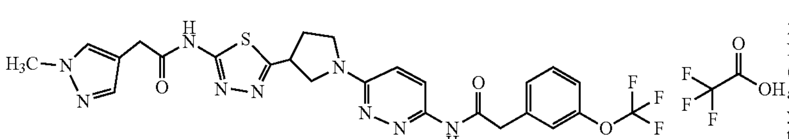 | 2-(1-methyl-1H-pyrazol-4-yl)-N-(5-(1-(6-(2-(3-(trifluoromethoxy)phenyl)acetamido)pyridazin-3-yl)pyrrolidin-3-yl)-1,3,4-thiadiazol-2-yl)acetamide 2,2,2-trifluoroacetate |

US 11,713,313 B2

TABLE 1-continued

Synthesized Compounds

| Ex. | Structure | IUPAC Name |
|---|---|---|
| 19 | 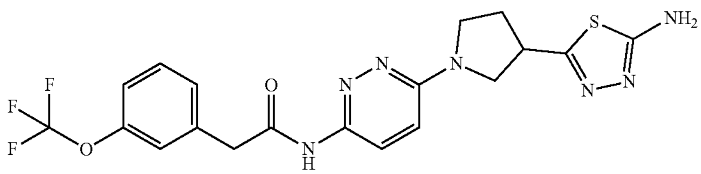 [SMILES: Nc1nnc(C2CCN(c3ccc(NC(=O)Cc4cccc(OC(F)(F)F)c4)nn3)C2)s1] | N-(6-(3-(5-amino-1,3,4-thiadiazol-2-yl)pyrrolidin-1-yl)pyridazin-3-yl)-2-(3-(trifluoromethoxy)phenyl)acetamide |
| 20 | 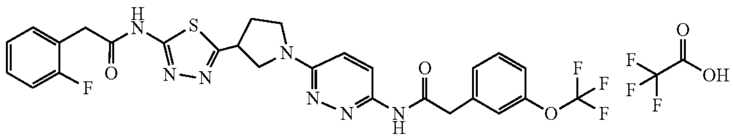 | 2-(2-fluorophenyl)-N-(5-(1-(6-(2-(3-(trifluoromethoxy)phenyl)acetamido)pyridazin-3-yl)pyrrolidin-3-yl)-1,3,4-thiadiazol-2-yl)acetamide 2,2,2-trifluoroacetate |
| 21 | 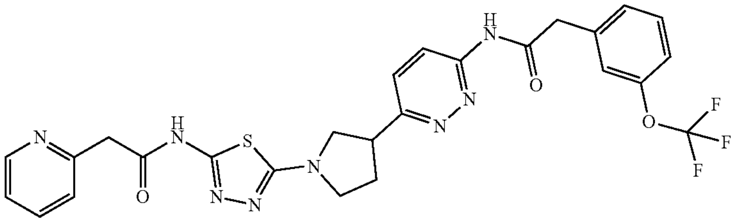 [SMILES: O=C(Cc1cccc(OC(F)(F)F)c1)Nc1ccc(C2CCN(c3nnc(NC(=O)Cc4ccccn4)s3)C2)nn1] | 2-(pyridin-2-yl)-N-(5-(3-(6-(2-(3-(trifluoromethoxy)phenyl)acetamido)pyridazin-3-yl)pyrrolidin-1-yl)-1,3,4-thiadiazol-2-yl)acetamide |
| 22 | 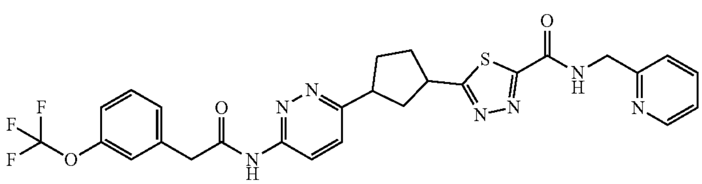 [SMILES: O=C(Cc1cccc(OC(F)(F)F)c1)Nc1ccc(C2CCC(c3nnc(C(=O)NCc4ccccn4)s3)C2)nn1] | N-(pyridin-2-ylmethyl)-5-(3-(6-(2-(3-(trifluoromethoxy)phenyl)acetamido)pyridazin-3-yl)pyrrolidin-1-yl)-1,3,4-thiadiazole-2-carboxamide |
| 23 | 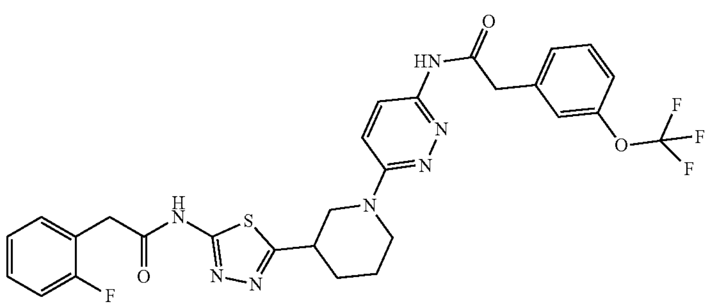 [SMILES: O=C(Cc1cccc(OC(F)(F)F)c1)Nc1ccc(N2CCCC(c3nnc(NC(=O)Cc4ccccc4F)s3)C2)nn1] | 2-(2-Fluorophenyl)-N-(5-(1-(6-(2-(3-(trifluoromethoxy)phenyl)acetamido)pyridazin-3-yl)piperidin-3-yl)-1,3,4-thiadiazol-2-yl)acetamide |
| 24 | 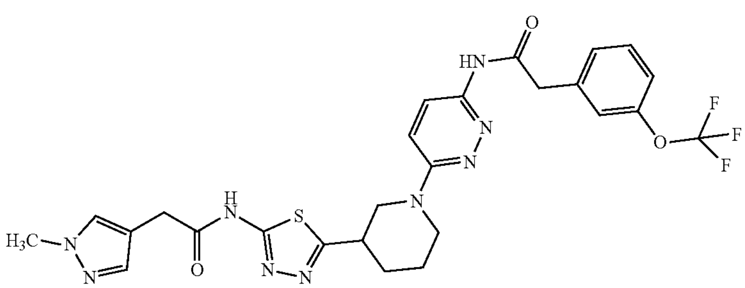 [SMILES: Cn1cc(CC(=O)Nc2nnc(C3CCCN(c4ccc(NC(=O)Cc5cccc(OC(F)(F)F)c5)nn4)C3)s2)cn1] | 2-(1-Methyl-1H-pyrazol-4-yl)-N-(5-(1-(6-(2-(3-(trifluoromethoxy)phenyl)acetamido)pyridazin-3-yl)piperidin-3-yl)-1,3,4-thiadiazol-2-yl)acetamide |
| 25 | 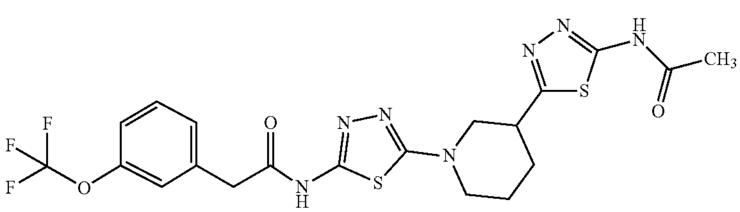 [SMILES: CC(=O)Nc1nnc(C2CCCN(c3nnc(NC(=O)Cc4cccc(OC(F)(F)F)c4)s3)C2)s1] | N-(5-(3-(5-acetamido-1,3,4-thiadiazol-2-yl)piperidin-1-yl)-1,3,4-thiadiazol-2-yl)-2-(3-(trifluoromethoxy)phenyl)acetamide |

TABLE 1-continued

Synthesized Compounds

| Ex. | Structure | IUPAC Name |
|---|---|---|
| 26 | 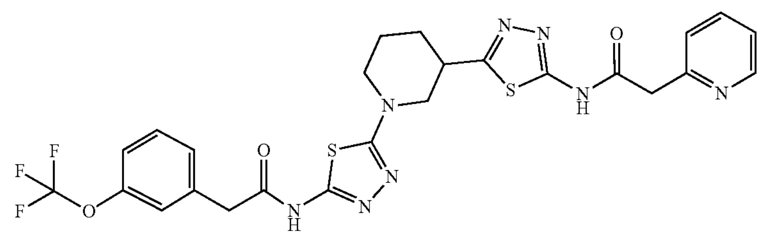 [SMILES: O=C(Cc1ccccn1)Nc1nnc(C2CCCN(c3nnc(NC(=O)Cc4cccc(OC(F)(F)F)c4)s3)C2)s1] | 2-(Pyridin-2-yl)-N-(5-(1-(5-(2-(3-(trifluoromethoxy)phenyl)acetamido)-1,3,4-thiadiazol-2-yl)piperidin-3-yl)-1,3,4-thiadiazol-2-yl)acetamide |
| 27 | 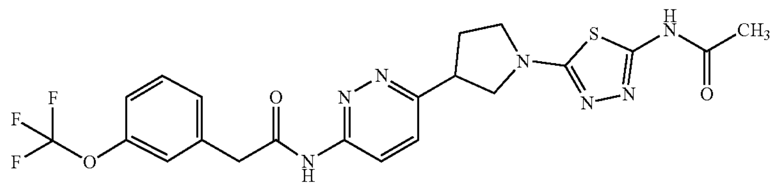 [SMILES: CC(=O)Nc1nnc(N2CCC(c3ccc(NC(=O)Cc4cccc(OC(F)(F)F)c4)nn3)C2)s1] | N-(6-(1-(5-acetamido-1,3,4-thiadiazol-2-yl)pyrrolidin-3-yl)pyridazin-3-yl)-2-(3-(trifluoromethoxy)phenyl)acetamide |
| 28 | [This example is intentionally left blank] | |
| 29 | 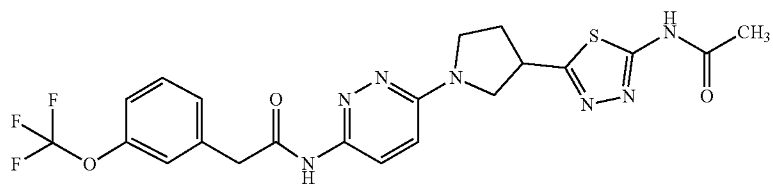 [SMILES: CC(=O)Nc1nnc(C2CCN(c3ccc(NC(=O)Cc4cccc(OC(F)(F)F)c4)nn3)C2)s1] | N-(6-(3-(5-acetamido-1,3,4-thiadiazol-2-yl)pyrrolidin-1-yl)pyridazin-3-yl)-2-(3-(trifluoromethoxy)phenyl)acetamide |
| 30 | 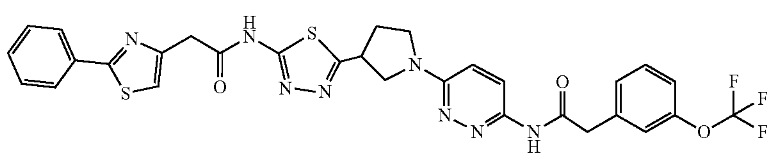 [SMILES: O=C(Cc1cccc(OC(F)(F)F)c1)Nc1ccc(N2CCC(c3nnc(NC(=O)Cc4csc(-c5ccccc5)n4)s3)C2)nn1] | 2-(2-phenylthiazol-4-yl)-N-(5-(1-(6-(2-(3-(trifluoromethoxy)phenyl)acetamido)pyridazin-3-yl)pyrrolidin-3-yl)-1,3,4-thiadiazol-2-yl)acetamide |
| 31 | 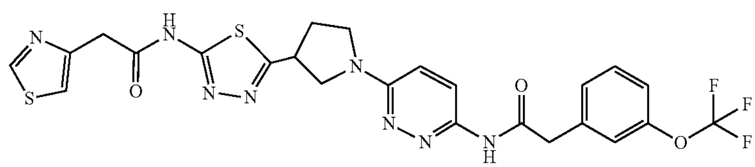 [SMILES: O=C(Cc1cccc(OC(F)(F)F)c1)Nc1ccc(N2CCC(c3nnc(NC(=O)Cc4cscn4)s3)C2)nn1] | 2-(thiazol-4-yl)-N-(5-(1-(6-(2-(3-(trifluoromethoxy)phenyl)acetamido)pyridazin-3-yl)pyrrolidin-3-yl)-1,3,4-thiadiazol-2-yl)acetamide |
| 32 | 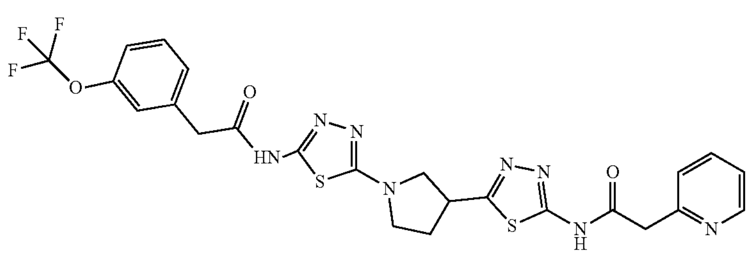 [SMILES: O=C(Cc1ccccn1)Nc1nnc(C2CCN(c3nnc(NC(=O)Cc4cccc(OC(F)(F)F)c4)s3)C2)s1] | 2-(Pyridin-2-yl)-N-(5-(1-(5-(2-(3-(trifluoromethoxy)phenyl)acetamido)-1,3,4-thiadiazol-2-yl)pyrrolidin-3-yl)-1,3,4-thiadiazol-2-yl)acetamide |
| 33 | 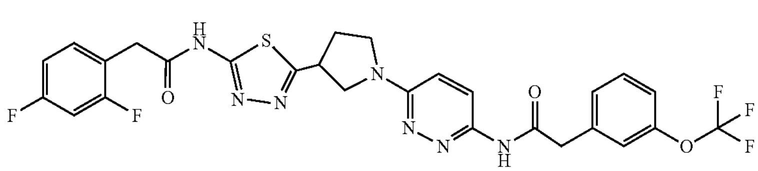 [SMILES: O=C(Cc1cccc(OC(F)(F)F)c1)Nc1ccc(N2CCC(c3nnc(NC(=O)Cc4ccc(F)cc4F)s3)C2)nn1] | 2-(2,4-difluorophenyl)-N-(5-(1-(6-(2-(3-(trifluoromethoxy)phenyl)acetamido)pyridazin-3-yl)pyrrolidin-3-yl)-1,3,4-thiadiazol-2-yl)acetamide |

TABLE 1-continued

Synthesized Compounds

| Ex. | Structure | IUPAC Name |
|---|---|---|
| 34 | 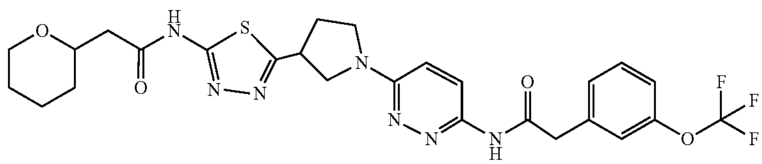 [SMILES: O=C(Cc1cccc(OC(F)(F)F)c1)Nc1ccc(N2CCC(c3nnc(NC(=O)CC4CCCCO4)s3)C2)nn1] | 2-(tetrahydro-2H-pyran-2-yl)-N-(5-(1-(6-(2-(3-(trifluoromethoxy)phenyl)acetamido)pyridazin-3-yl)pyrrolidin-3-yl)-1,3,4-thiadiazol-2-yl)acetamide |
| 35 | [This example is intentionally left blank] | |
| 36 | 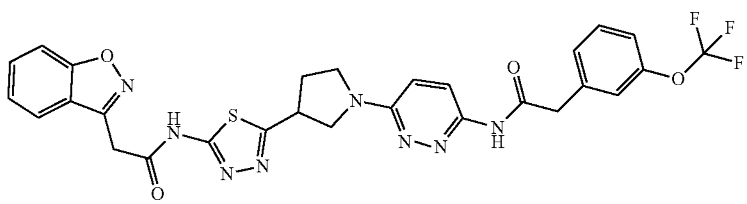 [SMILES: O=C(Cc1cccc(OC(F)(F)F)c1)Nc1ccc(N2CCC(c3nnc(NC(=O)Cc4noc5ccccc45)s3)C2)nn1] | 2-(benzo[d]isoxazol-3-yl)-N-(5-(1-(6-(2-(3-(trifluoromethoxy)phenyl)acetamido)pyridazin-3-yl)pyrrolidin-3-yl)-1,3,4-thiadiazol-2-yl)acetamide |
| 37 | 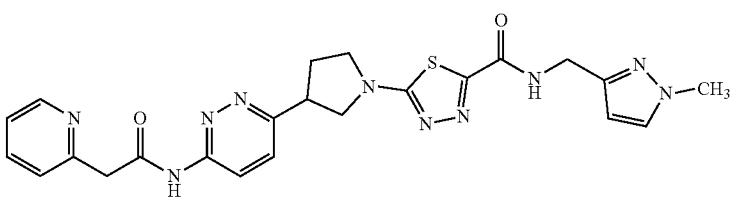 [SMILES: Cn1ccc(CNC(=O)c2nnc(N3CCC(c4ccc(NC(=O)Cc5ccccn5)nn4)C3)s2)n1] | N-((1-methyl-1H-pyrazol-3-yl)methyl)-5-(3-(6-(2-(pyridin-2-yl)acetamido)pyridazin-3-yl)pyrrolidin-1-yl)-1,3,4-thiadiazole-2-carboxamide |
| 38 | 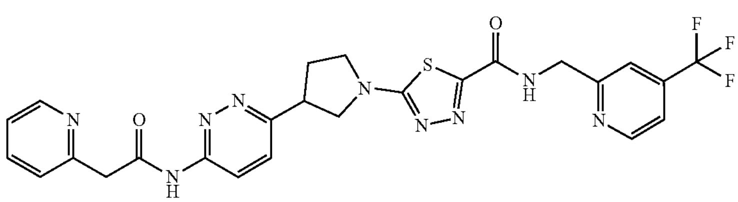 [SMILES: O=C(Cc1ccccn1)Nc1ccc(C2CCN(c3nnc(C(=O)NCc4cc(C(F)(F)F)ccn4)s3)C2)nn1] | 5-(3-(6-(2-(pyridin-2-yl)acetamido)pyridazin-3-yl)pyrrolidin-1-yl)-N-((4-(trifluoromethyl)pyridin-2-yl)methyl)-1,3,4-thiadiazole-2-carboxamide |
| 39 | 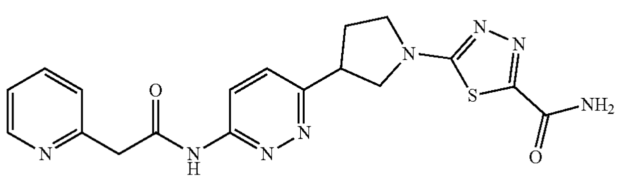 [SMILES: NC(=O)c1nnc(N2CCC(c3ccc(NC(=O)Cc4ccccn4)nn3)C2)s1] | 5-(3-(6-(2-(pyridin-2-yl)acetamido)pyridazin-3-yl)pyrrolidin-1-yl)-1,3,4-thiadiazole-2-carboxamide |
| 40 | 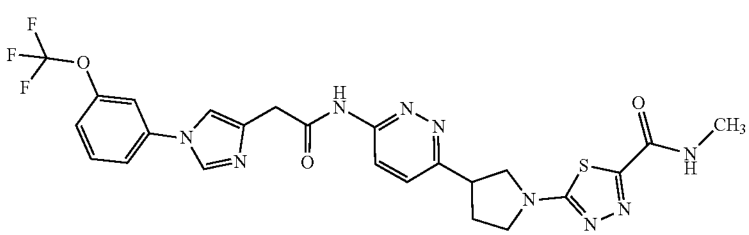 [SMILES: CNC(=O)c1nnc(N2CCC(c3ccc(NC(=O)Cc4cn(-c5cccc(OC(F)(F)F)c5)cn4)nn3)C2)s1] | N-methyl-5-(3-(6-(2-(1-(3-(trifluoromethoxy)phenyl)-1H-imidazol-4-yl)acetamido)pyridazin-3-yl)pyrrolidin-1-yl)-1,3,4-thiadiazole-2-carboxamide |
| 41 | 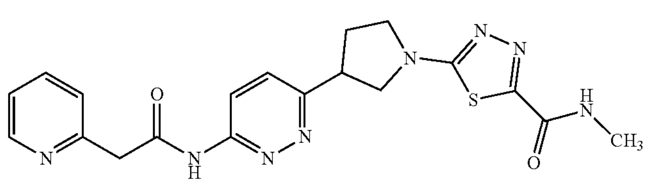 [SMILES: CNC(=O)c1nnc(N2CCC(c3ccc(NC(=O)Cc4ccccn4)nn3)C2)s1] | N-methyl-5-(3-(6-(2-(pyridin-2-yl)acetamido)pyridazin-3-yl)pyrrolidin-1-yl)-1,3,4-thiadiazole-2-carboxamide |

TABLE 1-continued

Synthesized Compounds

| Ex. | Structure | IUPAC Name |
|---|---|---|
| 42 | 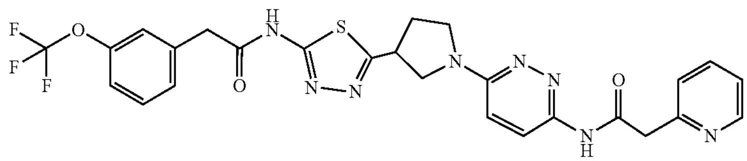 [SMILES: O=C(Cc1ccccn1)Nc1ccc(N2CCC(c3nnc(NC(=O)Cc4cccc(OC(F)(F)F)c4)s3)C2)nn1] | 2-(pyridin-2-yl)-N-(6-(3-(5-(2-(3-(trifluoromethoxy)phenyl)acetamido)-1,3,4-thiadiazol-2-yl)pyrrolidin-1-yl)pyridazin-3-yl)acetamide |
| 43 | 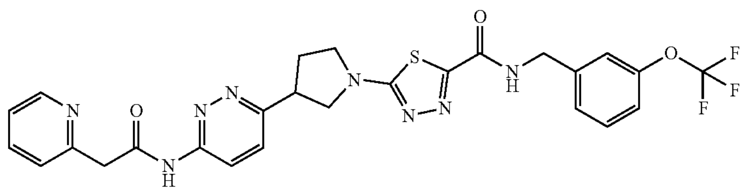 [SMILES: O=C(Cc1ccccn1)Nc1ccc(C2CCN(c3nnc(C(=O)NCc4cccc(OC(F)(F)F)c4)s3)C2)nn1] | 5-(3-(6-(2-(pyridin-2-yl)acetamido)pyridazin-3-yl)pyrrolidin-1-yl)-N-(3-(trifluoromethoxy)benzyl)-1,3,4-thiadiazole-2-carboxamide |
| 44 | 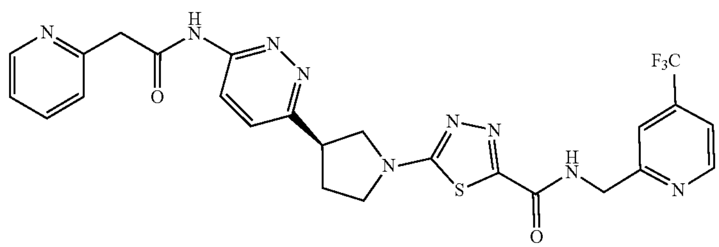 [SMILES: O=C(Cc1ccccn1)Nc1ccc([C@@H]2CCN(c3nnc(C(=O)NCc4cc(C(F)(F)F)ccn4)s3)C2)nn1] | (R)-5-(3-(6-(2-(pyridin-2-yl)acetamido)pyridazin-3-yl)pyrrolidin-1-yl)-N-((4-(trifluoromethyl)pyridin-2-yl)methyl)-1,3,4-thiadiazole-2-carboxamide |
| 45 | 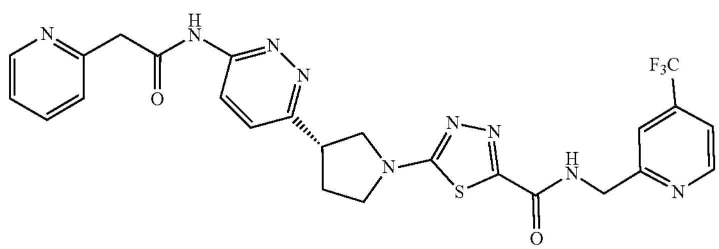 [SMILES: O=C(Cc1ccccn1)Nc1ccc([C@H]2CCN(c3nnc(C(=O)NCc4cc(C(F)(F)F)ccn4)s3)C2)nn1] | (S)-5-(3-(6-(2-(pyridin-2-yl)acetamido)pyridazin-3-yl)pyrrolidin-1-yl)-N-(pyridin-2-ylmethyl)-1,3,4-thiadiazole-2-carboxamide |
| 46 | 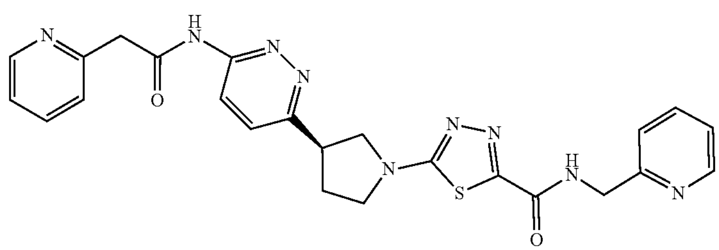 [SMILES: O=C(Cc1ccccn1)Nc1ccc([C@@H]2CCN(c3nnc(C(=O)NCc4ccccn4)s3)C2)nn1] | (R)-5-(3-(6-(2-(pyridin-2-yl)acetamido)pyridazin-3-yl)pyrrolidin-1-yl)-N-(pyridin-2-ylmethyl)-1,3,4-thiadiazole-2-carboxamide |
| 47 | 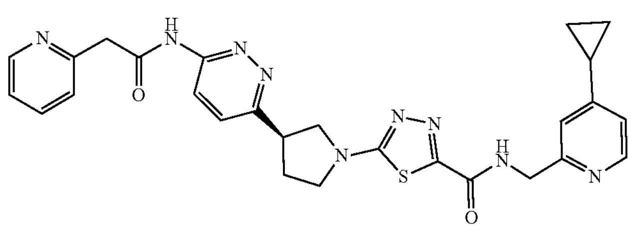 [SMILES: O=C(Cc1ccccn1)Nc1ccc([C@@H]2CCN(c3nnc(C(=O)NCc4cc(C5CC5)ccn4)s3)C2)nn1] | (R)-N-((4-cyclopropylpyridin-2-yl)methyl)-5-(3-(6-(2-(pyridin-2-yl)acetamido)pyridazin-3-yl)pyrrolidin-1-yl)-1,3,4-thiadiazole-2-carboxamide |
| 48 | 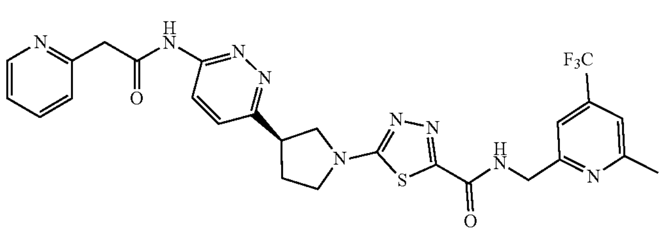 [SMILES: Cc1cc(C(F)(F)F)cc(CNC(=O)c2nnc(N3CC[C@@H](c4ccc(NC(=O)Cc5ccccn5)nn4)C3)s2)n1] | (R)-N-((6-methyl-4-(trifluoromethyl)pyridin-2-yl)methyl)-5-(3-(6-(2-(pyridin-2-yl)acetamido)pyridazin-3-yl)pyrrolidin-1-yl)-1,3,4-thiadiazole-2-carboxamide |

TABLE 1-continued

Synthesized Compounds

| Ex. | Structure | IUPAC Name |
|---|---|---|
| 49 | 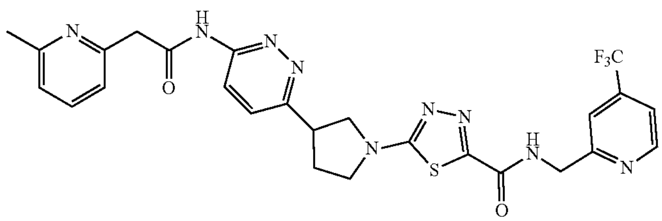 [SMILES: Cc1cccc(CC(=O)Nc2ccc(C3CCN(c4nnc(C(=O)NCc5cc(C(F)(F)F)ccn5)s4)C3)nn2)n1] | 5-(3-(6-(2-(6-methylpyridin-2-yl)acetamido)pyridazin-3-yl)pyrrolidin-1-yl)-N-((4-(trifluoromethyl)pyridin-2-yl)methyl)-1,3,4-thiadiazole-2-carboxamide |
| 50 | 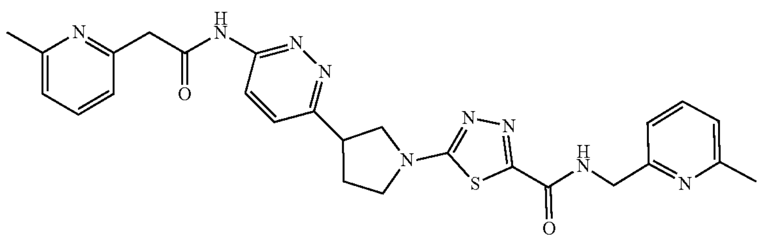 | 5-(3-(6-(2-(6-methylpyridin-2-yl)acetamido)pyridazin-3-yl)pyrrolidin-1-yl)-N-((6-methylpyridin-2-yl)methyl)-1,3,4-thiadiazole-2-carboxamid |
| 51 | 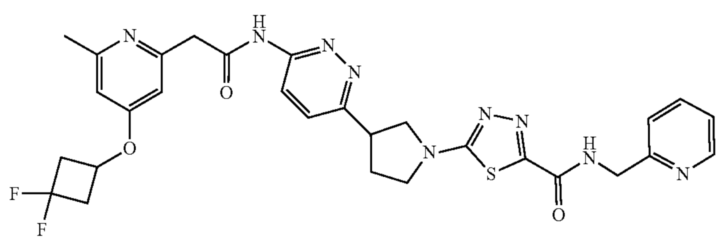 [SMILES: Cc1cc(OC2CC(F)(F)C2)cc(CC(=O)Nc2ccc(C3CCN(c4nnc(C(=O)NCc5ccccn5)s4)C3)nn2)n1] | 5-(3-(6-(2-(4-(3,3-difluorocyclobutoxy)-6-methylpyridin-2-yl)acetamido)pyridazin-3-yl)pyrrolidin-1-yl)-N-(pyridin-2-ylmethyl)-1,3,4-thiadiazole-2-carboxamide |
| 52 | 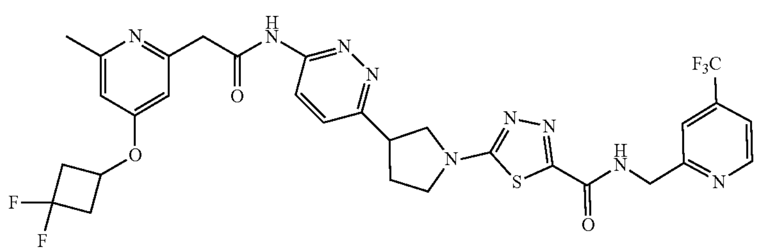 [SMILES: Cc1cc(OC2CC(F)(F)C2)cc(CC(=O)Nc2ccc(C3CCN(c4nnc(C(=O)NCc5cc(C(F)(F)F)ccn5)s4)C3)nn2)n1] | 5-(3-(6-(2-(4-(3,3-difluorocyclobutoxy)-6-methylpyridin-2-yl)acetamido)pyridazin-3-yl)pyrrolidin-1-yl)-N-((4-(trifluoromethyl)pyridin-2-yl)methyl)-1,3,4-thiadiazole-2-carboxamide |
| 53 | 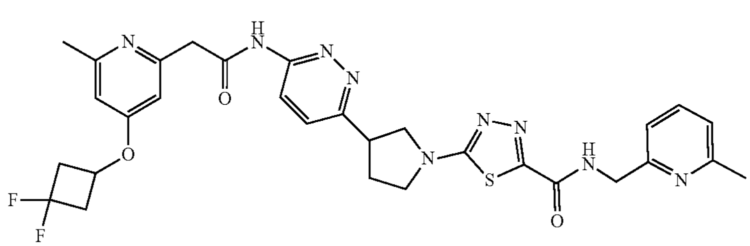 [SMILES: Cc1cccc(CNC(=O)c2nnc(N3CCC(c4ccc(NC(=O)Cc5cc(OC6CC(F)(F)C6)cc(C)n5)nn4)C3)s2)n1] | 5-(3-(6-(2-(4-(3,3-difluorocyclobutoxy)-6-methylpyridin-2-yl)acetamido)pyridazin-3-yl)pyrrolidin-1-yl)-N-((6-methylpyridin-2-yl)methyl)-1,3,4-thiadiazole-2-carboxamide |

Table 2 below reports the observed molecular ion (ES⁺) (Mass Spec) [M+H]⁺ of each Example, as well as the method by which each compound may be made by reference to each Example whose synthesis is substantially similar that one skilled in the art could produce the compound using, if necessary, variations know in the art.

TABLE 2

Observed Molecular Weight and Synthesis for Examples

| Ex. | MW | [M + H]⁺ | Method |
|---|---|---|---|
| 1 | 395.481 | 396 | 13 |
| 2 | 513.614 | 514 | 14 |
| 3 | 514.602 | 515 | 14 |
| 4 | 437.518 | 438 | 14 |
| 5 | 499.5245 | 500 | 5 |
| 6 | 490.4384 | 491 | 8 |
| 7 | 581.549 | 582 | 8 |
| 8 | 567.5225 | 568 | 8 |
| 9 | 501.564 | 502 | 9 |
| 10 | 584.573 | 585 | 10 |
| 11 | 490.4384 | 491 | 11 |
| 12 | 424 | 425 | 14 |
| 13 | 479.479 | 480 | 13 |
| 14 | 598.599 | 599 | 14 |
| 15 | 521.515 | 522 | 14 |
| 16 | 485.506 | 486 | 16 |
| 17 | 584.573 | 585 | 17 |
| 18 | 587.577 | 588 | 20 |
| 19 | 465.452 | 466 | 19 |
| 20 | 601.575 | 602 | 20 |
| 21 | 584.573 | 585 | 21 |
| 22 | 584.573 | 585 | 22 |
| 23 | 615.602 | 616 | 14 |
| 24 | 601.603 | 602 | 14 |
| 25 | 527.543 | 528 | 26 |
| 26 | 604.627 | 605 | 26 |
| 27 | 507.489 | 508 | 27 |
| 28 | [This example intentionally left blank] | | |
| 29 | 507.489 | 508 | 27 |
| 30 | 666.697 | 667 | 21 |
| 31 | 590.601 | 591 | 21 |
| 32 | 590.601 | 591 | 26 |
| 33 | 619.566 | 620 | 20 |
| 34 | 591.605 | 592 | 20 |
| 35 | [This example intentionally left blank] | | |
| 36 | 624.594 | 625 | 20 |
| 37 | 504.567 | 505 | 37 |
| 38 | 569.561 | 570 | 37 |
| 39 | 410.453 | 411 | 37 |
| 40 | 573.55 | 574 | 37 |
| 41 | 424.48 | 425 | 37 |
| 42 | 584 | 585 | 17 |
| 43 | 584.573 | 585 | 22 |
| 44 | 569 | 570 | 44 |
| 45 | 569 | 570 | 44 |
| 46 | 501 | 502 | 44 |
| 47 | 541 | 542 | 44 |
| 48 | 583 | 584 | 44 |
| 49 | 583 | 584 | 49 |
| 50 | 529 | 530 | 49 |
| 51 | 621 | 622 | 51 |
| 52 | 689 | 690 | 51 |
| 53 | 635 | 636 | 51 |

Additional Compounds

The following compounds, which may not yet have been made or tested, may be made as disclosed herein, and are expected to have activity similar to those made and tested.

Example 54: (R)—N-((4-(3,3-difluorocyclobutoxy)-6-methylpyridin-2-yl)methyl)-5-(3-(6-(2-(pyridin-2-yl)acetamido)pyridazin-3-yl)pyrrolidin-1-yl)-1,3,4-thiadiazole-2-carboxamide

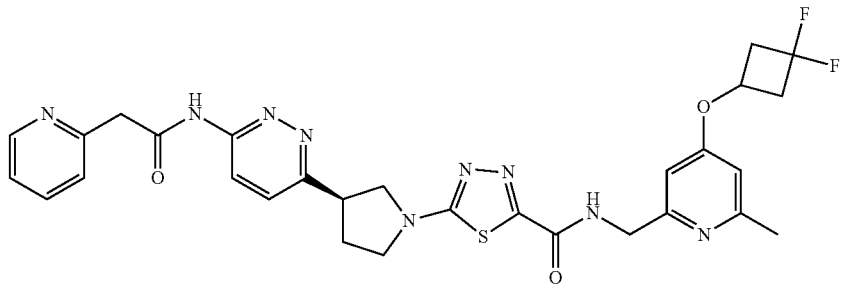 [SMILES: Cc1cc(OC2CC(F)(F)C2)cc(CNC(=O)c2nnc(N3CC[C@@H](c4ccc(NC(=O)Cc5ccccn5)nn4)C3)s2)n1]

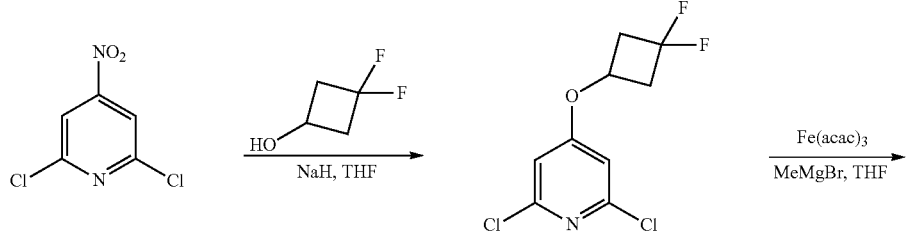

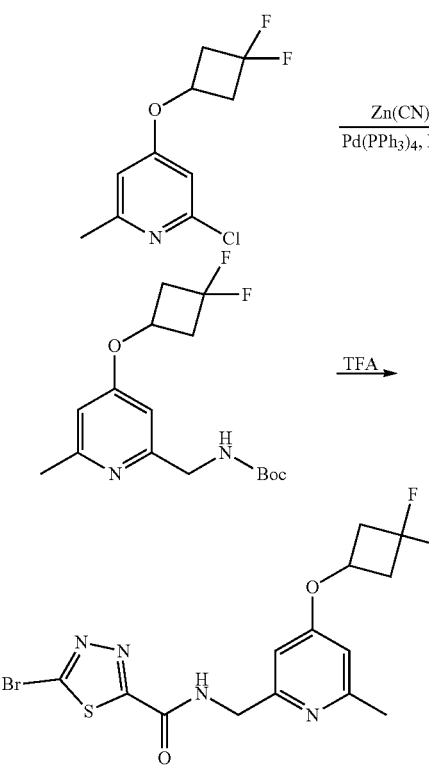
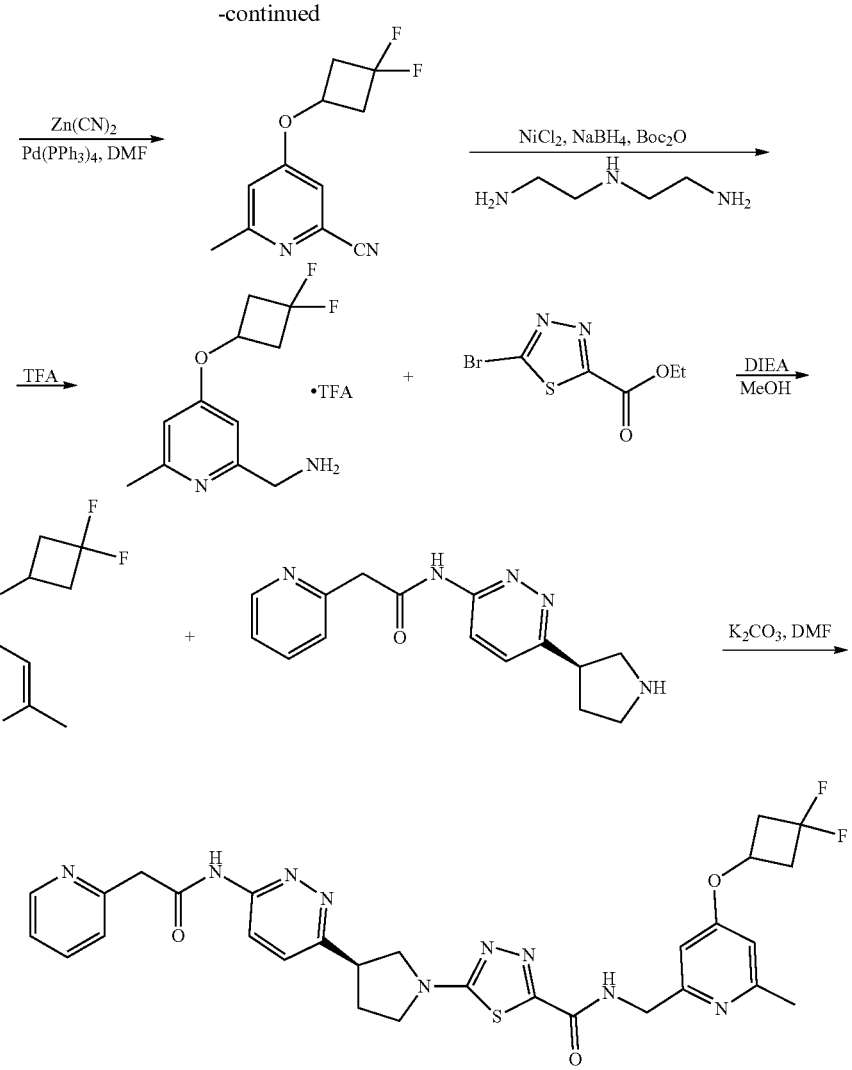

Biological Activity Assays

The following are assays that may be used to evaluate the biological efficacy of compounds of Formula (I).

GLS1 Enzymatic Activity Assay

The inhibition of purified recombinant human GAC by varying concentrations of inhibitors is assessed via a dual-coupled enzymatic assay. The glutamate produced by the glutaminase reaction is used by glutamate oxidase to produce α-ketoglutarate, ammonia, and hydrogen peroxide, with this hydrogen peroxide subsequently being used by horseradish peroxidase to produce resorufin in the presence of Amplex UltraRed. The assay buffer consisted of 50 mM HEPES (pH 7.4), 0.25 mM EDTA and 0.1 mM Triton X-100. GAC was incubated with potassium phosphate (10 minutes at room temperature) prior to incubation with inhibitor (10 minutes at room temperature). The final reaction conditions were as follows: 2 nM GAC, 50 mM potassium phosphate, 100 mU/ml glutamate oxidase (Sigma), 1 mM glutamine (Sigma), 100 mU/ml horseradish peroxidase (Sigma), 75 μM Amplex UltraRed (Life Technologies), and 1% (v/v) DMSO. The production of resorufin was monitored on a Perkin Elmer Envision plate reader (excitation 530 nm, emission 590 nm) either in a kinetics or endpoint mode (at 20 minutes). $IC_{50}$ values were calculated using a four-parameter logistic curve fit.

Proliferation Assay

A549 cells were routinely maintained in RPMI 1640 media (Gibco catalog number 11875-093) supplemented with 10% dialyzed fetal bovine serum using a humidified incubator (37° C., 5% $CO_2$ and ambient $O_2$). In preparation for the viability assay, cells were inoculated into 384-well black CulturPlates (Perkin Elmer) at a density of 1000 cells/well in a volume of 40 μl. Following a 24-hour incubation at 37° C. 5% $CO_2$ and ambient $O_2$, cells were treated with compound (10 μl) in a final DMSO concentration of 0.5% (v/v). The microplates were then incubated for 72 hours (37° C. 5% $CO_2$ and ambient $O_2$). Cell Titer Fluor (Promega) was subsequently added (10 μl of 6× reagent) and mixed for 15 minutes at room temperature. The plates were then incubated for 30 minutes (37° C. 5% $CO_2$ and ambient $O_2$) and fluorescence was subsequently read on the Perkin Elmer Envision plate reader. $EC_{50}$ values were calculated using a four-parameter logistic curve fit.

Table 3 below reports the $IC_{50}$ against GLS1 and the $EC_{50}$ against A549 cell proliferation, both in nanomolar, and both wherein A=<100 nM, B=100-500 nM, and C=500-5000 nM.

TABLE 3

GLS1 IC$_{50}$ Data and A549 EC$_{50}$ Data

| Ex. | GLS1 | A549 |
|---|---|---|
| 1 | B | C |
| 2 | A | B |
| 3 | A | B |
| 4 | B | C |
| 5 | C | C |
| 6 | B | C |
| 7 | B | C |
| 8 | B | C |
| 9 | A | C |
| 10 | A | B |
| 11 | B | C |
| 12 | B | ND |
| 13 | B | C |
| 14 | A | A |
| 15 | A | B |
| 16 | B | C |
| 17 | A | A |
| 18 | A | B |
| 19 | B | C |
| 20 | A | B |
| 21 | A | B |
| 22 | A | A |
| 23 | A | B |
| 24 | A | C |
| 25 | B | C |
| 26 | A | B |
| 27 | A | B |
| 28 |  | n/a |
| 29 | A | B |
| 30 | A | A |
| 31 | A | B |
| 32 | B | C |
| 33 | A | B |
| 34 | A | A |
| 35 |  | n/a |
| 36 | A | B |
| 37 | A | B |
| 38 | A | A |
| 39 | B | C |
| 40 | A | A |
| 41 | B | B |
| 42 | A | B |
| 43 | A | A |
| 44 | A | A |
| 45 | B | A |
| 46 | A | A |
| 47 | A | A |
| 48 | A | A |
| 49 | A | A |
| 50 | A | A |
| 51 | A | A |
| 52 | A | A |
| 53 | A | A |

OTHER EMBODIMENTS

The detailed description set-forth above is provided to aid those skilled in the art in practicing the present disclosure. However, the disclosure described and claimed herein is not to be limited in scope by the specific embodiments herein disclosed because these embodiments are intended as illustration of several aspects of the disclosure. Any equivalent embodiments are intended to be within the scope of this disclosure. Indeed, various modifications of the disclosure in addition to those shown and described herein will become apparent to those skilled in the art from the foregoing description, which do not depart from the spirit or scope of the present inventive discovery. Such modifications are also intended to fall within the scope of the appended claims.

What is claimed is:

1. A method of inhibiting GLS1 activity in a biological sample comprising contacting the biological sample with a compound of a compound of structural Formula I

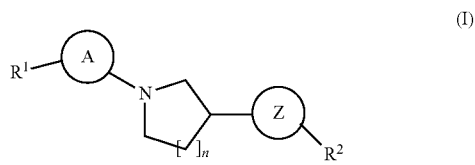

or a salt thereof, wherein:

n is 1;

$R^1$ is chosen from $NR^3C(O)R^3$, $NR^3C(O)OR^3$, $NR^3C(O)N(R^3)_2$, $C(O)N(R^3)_2$, and $N(R^3)_2$;

each $R^3$ is independently chosen from alkyl, aryl, arylalkyl, cycloalkyl, cycloalkylalkyl, H, haloalkyl, heteroaryl, heteroarylalkyl, heterocycloalkyl, heterocycloalkylalkyl, wherein each $R^3$ may be optionally substituted with one to three $R^x$ groups, wherein two $R^3$ groups together with the atoms to which they are attached optionally form an heteroaryl or heterocycloalkyl ring, which may be optionally substituted with one to three $R^x$ groups;

$R^2$ is chosen from $NR^4C(O)R^4$, $NR^4C(O)OR^4$, $NR^4C(O)N(R^4)_2$, $C(O)N(R^4)_2$ and $N(R^4)_2$;

each $R^4$ is independently chosen from alkyl, aryl, arylalkyl, cycloalkyl, cycloalkylalkyl, H, haloalkyl, heteroaryl, heteroarylalkyl, heterocycloalkyl, and heterocycloalkylalkyl, wherein each $R^4$ may be optionally substituted with one to three $R^x$ groups, wherein two $R^4$ groups together with the atoms to which they are attached optionally form an heteroaryl or heterocycloalkyl ring, which may be optionally substituted with one to three $R^x$ groups;

each $R^x$ group is independently chosen from alkoxy, alkoxyalkyl, alkoxyaryl, alkoxyarylalkyl, alkoxycycloalkyl, alkoxycycloalkylalkyl, alkoxyhaloalkyl, alkoxyheteroaryl, alkoxyheteroarylalkyl, alkoxyheterocycloalkyl, alkoxyheterocycloalkylalkyl, alkyl, alkylaryl, alkylarylalkyl, alkylcycloalkyl, alkylcycloalkylalkyl, alkylheteroaryl, alkylheteroarylalkyl, alkylheterocycloalkyl, alkylheterocycloalkylalkyl, aryl, arylalkyl, arylalkyloxy, arylhaloalkyl, aryloxy, cyano, cycloalkyl, cycloalkylalkyl, cycloalkylalkyloxy, cycloalkylhaloalkyl, cycloalkyloxy, halo, haloalkoxy, haloalkoxyalkyl, haloalkoxyaryl, haloalkoxyarylalkyl, haloalkoxycycloalkyl, haloalkoxycycloalkylalkyl, haloalkoxyheteroaryl, haloalkoxyheteroarylalkyl, haloalkoxyheterocycloalkyl, haloalkoxyheterocycloalkylalkyl, haloalkyl, haloalkylaryl, haloalkylarylalkyl, haloalkylcycloalkyl, haloalkylcycloalkylalkyl, haloalkylheteroaryl, haloalkylheteroarylalkyl, haloalkylheterocycloalkyl, haloalkylheterocycloalkylalkyl, haloaryl, haloarylalkyl, haloarylalkyloxy, haloaryloxy, halocycloalkyl, halocycloalkylalkyl, halocycloalkylalkyloxy, halocycloalkyloxy, haloheteroaryl, haloheteroarylalkyl, haloheteroarylalkyloxy, haloheteroaryloxy, haloheterocycloalkyl, haloheterocycloalkylalkyl, haloheterocycloalkylalkyloxy, haloheterocycloalkyloxy, heteroaryl, heteroarylalkyl, heteroarylalkyloxy, heteroarylhaloalkyl, heteroaryloxy, heterocycloalkyl, heterocycloalkylalkyl, heterocycloalkylalkyloxy, heterocycloalkylhaloalkyl, heterocycloalkyloxy, hydroxyl, oxo, $N(R^5)_2$, $NR^5C(O)R^5$, $NR^5C(O)OR^5$, $NR^5C(O)N(R^5)_2$, $C(O)N(R^5)_2$, and $C(O)R^5$;

each $R^5$ is independently chosen from alkyl, aryl, arylalkyl, cycloalkyl, cycloalkylalkyl, H, haloalkyl, heteroaryl, heteroarylalkyl, heterocycloalkyl, and heterocycloalkylalkyl, which may be optionally substituted with one to three $R^z$ groups; and $R^z$ is chosen from alkyl, aryl, arylalkyl, cyano, cycloalkyl, cycloalkylalkyl, H, halo, haloalkyl, heteroaryl, heteroarylalkyl, heterocycloalkyl, and heterocycloalkylalkyl;

A is a monocyclic heteroaryl, which may be optionally substituted with one to three $R^z$ groups; and Z is a monocyclic heteroaryl, which may be optionally substituted with one to three $R^z$ groups.

2. A method of treating a GLS1-mediated disorder in a subject in need thereof, comprising the step of administering to the subject a compound of structural Formula I

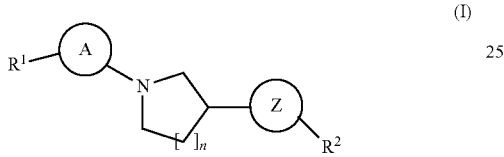

or a salt thereof, wherein:
n is 1;
$R^1$ is chosen from $NR^3C(O)R^3$, $NR^3C(O)OR^3$, $NR^3C(O)N(R^3)_2$, $C(O)N(R^3)_2$, and $N(R^3)_2$;
each $R^3$ is independently chosen from alkyl, aryl, arylalkyl, cycloalkyl, cycloalkylalkyl, H, haloalkyl, heteroaryl, heteroarylalkyl, heterocycloalkyl, heterocycloalkylalkyl, wherein each $R^3$ may be optionally substituted with one to three $R^x$ groups, wherein two $R^3$ groups together with the atoms to which they are attached optionally form an heteroaryl or heterocycloalkyl ring, which may be optionally substituted with one to three $R^x$ groups;
$R^2$ is chosen from $NR^4C(O)R^4$, $NR^4C(O)OR^4$, $NR^4C(O)N(R^4)_2$, $C(O)N(R^4)_2$ and $N(R^4)_2$;
each $R^4$ is independently chosen from alkyl, aryl, arylalkyl, cycloalkyl, cycloalkylalkyl, H, haloalkyl, heteroaryl, heteroarylalkyl, heterocycloalkyl, and heterocycloalkylalkyl, wherein each $R^4$ may be optionally substituted with one to three $R^x$ groups, wherein two $R^4$ groups together with the atoms to which they are attached optionally form an heteroaryl or heterocycloalkyl ring, which may be optionally substituted with one to three $R^x$ groups;
each $R^x$ group is independently chosen from alkoxy, alkoxyalkyl, alkoxyaryl, alkoxyarylalkyl, alkoxycycloalkyl, alkoxycycloalkylalkyl, alkoxyhaloalkyl, alkoxyheteroaryl, alkoxyheteroarylalkyl, alkoxyheterocycloalkyl, alkoxyheterocycloalkylalkyl, alkyl, alkylaryl, alkylarylalkyl, alkylcycloalkyl, alkylcycloalkylalkyl, alkylheteroaryl, alkylheteroarylalkyl, alkylheterocycloalkyl, alkylheterocycloalkylalkyl, aryl, arylalkyl, arylalkyloxy, arylhaloalkyl, aryloxy, cyano, cycloalkyl, cycloalkylalkyl, cycloalkylalkyloxy, cycloalkylhaloalkyl, cycloalkyloxy, halo, haloalkoxy, haloalkoxyalkyl, haloalkoxyaryl, haloalkoxyarylalkyl, haloalkoxycycloalkyl, haloalkoxycycloalkylalkyl, haloalkoxyheteroaryl, haloalkoxyheteroarylalkyl, haloalkoxyheterocycloalkyl, haloalkoxyheterocycloalkylalkyl, haloalkyl, haloalkylaryl, haloalkylarylalkyl, haloalkylcycloalkyl, haloalkylcycloalkylalkyl, haloalkylheteroaryl, haloalkylheteroarylalkyl, haloalkylheterocycloalkyl, haloalkylheterocycloalkylalkyl, haloaryl, haloarylalkyl, haloarylalkyloxy, haloaryloxy, halocycloalkyl, halocycloalkylalkyl, halocycloalkylalkyloxy, halocycloalkyloxy, haloheteroaryl, haloheteroarylalkyl, haloheteroarylalkyloxy, haloheteroaryloxy, haloheterocycloalkyl, haloheterocycloalkylalkyl, haloheterocycloalkylalkyloxy, haloheterocycloalkyloxy, heteroaryl, heteroarylalkyl, heteroarylalkyloxy, heteroarylhaloalkyl, heteroaryloxy, heterocycloalkyl, heterocycloalkylalkyl, heterocycloalkylalkyloxy, heterocycloalkylhaloalkyl, heterocycloalkyloxy, hydroxyl, oxo, $N(R^5)_2$, $NR^5C(O)R^5$, $NR^5C(O)OR^5$, $NR^5C(O)N(R^5)_2$, $C(O)N(R^5)_2$, and $C(O)R^5$;

each $R^5$ is independently chosen from alkyl, aryl, arylalkyl, cycloalkyl, cycloalkylalkyl, H, haloalkyl, heteroaryl, heteroarylalkyl, heterocycloalkyl, and heterocycloalkylalkyl, which may be optionally substituted with one to three $R^z$ groups; and $R^z$ is chosen from alkyl, aryl, arylalkyl, cyano, cycloalkyl, cycloalkylalkyl, H, halo, haloalkyl, heteroaryl, heteroarylalkyl, heterocycloalkyl, and heterocycloalkylalkyl;

A is a monocyclic heteroaryl, which may be optionally substituted with one to three $R^z$ groups; and Z is a monocyclic heteroaryl, which may be optionally substituted with one to three $R^z$ groups.

3. The method according to claim 2, wherein the subject is a human.

4. The method according to claim 2, wherein the GLS1-mediated disorder is chosen from cancer, immunological disorders, and neurological disorders.

5. The method according to claim 2, wherein the GLS1-mediated disorder is cancer.

6. The method according to claim 5, wherein the cancer is chosen from Acute Lymphoblastic Leukemia (ALL), Acute Myeloid Leukemia (AML), Adrenocortical Carcinoma, AIDS-Related Cancers (Kaposi Sarcoma and Lymphoma), Anal Cancer, Appendix Cancer, Atypical Teratoid/Rhabdoid Tumor, Basal Cell Carcinoma, Bile Duct Cancer (including Extrahepatic), Bladder Cancer, Bone Cancer (including Osteosarcoma and Malignant Fibrous Histiocytoma), Brain Tumor (such as Astrocytomas, Brain and Spinal Cord Tumors, Brain Stem Glioma, Central Nervous System Atypical Teratoid/Rhabdoid Tumor, Central Nervous System Embryonal Tumors, Craniopharyngioma, Ependymoblastoma, Ependymoma, Medulloblastoma, Medulloepithelioma, Pineal Parenchymal Tumors of Intermediate Differentiation, Supratentorial Primitive Neuroectodermal Tumors and Pineoblastoma), Breast Cancer, Bronchial Tumors, Burkitt Lymphoma, Basal Cell Carcinoma, Bile Duct Cancer (including Extrahepatic), Bladder Cancer, Bone Cancer (including Osteosarcoma and Malignant Fibrous Histiocytoma), Carcinoid Tumor, Carcinoma of Unknown Primary, Central Nervous System (such as Atypical Teratoid/Rhabdoid Tumor, Embryonal Tumors and Lymphoma), Cervical Cancer, Childhood Cancers, Chordoma, Chronic Lymphocytic Leukemia (CLL), Chronic Myelogenous Leukemia (CML), Chronic Myeloproliferative Disorders, Colon Cancer, Colorectal Cancer, Craniopharyngioma, Cutaneous T-Cell Lymphoma (Mycosis Fungoides and Sézary Syndrome), Duct, Bile (Extrahepatic), Ductal Carcinoma In Situ (DCIS), Embryonal Tumors (Central Nervous System), Endometrial Cancer, Ependymoblastoma, Ependymoma, Esophageal Cancer, Esthesioneuroblastoma, Ewing Sarcoma Family of Tumors, Extracranial Germ Cell Tumor, Extragonadal Germ Cell Tumor, Extrahepatic Bile Duct Cancer, Eye Cancer (like Intraocular Melanoma, Retinoblastoma), Fibrous Histiocytoma of Bone (including Malignant and Osteosarcoma) Gallbladder Cancer, Gastric (Stomach) Cancer, Gastrointestinal Carcinoid Tumor, Gastrointestinal Stromal Tumors (GIST), Germ Cell Tumor (Extracranial, Extragonadal, Ovarian), Gestational Trophoblastic Tumor, Glioma, Hairy Cell Leukemia, Head and Neck Cancer, Heart Cancer, Hepatocellular (Liver) Cancer, Histiocytosis, Langerhans Cell, Hodgkin Lymphoma, Hypopharyngeal Cancer, Intraocular Melanoma, Islet Cell Tumors (Endocrine, Pancreas), Kaposi Sarcoma, Kidney (including Renal Cell), Langerhans Cell Histiocytosis, Laryngeal Cancer, Leukemia (including Acute Lymphoblastic (ALL), Acute Myeloid (AML), Chronic Lymphocytic (CLL), Chronic Myelogenous (CML), Hairy Cell), Lip and Oral Cavity Cancer, Liver Cancer (Primary), Lobular Carcinoma In Situ (LCIS), Lung Cancer (Non-Small Cell and Small Cell), Lymphoma (AIDS-Related, Burkitt, Cutaneous T-Cell (Mycosis Fungoides and Sézary Syndrome), Hodgkin, Non-Hodgkin, Primary Central Nervous System (CNS), Macroglobulinemia, Waldenström, Male Breast Cancer, Malignant Fibrous Histiocytoma of Bone and Osteosarcoma, Medulloblastoma, Medulloepithelioma, Melanoma (including Intraocular (Eye)), Merkel Cell Carcinoma, Mesothelioma (Malignant), Metastatic Squamous Neck Cancer with Occult Primary, Midline Tract Carcinoma Involving NUT Gene, Mouth Cancer, Multiple Endocrine Neoplasia Syndromes, Multiple Myeloma/Plasma Cell Neoplasm, Mycosis Fungoides, Myelodysplastic Syndromes, Myelodysplastic/Myeloproliferative Neoplasms, Myeloma and Multiple Myeloma, Myeloproliferative Disorders (Chronic), Nasal Cavity and Paranasal Sinus Cancer, Nasopharyngeal Cancer, Neuroblastoma, Non-Hodgkin Lymphoma, Non-Small Cell Lung Cancer, Oral Cancer, Oral Cavity Cancer, Lip and, Oropharyngeal Cancer, Osteosarcoma and Malignant Fibrous Histiocytoma of Bone, Ovarian Cancer (such as Epithelial, Germ Cell Tumor, and Low Malignant Potential Tumor), Pancreatic Cancer (including Islet Cell Tumors), Papillomatosis, Paraganglioma, Paranasal Sinus and Nasal Cavity Cancer, Parathyroid Cancer, Penile Cancer, Pharyngeal Cancer, Pheochromocytoma, Pineal Parenchymal Tumors of Intermediate Differentiation, Pineoblastoma and Supratentorial Primitive Neuroectodermal Tumors, Pituitary Tumor, Plasma Cell Neoplasm/Multiple Myeloma, Pleuropulmonary Blastoma, Pregnancy and Breast Cancer, Primary Central Nervous System (CNS) Lymphoma, Prostate Cancer, Rectal Cancer, Renal Cell (Kidney) Cancer, Renal Pelvis and Ureter, Transitional Cell Cancer, Retinoblastoma, Rhabdomyosarcoma, Salivary Gland Cancer, Sarcoma (like Ewing Sarcoma Family of Tumors, Kaposi, Soft Tissue, Uterine), Sézary Syndrome, Skin Cancer (such as Melanoma, Merkel Cell Carcinoma, Nonmelanoma), Small Cell Lung Cancer, Small Intestine Cancer, Soft Tissue Sarcoma, Squamous Cell Carcinoma, Squamous Neck Cancer with Occult Primary, Metastatic, Stomach (Gastric) Cancer, Supratentorial Primitive Neuroectodermal Tumors, T-Cell Lymphoma (Cutaneous, Mycosis Fungoides and Sézary Syndrome), Testicular Cancer, Throat Cancer, Thymoma and Thymic Carcinoma, Thyroid Cancer, Transitional Cell Cancer of the Renal Pelvis and Ureter, Trophoblastic Tumor (Gestational), Unknown Primary, Unusual Cancers of Childhood, Ureter and Renal Pelvis, Transitional Cell Cancer, Urethral Cancer, Uterine Cancer, Endometrial, Uterine Sarcoma, Waldenström Macroglobulinemia and Wilms Tumor, or a variant thereof.

7. The method as recited in claim 2, further comprising the sequential or co-administration of another therapeutic agent.

8. The method according to claim 7, wherein the therapeutic agent is chosen from a taxane, inhibitor of bcr-abl, inhibitor of EGFR, DNA damaging agent, and antimetabolite.

9. The method according to claim 7, wherein the therapeutic agent is chosen from aminoglutethimide, amsacrine, anastrozole, asparaginase, bcg, bicalutamide, bleomycin, buserelin, busulfan, campothecin, capecitabine, carboplatin, carmustine, chlorambucil, chloroquine, cisplatin, cladribine, clodronate, colchicine, cyclophosphamide, cyproterone, cytarabine, dacarbazine, dactinomycin, daunorubicin, demethoxyviridin, dichloroacetate, dienestrol, diethylstilbestrol, docetaxel, doxorubicin, epirubicin, estradiol, estramustine, etoposide, everolimus, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, lonidamine, mechlorethamine, medroxyprogesterone, megestrol, melphalan, mercaptopurine, mesna, metformin, methotrexate, mitomycin, mitotane, mitoxantrone, nilutamide, nocodazole, octreotide, oxaliplatin, paclitaxel, pamidronate, pentostatin, perifosine, plicamycin, porfimer, procarbazine, raltitrexed, rituximab, sorafenib, streptozocin, sunitinib, suramin, tamoxifen, temozolomide, temsirolimus, teniposide, testosterone, thioguanine, thiotepa, titanocene dichloride, topotecan, trastuzumab, tretinoin, vinblastine, vincristine, vindesine, and vinorelbine.

10. The method of claim 5, wherein the method further comprises administering non-chemical methods of cancer treatment.

11. The method of claim 10, wherein the method further comprises administering radiation therapy.

12. The method of claim 10, wherein the method further comprises administering surgery, thermoablation, focused ultrasound therapy, cryotherapy, or any combination thereof.

* * * * *